US008715674B2

(12) United States Patent
Zeng

(10) Patent No.: US 8,715,674 B2
(45) Date of Patent: May 6, 2014

(54) ANTIBODIES BINDING TO AN INTRACELLULAR PRL-1 OR PRL-3 POLYPEPTIDE

(75) Inventor: Qi Zeng, Singapore (SG)

(73) Assignee: **Agency for Science, Technology and Research (A*Star)**, Singapore (SG)

(*) Notice: Subject to any disclaimer, the term of this patent is extended or adjusted under 35 U.S.C. 154(b) by 505 days.

(21) Appl. No.: 12/598,442

(22) PCT Filed: May 3, 2008

(86) PCT No.: PCT/SG2008/000161
§ 371 (c)(1),
(2), (4) Date: Nov. 2, 2009

(87) PCT Pub. No.: WO2008/136774
PCT Pub. Date: Nov. 13, 2008

(65) Prior Publication Data
US 2011/0206657 A1 Aug. 25, 2011

Related U.S. Application Data

(60) Provisional application No. 60/924,201, filed on May 3, 2007, provisional application No. 61/064,229, filed on Feb. 22, 2008.

(51) Int. Cl.
*A61K 39/395* (2006.01)
(52) U.S. Cl.
USPC ............... 424/174.1; 424/138.1; 424/139.1; 424/154.1; 424/133.1
(58) Field of Classification Search
None
See application file for complete search history.

(56) References Cited

U.S. PATENT DOCUMENTS

| 7,745,165 B2* | 6/2010 | Vogelstein et al. ............ 435/21 |
| 2005/0047996 A1* | 3/2005 | Vogelstein et al. ........ 424/1.49 |
| 2005/0287644 A1 | 12/2005 | Chiu et al. |
| 2008/0241066 A1* | 10/2008 | Shou et al. ................ 424/9.1 |

FOREIGN PATENT DOCUMENTS

WO 2006/091326 A 8/2006

OTHER PUBLICATIONS

Rudikoff, Giusti, Cook, and Scharff. Single amino acid substitution altering antigen-binding specificity. Proceedings of the National Academy of Science, 1982. vol. 79, p. 1979.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Chen, Wiesmann, Fuh, Li, Christinger, Mc Kay, De Vos, and Lowman. Selection and analysis of an optimized anti-VEGF antibody: crystal structure of an affinity-matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Eck and Wilson. Gene-based therapy. Goodman & Gilman's The Pharmacological basis of Therapeutics, McGraw-Hill, New York, NY. 1996. pp. 77-101.*
Verma and Somia. Gene therapy—promises, problems and prospects. Nature, 1997. vol. 389, pp. 239-242.*
Pfeifer and Verma. Gene therapy: promises and problems. Annual Review of Genomics and Human Genetics, 2001. vol. 2, pp. 177-211.*
Vile, Russell, and Lemoine. Cancer gene therapy: hard lessons and new courses. Gene Therapy, 2000, vol. 7 pp. 2-8.*
Kelland. "Of mice and men": values and liabilities of the athymic nude mouse model in anticancer drug development. European Journal of Cancer, 2004. vol. 40, pp. 827-836.*
Brand et al., Anticancer Res. 2006; 26:463-70.*
Kataja et al., Ann Oncol 2009; 20(sup 4): iv10-14.*
Nelson et al., Ann. Intern Med. 2009; 151:727-737.*
Balmana et al. Ann Oncol 2009; 20(supp 4):iv19-20.*
Editor's Summary, Science Translational Medicine, 2011; 3:99ra85.*
Guo et al., Science Translational Research Medicine 2011; 3:1-10.*
Kaiser H, ScienceNOW, "Antibodies Target Cancer's Insides,", Sep. 7, 2011.*
AACR Journals: Instructions to Authors, available at cancerres. aacrjournals.org/site/misc/ifora.xhtmldownloaded, updated Jun. 2, 2012, last downloaded Oct. 23, 2012.*
Editor's Summary from Sci Transl Med 3 99ra85 (2011).*
Guo et al., Sci Transl Med 3(99) 99ra85: 1-10 (2011).*
Science Now posting "Antibodies Target Cancer's Insides" by Jocelyn Kaiser, posted on Sep. 7, 2011.*
Imai & Takaoka, Nat Rev Cancer, Sep. 2006; 6:714-727.*
PJ Carter, Nat. Rev Immunol, May 2006; 6:343-357.*
Guo et al., Science Translational Medicine 2011; 3:99ra85.*
Editor's Summary, "Targeting Intracellular Oncoproteins with Antibody Therapy or Vaccination," Science Translational Medicine 2011, Sep. 7, 2011.*

(Continued)

*Primary Examiner* — Sheela J Huff
*Assistant Examiner* — Jessica H Roark
(74) *Attorney, Agent, or Firm* — Nixon Peabody LLP; David S. Resnick; Mark J. FitzGerald

(57) ABSTRACT

We provide an antibody capable of binding to an intracellular PRL-1 or PRL-3 polypeptide, in which the antibody is capable of binding to an epitope bound by antibody 269, antibody 223 or antibody 318. Such anti-PRL antibodies may be capable of binding to intracellular PRL-1 or PRL-3. They may be suitable for use as therapies against cancer or metastasis thereof, or in clinical diagnosis to identify PRL-3 or PRL-1 positive patients.

8 Claims, 25 Drawing Sheets

(56) References Cited

OTHER PUBLICATIONS

Kaiser, J., Editorial Summary "Antibodies Target Cancer's Insides" in Science Now, Sep. 2011.*

Deng et al: 'In vivo cell penetration and intracellular transport of anti-Sm and anti-La autoantibodies.' International Immunology vol. 12, No. 4, Apr. 1, 2000, pp. 415-423.

Guo, K. et al., Cancer Biology and Therapy, 3(10):945-951 (2004). "Catalytic domain of PRL-3 plays an essential role in tumor metastasis. Formation of PRL-3 tumors inside the blood vessels."

Guo, K. et al., Cancer Biology and Therapy, 7(5):752-759 (2008). "Monoclonal antibodies target intracellular PRL phosphatases to inhibit cancer metastases in mice."

Li et al., Biochemical and Biophysical Research Communications, 348(1):229-237 (2006). "Inhibition of PRL-3 gene expression in gastric cancer cell line SGC7901 via microRNA suppressed reduces peritoneal metastasis."

Li, J. et al., Clinical Cancer Research, 11(6):2195-2204 (2005). "Generation of PRL-3- and PRL-1-specific monoclonal antibodies as potential diagnostic markers for cancer metastases."

Peng, L. et al., Hybridoma and Hybridomics, 23(1):23-27 (2004). "Preparation and characterization of monoclonal antibody against protein tyrosine phosphatase PRL-3."

Polato, F. et al., Clinical Cancer Research, 11(19):6835-6839 (2005). "PRL-3 phosphatase is implicated in ovarian cancer growth."

Sager, J.A. et al., Cancer Biology and Therapy, 3(10):952-953 (2004). "PRL-3. A phosphatase for metastasis?"

Somers, K.D. et al., International Journal of Cancer, 107(5):773-780 (2003). "Orthotopic treatment model of prostate cancer and metastasis in the immunocompetent mouse: efficacy of flt3 ligand immunotherapy."

Stephens, B.J. et al., Molecular Cancer Therapeutics, 4(11):1653-1661 (2005). "PRL phosphatases as potential molecular targets in cancer."

Zeng, Q. et al., Cancer Research, 63(11):2716-2722 (2003). "PRL-3 and PRL-1 promote cell migration, invasion, and metastasis."

* cited by examiner

PRL-3 mAb blocks EGFP-PRL-3 metastatic lung tumors

Metastatic lung tumors formed by CT26 colon cancer cells

Tumours formed by A2780 human ovarian cancer cells

Live parental CHO cells

Serum-starved CHO cells

HCT116 (2-month)

A2780 (1-month)

DLD-1 (3.5-month)

DLD-1+EGFP-PRL-3 (2-month)

A

Lung Sections

B

Blood Smears

PRL-1 #269

PRL-3 #318

ANTIBODIES BINDING TO AN INTRACELLULAR PRL-1 OR PRL-3 POLYPEPTIDE

CROSS REFERENCE TO RELATED APPLICATIONS

This application is a 371 National Phase Entry Application of International Application No. PCT/SG2008/000161 filed May 3, 2008, which designated the U.S., and which claims the benefit of priority under 35 U.S.C. §119(e) of U.S. Provisional No. 60/924,201 filed May 3, 2007, and U.S. Provisional No. 61/064,229 filed Feb. 22, 2008, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Jan. 25, 2013, is named 629156US.txt and is 16,452 bytes in size.

FIELD

The present invention relates to the fields of medicine, cell biology, molecular biology and biochemistry. This invention also relates to the field of medicine.

In particular, it relates to treatment and diagnosis of diseases, in particular cancer, as well as compositions for such use.

BACKGROUND

Cancer is a serious health problem across the world. It is estimated that 7.6 million people in the world died of cancer in 2007. In the UK for example, cancer is responsible for 126,000 deaths per year. One in four people die from cancer.

Known treatments for cancer include surgery, chemotherapy and radiotherapy. Many cancers can be cured if detected early enough.

100 years ago, the concept of antibodies as "magic bullets" was proposed by the German chemist Paul Ehrlich. Antibodies are capable of recognising and binding to their antigens in a specific manner and are therefore ideal agents for recognizing and destroying malignant cells via the immune system. For this reason, they constitute the most rapidly growing class of human therapeutics for cancer.

A number of potential cancer or tumour markers and cancer antigens have been identified in the literature and antibody therapies have been developed against some of them.

For example, the well-known cancer therapy Herceptin (Trastuzumab) is a monoclonal antibody that can kill HER2-positive cancer cells. Herceptin binds to the HER2 (human epidermal growth factor receptor 2) antigen on the cancer cell. Likewise, Bevacizumab (Avastin™) is a monoclonal antibody targeted against vascular endothelial growth factor (VEGF), one of the growth factors implicated in the formation of new blood vessels. By inhibiting angiogenesis, Bevacizumab prevents tumour cells from receiving a constant supply of blood to receive the oxygen and nutrients the tumour needs to survive.

However, the applicability of antibody therapeutics for different cancers is not universal. One of the limitations that has prevented the general use of antibody therapeutics is the large size of antibody molecules and their consequent inability to cross the plasma or cell membrane. In the absence of modification, antibodies (including monoclonal antibodies) are only generally suitable for targeting cancer antigens located at the surface or exterior of host cells[14-15]. In the examples above, HER2 receptor is located on the cell surface and is hence accessible for antibody binding by Herceptin. Likewise, VEGF is secreted into the bloodstream and is able to be bound by Bevacizumab.

PRLs are intracellular C-terminally prenylated proteins. Mutant forms of PRLs that lack the prenylation signal are often localized in nuclei[16-17]. The localization of PRL-1 and PRL-3 to the inner leaflet of the plasma membrane and early endosomes was revealed by EM immunogold labeling[18]. Over-expression of PRL-3 and PRL-1 has been shown to be associated with a variety of human cancers[3-12,19]. PRL-1 and PRL-3 are known to be associated with tumour metastasis. It is known that most cancer patients die from metastases and not from their primary disease.

There is an urgent need for effective ways of preventing cancer metastasis. Antibodies have not hitherto been used for targeting intracellular antigens or cancer markers because of the inability of the antibodies to cross the cell membrane and the consequent inaccessibility of the antigen.

SUMMARY

We have now demonstrated that antibodies against PRL-1 and PRL-3 can surprisingly bind to their intracellular targets.

According to the expectation in the literature, targeting intracellular PRLs with antibodies to ablate cancer cells and cancer metastasis has never been previously thought to be possible because of their intracellular location. We have shown that this is not the case, and provide for anti-PRL-1 and anti-PRL-3 antibodies as cancer therapies, particularly therapies for cancer metastasis.

Li et al (2005) described the generation of PRL-1 and PRL-3 specific monoclonal antibodies. However, the sequences of these antibodies and the sequences of the variable regions of these antibodies have not been published. Furthermore, the hybridomas producing these antibodies have not been and are not so far publicly accessible. Accordingly, the antibodies described in Li et al (2005) have not so far been made available to the public. Furthermore, there is no suggestion that the antibodies may be used for therapy of cancer, in view of the intracellular location of PRL-1 and PRL-3.

We disclose the variable regions of two mouse monoclonal antibodies against PRL-1 (269 and 223) and one mouse monoclonal antibody against PRL-3 (318). We disclose epitopes bound by anti-PRL-1 antibody 269 and anti-PRL-3 antibody 318. We further disclose methods of producing these antibodies as well as methods of making antibodies which have the same or similar binding properties as these antibodies, each of which has hitherto not been possible.

According to a 1$^{st}$ aspect of the present invention, we provide an antibody, capable of binding to an PRL-1 or PRL-3 polypeptide, in which the antibody is capable of binding to an epitope bound by antibody 269, antibody 223 or antibody 318, or a variant, homologue, derivative or fragment thereof.

The antibody may be capable of binding to an epitope on a PRL-1 polypeptide bound by antibody 269. The antibody may comprise an anti-PRL1 antibody capable of binding to an epitope TYKNMR (SEQ ID NO: 13) or TLNKFI (SEQ ID NO: 14), or both, or a variant, homologue, derivative or fragment thereof.

The antibody may be capable of binding to an epitope on a PRL-3 polypeptide bound by antibody 223 or antibody 318. The antibody may comprise an anti-PRL3 antibody capable of binding to an epitope KAKFYN (SEQ ID NO: 35) or HTHKTR (SEQ ID NO: 39), or both, or a variant, homologue, derivative or fragment thereof.

The antibody may comprise the variable region of monoclonal antibody 269 (SEQ ID NO: 2, SEQ ID NO: 4), the variable region of monoclonal antibody 223 (SEQ ID NO: 6, SEQ ID NO: 8) or the variable region of monoclonal antibody 318 (SEQ ID NO: 10, SEQ ID NO: 12).

There is provided, according to a 2$^{nd}$ aspect of the present invention, an antibody comprising the variable region of monoclonal antibody 269 (SEQ ID NO: 2, SEQ ID NO: 4), or a variant, homologue, derivative or fragment thereof which is capable of binding PRL-1.

We provide, according to a 3$^{rd}$ aspect of the present invention, an antibody comprising the variable region of monoclonal antibody 223 (SEQ ID NO: 6, SEQ ID NO: 8), or a variant, homologue, derivative or fragment thereof which is capable of binding PRL-1.

We provide, according to a 4$^{th}$ aspect of the present invention, an antibody comprising the variable region of monoclonal antibody 318 (SEQ ID NO: 10, SEQ ID NO: 12), or a variant, homologue, derivative or fragment thereof which is capable of binding PRL-3.

The antibody may be capable of binding to an intracellular PRL-1 or PRL-3 polypeptide. The antibody may be capable of crossing the plasma membrane of a cell.

The antibody may be capable of binding to and inhibiting a biological activity of PRL-1 or PRL-3, preferably protein tyrosine phosphatase (PTP) activity.

The antibody may be capable of preventing metastasis of a cancer, preferably colorectal cancer, ovarian cancer, breast cancer, liver cancer, pancreatic cancer, prostate cancer, gastric cancer, lung cancer, penis cancer, cervical cancer, brain cancer, esophageal cancer, bladder carcinoma, kidney renal cell carcinoma, ovary lymphoma and skin melanoma. The cancer may comprise PRL-1 or PRL-3 expressing cancer.

The antibody may comprise a monoclonal antibody or a humanised monoclonal antibody.

As a 5$^{th}$ aspect of the present invention, there is provided a combination comprising an anti-PRL-1 antibody and an anti-PRL-3 antibody, each as described.

We provide, according to a 6$^{th}$ aspect of the present invention, a pharmaceutical composition comprising such an antibody or combination, together with a pharmaceutically acceptable excipient, diluent or carrier.

The present invention, in a 7$^{th}$ aspect, provides an antibody capable of binding to PRL-1 or PRL-3, which may comprise an antibody as described, a combination as set out above or a pharmaceutical composition as set out above for use in a method of treatment or prevention of cancer or metastasis thereof.

The method may comprise exposing a cancer cell to the antibody or combination. The method may comprise administering a therapeutically effective amount of the antibody, combination or composition to an individual suffering or suspected of suffering from cancer. The cancer may comprise a metastatic cancer. The cancer may be a PRL-1 or PRL-3 expressing cancer.

The cancer may comprise colorectal cancer, ovarian cancer, breast cancer, liver cancer, pancreatic cancer, prostate cancer, gastric cancer, lung cancer, penis cancer, cervical cancer, brain cancer, esophageal cancer, bladder carcinoma, kidney renal cell carcinoma, ovary lymphoma and skin melanoma.

The number of metastatic tumours in a treated individual may be reduced by at least 50% compared to an untreated individual. It may be reduced by at least 60%. It may be reduced by at least 70%. It may be reduced by at least 80%. The number of metastatic tumours in a treated individual may be reduced by at least 90% compared to an untreated individual.

In a 8$^{th}$ aspect of the present invention, there is provided an antibody as set out above, a combination as described or a pharmaceutical composition as described for use in a method of diagnosis of a cancer or metastasis thereof.

According to an 9$^{th}$ aspect of the present invention, we provide a diagnostic kit comprising such an antibody, such a combination or such a pharmaceutical composition together with instructions for use in the diagnosis of a cancer or metastasis thereof.

We provide, according to a 10$^{th}$ aspect of the invention, a polypeptide comprising a sequence selected from the group consisting of: SEQ ID NO: 2, SEQ ID NO: 4, SEQ ID NO: 6, SEQ ID NO: 8, SEQ ID NO: 10 or SEQ ID NO: 12, or a variant, homologue, derivative or fragment thereof which is capable of binding PRL.

There is provided, in accordance with a 11$^{th}$ aspect of the present invention, a nucleic acid comprising a sequence capable of encoding a molecule as set out above such as a sequence selected from the group consisting of: SEQ ID NO: 1, SEQ ID NO: 3, SEQ ID NO: 5, SEQ ID NO: 7, SEQ ID NO: 9 and SEQ ID NO: 11, or a variant, homologue, derivative or fragment thereof which is capable of encoding a polypeptide having PRL binding activity.

As an 12$^{th}$ aspect of the invention, we provide a cell comprising or transformed with such a nucleic acid sequence or a descendent of such a cell.

We provide, according to a 13$^{th}$ aspect of the invention, there is provided a method of producing an antibody as described, the method comprising providing such a cell and expressing the antibody from the cell.

According to a 14$^{th}$ aspect of the present invention, we provide a method of diagnosis of cancer, such as metastatic cancer, in an individual, the method comprising exposing a biological sample from the individual to an antibody as set out above and detecting binding between the antibody and a PRL-1 or PRL-3 polypeptide.

There is provided, according to a 15$^{th}$ aspect of the present invention, a method of treatment or prevention of cancer, such as metastatic cancer, in an individual suffering or suspected to be suffering from cancer, the method comprising administering a therapeutically effective amount of an antibody as described, a combination as described or a composition as described, to the individual.

The method may comprises a feature as set out in any of the above paragraphs.

According to a 16$^{th}$ aspect of the present invention, we provide a method of treatment or prevention of cancer, such as metastatic cancer, in an individual suffering or suspected to be suffering from cancer, the method comprising diagnosing cancer in the individual by a method as described and treating the individual by a method as described.

According to a 17$^{th}$ aspect of the present invention, we provide method of detecting a metastatic cell, the method comprising exposing a candidate cell to an antibody as described above and detecting expression of PRL-1 or PRL-3 polypeptide by the cell.

According to a 18$^{th}$ aspect of the present invention, we provide method of producing an animal model for metastatic tumours, the method comprising: (a) administering a plurality of metastatic cancer cells, such as a PRL-1 or PRL-3 expressing cancer cells, into a first animal; (b) allowing the cells to develop into metastatic tumours in the first animal; (c) extracting a metastatic tumour from the first animal and deriving a cell line from the metastatic tumour; and (d) administering a plurality of cells of the cell line into a second animal.

According to an 19th aspect of the present invention, we provide an animal model obtainable by such a method.

According to a 20th aspect of the present invention, we provide use of an animal model produced by such a method or as set out above as a model for metastatic tumours.

According to a 21st aspect of the present invention, we provide method comprising the steps of providing an antibody as described and allowing the antibody to bind to a PRL-1 or PRL-3 polypeptide.

The antibody may be allowed to bind to a cell expressing a PRL-1 polypeptide or a PRL-3 polypeptide. The PRL-1 may comprise an intracellular PRL-1 polypeptide. The PRL-3 polypeptide may comprise an intracellular PRL-3 polypeptide.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements) *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

DETAILED DESCRIPTION

Anti-PRL Antibodies

Figure 1:
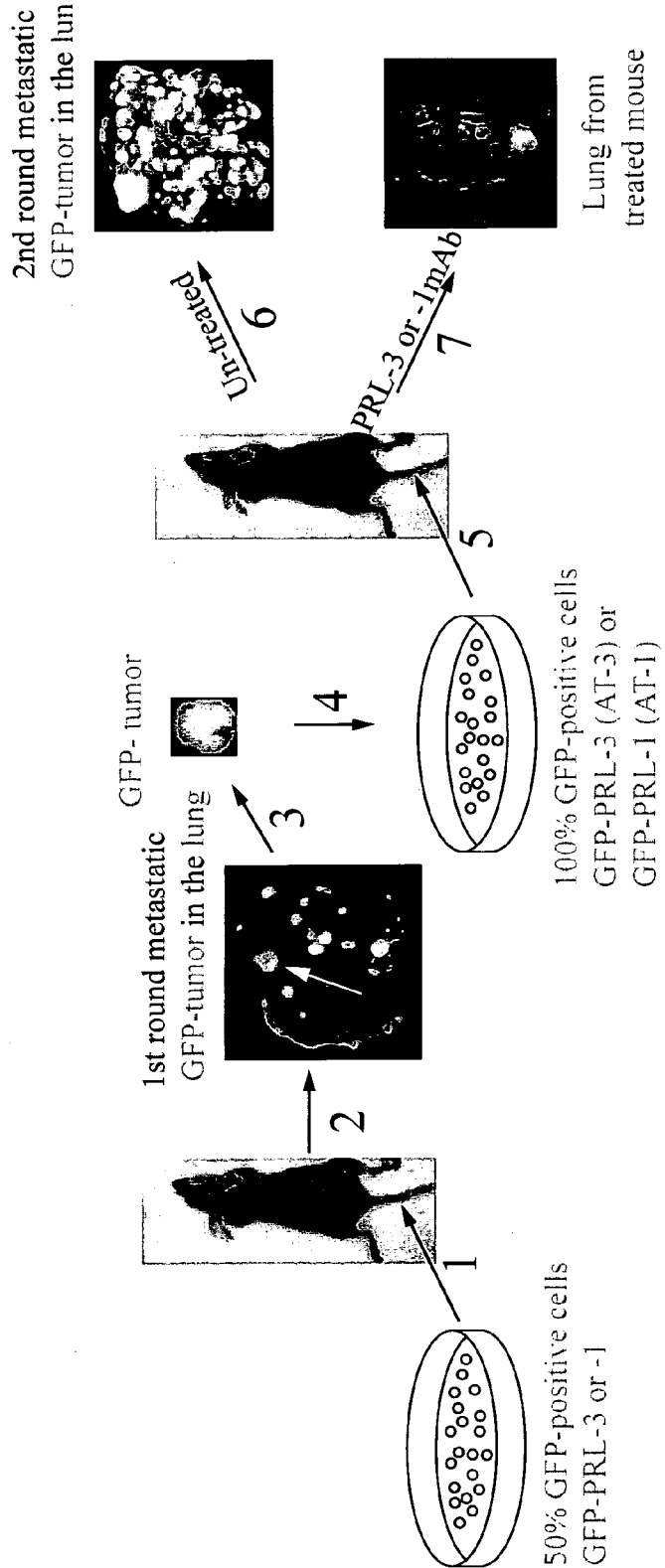
FIG. 1. Seven-step animal model for rapid formation of aggressive lung tumor metastases 1. Generation of CHO stable pools with 50% of cells expressing EGFP-PRL-3 or EGFP-PRL-1 as described previously[8]. 2. Injection of $1 \times 10^6$ of these cells via the tail vein into the circulation of nude mice. 3. Isolation of a single EGFP-PRL-3 or EGFP-PRL-1 lung tumor at 3-week post-injection. 4. Dissecting and mincing the tumor in culture dishes to generate homogeneous EGFP-PRL-expressing cell lines (AT-3 or AT-1). 5. Injection of $1 \times 10^6$ AT-3 or AT-1 cells into the circulation via the tail vein of nude mice. 6. Untreated groups: no treatment, PBS or unrelated mouse antibodies. 7. Mice injected with AT-3 cells are treated with PRL-3 mAbs clones #223 or #318 in the form of ascitic fluid or purified IgG; while mice injected with AT-1 cells are either treated with PBS or treated with PRL-1 mAb clone 269 ascitic fluid.

The Examples describe the generation and production of antibodies against PRL proteins, i.e., anti-PRL antibodies. Such anti-PRL antibodies may be capable of binding PRL-1 or PRL-3, preferably intracellular PRL-1 or PRL-3.

Both monoclonal antibodies and humanised monoclonal antibodies and their properties are described in detail in this document and the Examples. The antibodies include monoclonal antibody 269, capable of binding to PRL-1. They also include monoclonal antibody 223 and monoclonal antibody 318, capable of binding to PRL-3. Humanised versions of each of these antibodies are also disclosed.

For the avoidance of doubt, where a specific antibody designation is referred to in this document, this should be taken to include a reference to both the mouse monoclonal antibody (as secreted by a hybridoma), as well as to the humanised version of it, unless the context dictates otherwise. Thus, for example, where antibody 269 is referred to, this includes both the monoclonal antibody 269 (i.e., the mouse hybridoma secreted antibody designated 269), as well as a humanised monoclonal antibody 269.

The specific antibodies described in this document may be produced by a person skilled in the art from the information disclosed in this document, and employing molecular biology techniques which we also describe in detail.

For this purpose, we disclose the sequences of the variable regions of monoclonal antibody 269, monoclonal antibody 223 and monoclonal antibody 318. We further disclose variants, homologues, fragments and derivatives of these variable regions. Using this sequence information, a skilled person may produce antibodies comprising these variable regions or their variants, homologues, fragments and derivatives.

We further disclose the sequences of nucleic acid constructs for expressing these monoclonal antibodies. The sequences of these constructs enable the production of monoclonal antibodies which have identical sequences to 269, 223 or 318. We further disclose variants, homologues, fragments and derivatives of 269, 223 and 318.

Finally, we disclose the sequences of constructs capable of expressing the humanised monoclonal antibodies 269, 223 or 318. We describe methods of expressing the antibodies of interest from cells transfected with the constructs, as well as variants, homologues, fragments and derivatives of these humanised constructs.

Using such sequences and the expression methods, the skilled person may readily transfect relevant host cells and cause them to express the whole monoclonal or humanised anti-PRL-1 and anti-PRL3 antibodies, or variants, homologues, fragments and derivatives thereof.

We further provide for polypeptides in general having PRL binding activity. Such polypeptides include anti-PRL antibodies such as anti-PRL-1 antibodies and anti-PRL3 antibodies. The PRL-binding polypeptides may comprise one or more of the same or similar properties as the monoclonal antibodies 269, 223 and 318. The polypeptides will be referred to for convenience generally as "anti-PRL antibodies".

It is within the skills of a reader to construct binding molecules which may not be (or may not be described as) antibodies or immunoglobulins but which comprise anti-PRL binding activity as described here. Accordingly, and where the context allows the term "anti-PRL antibodies" should be taken to include any molecule so long as it is capable of binding PRL. Such molecules may include polypeptides, small molecules, as well as antibodies and immunoglobulins, and may be identified through various means known in the art, for example by screening a suitable library for PRL binding activity.

The anti-PRL antibodies (which include PRL binding molecules) may comprise similar or identical properties may as the monoclonal antibodies 269, 223 and 318. Such similar or identical properties may in particular include binding properties. The anti-PRL antibodies may in general be capable of binding to PRL polypeptides, e.g., PRL-1 and PRL-3.

Thus, the term "anti-PRL antibody" will be taken to include monoclonal antibodies 269, 223 and 318 (as well as their humanised counterparts). Also included are polypeptides comprising the variable regions of antibodies 269, 223 or 318 or variants, homologues, fragments and derivatives thereof. This term should also be taken to include reference to variants, homologues, fragments and derivatives of the anti-PRL antibodies, as described below, where the context permits.

PRL1 and PRL3 Epitopes

The anti-PRL antibodies may have the same or similar binding specificity, binding affinity and/or binding affinity as 269, 223 or 318. The anti-PRL antibodies may specifically bind to an epitope bound by antibody 269, an epitope bound by antibody 223 or an epitope bound by antibody 318.

Methods are known in the art to determine an epitope that is bound by a particular antibody. Such epitope mapping methods are described for example in Hanson et al., (2006). Respiratory Research, 7:126. Furthermore, a skilled person will be able to generate antibodies and screen them for particular properties. A detailed description of such a method is shown in Example 27. Accordingly, a skilled person will readily be able to identify anti-PRL antibodies which bind to the same epitopes as 269, 223 and 318.

Example 27 shows that anti-PRL1 antibody 269 binds epitopes TYKNMR (SEQ ID NO: 13) and TLNKFI (SEQ ID NO: 14). Accordingly, we provide an anti-PRL antibody such as an anti-PRL1 antibody capable of binding a sequence TYKNMR (SEQ ID NO: 13). We further provide an anti-PRL antibody such as an anti-PRL1 antibody capable of binding a sequence TLNKFI (SEQ ID NO: 14). The anti-PRL antibody may be capable of binding both sequences.

Furthermore, Example 27 shows that anti-PRL3 antibody binds epitopes KAKFYN (SEQ ID NO: 35) and HTHKTR (SEQ ID NO: 39). We therefore provide an anti-PRL antibody such as an anti-PRL3 antibody capable of binding a sequence KAKFYN (SEQ ID NO: 35). We further provide an anti-PRL antibody such as an anti-PRL3 antibody capable of binding a sequence HTHKTR (SEQ ID NO: 39). The anti-PRL antibody may be capable of binding both sequences.

The anti-PRL antibodies may comprise the variable region of antibody 269, or the variable region of antibody 223 or the variable region of antibody 318, each of which is described in detail below. They may comprise the same or different variable regions in a single antibody molecule. They may comprise one variable region, or more than one variable region. Accordingly, we provide the skilled person with the ability to produce any number of antibodies which comprise the same or similar binding reactivity as antibody 269, 223 or 318.

Such antibodies may comprise the full or substantially complete sequences of an antibody (i.e., heavy chain and light chain), or they may comprise a fragment of a whole antibody (such as Fv, F(ab') and F(ab')$_2$ fragments or single chain antibodies (scFv)). The antibodies may further comprise fusion proteins or synthetic proteins which comprise the antigen-binding site of the antibody, as described in detail below. It will also be evident that such antibodies may be engineered for desirable properties, such as lowered host reactivity, reduced rejection, etc.

The engineering could include "humanisation", by which term we mean the inclusion of (or substitution with) one or more human residues or sequences in an antibody sequence such as a mouse antibody sequence. "Humanisation" in the context of this document includes "chimeric" antibodies, in which the antibody comprises discrete sections of mouse and human sequences, e.g., where one or both of the variable regions comprise mouse sequences, and the remainder of the antibody molecule (such as the constant region) comprises human sequences. In such chimeric antibodies, the whole of the variable regions of, for example, a mouse or rat antibody may be expressed along with human constant regions. This provides such a chimeric antibody with human effector functions and also reduces immunogenicity (HAMA) caused by the murine Fc region.

Generally, a "chimeric antibody" may refer to an antibody having either a heavy and light chain encoded by a nucleotide sequence derived from a murine immunoglobulin gene and either a heavy and light chain encoded by a nucleotide sequence derived from a human immunoglobulin gene.

"Humanisation" also includes CDR grafted or reshaped antibodies. It thus includes engineering at a more discrete level, e.g., antibodies in which the mouse variable region has been mutated to include human residues to reduce immunogenicity. In such an antibody, only the complimentarity determining regions from the rodent antibody V-regions may be combined with framework regions from human V-regions. Such antibodies should be more human and less immunogenic than chimaeric antibodies.

The anti-PRL antibody may generally be capable of binding to PRL polypeptide in a number of conditions.

In one embodiment, the binding environment comprises an intracellular condition. That is to say, the anti-PRL antibody may be capable of binding to a PRL polypeptide in an intact or unpermeabilised cell. Such an unpermeabilised cell may comprise a cell which has not been exposed, or not exposed substantially, to a permeabilisation agent such as a detergent (e.g., Triton X-100) or digitonin.

An anti-PRL-3 antibody as described here may be capable of binding to PRL-3 when it is inside the cell, within the cell membrane or encapsulated within the cell. Similarly, a PRL-1 polypeptide may be bound by an anti-PRL-1 antibody, as described generally in this document, in the context of an environment that comprises the interior of a cell. The anti-PRL-1 and anti-PRL3 antibodies may in particular be capable of binding to an intracellular PRL-1 or PRL-3 polypeptide. The intracellular PRL polypeptide may be associated with one or a number of cellular structures, for example, the inner leaflet of the cell membrane, an organelle, a cytoskeletal structure, the nuclear membrane, etc. The PRL polypeptide may be located within the nucleus. In each of these cases, the anti-PRL antibody may be capable of binding to the PRL polypeptide within the intracellular environment.

The anti-PRL antibody may be capable of binding to a PRL polypeptide in an intracellular environment in a number of ways. The anti-PRL antibody may be capable of crossing the plasma membrane. It may be capable of otherwise gaining access to a binding region of the PRL polypeptide, for example by cellular uptake. It may be internalised or translocated or otherwise delivered into the cell by any means.

In another embodiment, the binding condition comprises an extracellular condition. The anti-PRL antibody may therefore be capable of binding to its cognate PRL polypeptide in an extracellular environment.

The anti-PRL antibody may therefore be capable of binding to a PRL polypeptide extracellularly. In other words, an anti-PRL-1 antibody as described here may be capable of binding to PRL-1 when it is outside the cell. Similarly, a PRL-3 polypeptide may be bound by an anti-PRL-3 antibody, as described generally in this document, in the context of an environment that is external to the interior of a cell. The anti-PRL antibody may be capable of binding to a secreted PRL-1 or PRL-3 polypeptide, as the case may be. The PRL-1 or PRL-3 polypeptide may comprise a circulating PRL-1 or PRL-3 polypeptide.

The anti-PRL antibody may be capable of binding to bind to external or externalized PRL polypeptides. They may bind to secreted PRL polypeptides in blood circulation.

The binding between the anti-PRL antibody and its target may be more or less strong or weak, transient, semi-permanent or permanent.

Binding of the anti-PRL antibody to the PRL polypeptide may take place within the cell. Such binding may inactivate, inhibit or lower an activity of the PRL polypeptide. The binding may neutralise a PRL activity. The activity may comprise any biological activity caused by or associated with the PRL polypeptide. The activity may comprise binding to another protein, for example a downstream protein or factor. Binding of anti-PRL antibody to PRL polypeptide may inactivate, inhibit or lower an activity of a downstream protein or factor. The activity may comprise communication with other cells, for example cells such as metastatic cancer cells in circulation. Thus, the anti-PRL antibodies may neutralise PRL polypeptides in blood circulation to prevent PRL-phosphatases from binding with down-stream factors or from their communicating with other cells in circulation.

The activity may comprise a biochemical activity or a pathogenic activity. The biochemical activity may comprise a catalytic activity. The catalytic activity may comprise phosphatase activity. The activity may comprise growth regulating activity, cancer activity, carcinogenic activity or metastatic activity.

The monoclonal antibodies 269, 223 and 318 may be used for treatment of disease in humans or other animals. We show in the Examples that such anti-PRL antibodies have anti-cancer activity. Specifically, the Examples show that the anti-PRL antibodies are capable of preventing metastatic spread of cancer tumours.

Example 9 describes the generation of PRL-over expressing tumours in mice and provides for an animal model for metastasis and cancer therapy. Examples 10 to 12 show that animals treated with anti-PRL antibodies show significantly fewer metastatic lung tumours compared to animals not treated with anti-PRL antibodies. Specifically, the treated animals show about 90% fewer tumours than the untreated animals. The anti-PRL antibodies are capable of binding to blocking the activity of PRL polypeptide, despite its intracellular localisation. Our studies represent the first examples of effectively (~90%) blocking metastasis by using monoclonal antibodies against their respective phosphatases despite their intracellular localization.

We also show that anti-PRL-3 monoclonal antibodies effectively block the formation of metastatic tumours by a human ovarian cancer cell line A2780 that expresses endogenous PRL-3 protein.

Accordingly, we provide for the use of anti-PRL antibodies in the treatment or prevention of disease, such as cancer. The cancer may comprise a metastatic cancer. The anti-PRL antibodies may be used as drugs or therapies to treat metastasis of a cancer, such as an established tumour. They may be used to prevent cancer or metastasis thereof.

The cancer which is treatable or preventable may include one which is associated with expression or over-expression of a PRL protein. The PRL protein may be a relevant member of the family. By this we mean that a cancer which is associated with expression or over-expression of PRL-1 may be treatable or preventable by anti-PRL-1 antibody such as 269, or an antibody having a similar or identical properties. Similarly, a cancer which is associated with expression or over-expression of PRL-3 may be treatable or preventable by anti-PRL-3 antibody such as 223 or 318, or an antibody having a similar or identical properties.

The cancer may include any of a number of cancers, such as colorectal cancer, ovarian cancer, breast cancer, liver cancer, pancreatic cancer, prostate cancer, gastric cancer, lung cancer, penis cancer, cervical cancer, brain cancer, esophageal cancer, bladder carcinoma, kidney renal cell carcinoma, ovary lymphoma and skin melanoma.

The treatment may comprise generally contacting a cancer cell, or a cell suspected of being a cancer cell, with an anti-PRL antibody. The cell may be exposed to an anti-PRL-1 antibody. It may or in addition be exposed to an anti-PRL-3 antibody. It may be exposed to both an anti-PRL-1 antibody and an anti-PRL-3 antibody. Where this is so, the cell may be exposed to both antibodies together, or individually in sequence. The exposure may be repeated a number of times. Any combination of anti-PRL-1 antibody and an anti-PRL-3 antibody in whatever amount or relative amount, in whatever timing of exposure, may be used.

We therefore provide for the use of combinations of anti-PRL-1 antibodies and anti-PRL-3 antibodies, as described above, in the treatment of disease such as cancer.

The cell may be an individual cell, or it may be in a cell mass, such as a cancer or tumour cell mass. The cell may be inside the body of an organism. The organism may be one which is known to be suffering from cancer, or it could be one in which cancer is suspected. The treatment may comprise administering the antibody or antibodies to the organism. As above, a single antibody may be administered, or a combination of anti-PRL-1 antibody and an anti-PRL-3 antibody may be administered. The administration may be simultaneous or sequential, as described above. Thus, the treatment may comprise administering an anti-PRL-1 antibody simultaneously or sequentially with an anti-PRL-3 antibody to the individual.

The anti-PRL antibody may generally comprise any immunoglobulin capable of binding to a PRL molecule, as described in more detail below.

PRL-1

The following text is adapted from OMIM entry 601585.

PRL-1 is also known as Protein-Tyrosine Phosphatase, Type 4a, 1; PTP4A1, Phophatase of Regenerating Liver 1, PTP(CAAX1). The chromosomal location of PRL-1 is at gene map locus 6q12.

Cellular processes involving growth, differentiation, and metabolism are often regulated in part by protein phosphorylation and dephosphorylation. The protein tyrosine phosphatases (PTPs), which hydrolyze the phosphate monoesters of tyrosine residues, all share a common active site motif and are classified into 3 groups.

These include the receptor-like PTPs, the intracellular PTPs, and the dual-specificity PTPs, which can dephosphorylate at serine and threonine residues as well as at tyrosines.

Diamond et al. 1994, Cell. Biol. 14: 3752-3762, described a PTP from regenerating rat liver that is a member of a fourth class. The gene, which they designated Prl1, was one of many immediate-early genes and expressed mainly in the nucleus. Over-expression of Prl1 in stably transfected cells resulted in a transformed phenotype, which suggested that it may play some role in tumorigenesis.

By using an in vitro prenylation screen, Cates et al., 1996, Cancer Lett. 110: 49-55, isolated 2 human cDNAs encoding PRL1 homologs, designated PTP(CAAX1) and PTP (CAAX2) (PRL2; 601584), that are farnesylated in vitro by mammalian farnesyl:protein transferase. Overexpression of these PTPs in epithelial cells caused a transformed phenotype in cultured cells and tumor growth in nude mice. The authors concluded that PTP(CAAX1) and PTP(CAAX2) represent a novel class of isoprenylated, oncogenic PTPs.

Peng et al. 1998, J. Biol. Chem. 273: 17286-17295, reported that the human PTP(CAAX1) gene, or PRL1, is composed of 6 exons and contains 2 promoters. The predicted mouse, rat, and human PRL1 proteins are identical. Zeng et al. 1998, Biochem. Biophys. Res. Commun. 244: 421-427, determined that the human PRL1 and PRL2 proteins share 87% amino acid sequence identity. By FISH, Peng et al. (1998) mapped the PRL1 gene to 6q12.

Where the term "PRL-1" is used, this should be taken to refer to any PRL-1sequence, including a PRL-1 protein or a PRL-1 nucleic acid and any fragment, variant homologue, derivative, variant thereof.

The properties and activities of PRL-1 are described in this document, for example, in the references.

[End of Text Adapted from OMIM]

Mouse and human PRL-1 proteins were described in detail in Zeng et al (1998), supra.

PRL-1 Sequences

The methods and compositions described here make use of PRL-1 polypeptides, which are described in detail below. As used here, the term "PRL-1" is intended to refer to a sequence set out in Table D1 below.

TABLE D1

PRL-1 Sequences

| Unigene | Description |
| --- | --- |
| NM_003463.3 | *Homo sapiens* protein tyrosine phosphatase type IVA, member 1 (PTP4A1), mRNA |
| CR602427.1 | full-length cDNA clone CS0DK012YJ03 of HeLa cells Cot 25-normalized of *Homo sapiens* (human) |
| CR599216.1 | full-length cDNA clone CL0BB007ZF05 of Neuroblastoma of *Homo sapiens* (human) |
| CR596545.1 | full-length cDNA clone CS0DK010YM06 of HeLa cells Cot 25-normalized of *Homo sapiens* (human) |
| CR749458.1 | *Homo sapiens* mRNA; cDNA DKFZp779M0721 (from clone DKFZp779M0721) |
| BC045571.1 | *Homo sapiens* protein tyrosine phosphatase type IVA, member 1, mRNA (cDNA clone MGC: 57320 IMAGE: 4826233), complete cds |
| AJ420505.1 | *Homo sapiens* mRNA full length insert cDNA clone EUROIMAGE 2096405 |
| AK312526.1 | *Homo sapiens* cDNA, FLJ92892 |
| BC023975.2 | *Homo sapiens* protein tyrosine phosphatase type IVA, member 1, mRNA (cDNA clone MGC: 1659 IMAGE: 2960001), complete cds |
| U69701.1 | Human protein tyrosine phosphatase hPRL-1N mRNA, partial cds |
| U48296.1 | *Homo sapiens* protein tyrosine phosphatase PTPCAAX1 (hPTPCAAX1) mRNA, complete cds |
| AK081491.1 | *Mus musculus* 16 days embryo head cDNA, RIKEN full-length enriched library, clone: C130021B01 product: protein tyrosine phosphatase 4a1, full insert sequence |

TABLE D1-continued

PRL-1 Sequences

| Unigene | Description |
| --- | --- |
| AK078120.1 | *Mus musculus* adult male medulla oblongata cDNA, RIKEN full-length enriched library, clone: 6330521E18 product: protein tyrosine phosphatase 4a1, full insert sequence |
| BC055039.1 | *Mus musculus* protein tyrosine phosphatase 4a1, mRNA (cDNA clone MGC: 62623 IMAGE: 6396041), complete cds |
| AK199907.1 | *Mus musculus* cDNA, clone: Y1G0132L24, strand: minus, reference: ENSEMBL: Mouse-Transcript-ENST: ENSMUST00000061959, based on BLAT search |
| AK198788.1 | *Mus musculus* cDNA, clone: Y1G0129D05, strand: plus, reference: ENSEMBL: Mouse-Transcript-ENST: ENSMUST00000061959, based on BLAT search |
| AK192767.1 | *Mus musculus* cDNA, clone: Y1G0109N22, strand: plus, reference: ENSEMBL: Mouse-Transcript-ENST: ENSMUST00000055216, based on BLAT search |
| AK187266.1 | *Mus musculus* cDNA, clone: Y0G0140O11, strand: plus, reference: ENSEMBL: Mouse-Transcript-ENST: ENSMUST00000061959, based on BLAT search |
| BC086787.1 | *Mus musculus* protein tyrosine phosphatase 4a1, mRNA (cDNA clone MGC: 102117 IMAGE: 30538771), complete cds |
| BC094447.1 | *Mus musculus* protein tyrosine phosphatase 4a1, mRNA (cDNA clone MGC: 102501 IMAGE: 3990529), complete cds |
| AK150506.1 | *Mus musculus* bone marrow macrophage cDNA, RIKEN full-length enriched library, clone: I830008L20 product: protein tyrosine phosphatase 4a1, full insert sequence |
| AK148288.1 | *Mus musculus* B16 F10Y cells cDNA, RIKEN full-length enriched library, clone: G370079M23 product: protein tyrosine phosphatase 4a1, full insert sequence |
| AK151533.1 | *Mus musculus* bone marrow macrophage cDNA, RIKEN full-length enriched library, clone: I830031H07 product: protein tyrosine phosphatase 4a1, full insert sequence |
| U84411.1 | *Mus musculus* protein tyrosine phosphatase (PRL-1) mRNA, complete cds |
| NM_011200.2 | *Mus musculus* protein tyrosine phosphatase 4a1 (Ptp4a1), mRNA |
| BC003761.1 | *Mus musculus*, protein tyrosine phosphatase 4a1, clone IMAGE: 3590144, mRNA |
| BC031734.1 | *Mus musculus*, protein tyrosine phosphatase 4a1, clone IMAGE: 3157812, mRNA |

A "PRL-1 polypeptide" may comprise or consist of a human PRL-1 polypeptide, such as the sequence having Unigene accession number NM_003463.3.

Homologues variants and derivatives thereof of any, some or all of these polypeptides are also included. For example, PRL-1 may include Unigene Accession Number U84411.1.

PRL-3

The following text is adapted from OMIM entry 606449.

PRL-3 is also known as Protein-Tyrosine Phosphatase, Type 4A, 3; PTP4A3. The chromosomal location of PRL-3 is at gene map locus 8q24.3.

In the heart, protein kinases regulate contractility, ion transport, metabolism, and gene expression. Phosphatases, in addition to their role in dephosphorylation, are involved in cardiac hypertrophy and dysfunction.

By database searching and screening of a heart cDNA library, Matter et al. 2001, Biochem. Biophys. Res. Commun. 283: 1061-1068 identified a cDNA encoding PTP4A3, which they termed PRL3. The deduced PRL3 protein is 76% identical to PRL1 (PTP4A 1; 601585) and 96% identical to mouse Prl3. Northern blot analysis revealed expression of an approximately 2.3-kb PRL3 transcript predominantly in heart and skeletal muscle, with lower expression in pancreas. This expression pattern is distinct from the wider expression of PRL1 and PRL2 (PTP4A2; 601584). In situ hybridization analysis localized PRL3 expression to cardiomyocytes. Tris glycine gel analysis showed that PRL3 is expressed as a 22-kD protein. Functional and mutation analyses indicated that phosphate cleavage is dependent on cys104 of PRL3. Overexpression of PRL3 resulted in increased cell growth. Western blot analysis showed dephosphorylation of p130cas (BCAR1; 602941) in response to angiotensin II (106150), suggesting a role for PRL3 in the modulation of intracellular calcium transients induced by angiotensin II.

To gain insights into the molecular basis for metastasis, Saha et al. 2001, Science 294: 1343-1346 compared the global gene expression profile of metastatic colorectal cancer with that of primary cancers, benign colorectal tumors, and normal colorectal epithelium. PRL3 was expressed at high levels in each of 18 cancer metastases studied but at lower levels in nonmetastatic tumors and normal colorectal epithelium. In 3 of 12 metastases examined, multiple copies of the PRL3 gene were found within a small amplicon located at chromosome 8q24.3. Saha et al. (2001) concluded that the PRL3 gene is important for colorectal cancer metastasis.

Using the Stanford G3 radiation hybrid panel and database sequence analysis, Saha et al. (2001) mapped the PRL3 gene to surrounding marker 145.20. The PRL3 gene is also tightly linked to marker SHGC-22154, which is located at 8q24.3, approximately 3 Mb from the 8q telomere.

[End of Text Adapted from OMIM]

Mouse and human PRL-3 proteins were described in detail in Li et al (2005), Clin Cancer Res; 11:2195-204.

PRL-3 Sequences

The methods and compositions described here make use of PRL-3 polypeptides, which are described in detail below. As used here, the term "PRL-3" is intended to refer to a sequence set out in Table D2 below.

| Unigene | Description |
| --- | --- |
| AF041434.1 | *Homo sapiens* potentially prenylated protein tyrosine phosphatase hPRL-3 mRNA, complete cds |
| BT007303.1 | *Homo sapiens* protein tyrosine phosphatase type IVA, member 3 mRNA, complete cds |
| AK128380.1 | *Homo sapiens* cDNA FLJ46523 fis, clone THYMU3034099 |
| NM_007079.2 | *Homo sapiens* protein tyrosine phosphatase type IVA, member 3 (PTP4A3), transcript variant 2, mRNA |
| AY819648.1 | *Homo sapiens* HCV p7-transregulated protein 2 mRNA, complete cds |
| BC003105.1 | *Homo sapiens* protein tyrosine phosphatase type IVA, member 3, mRNA (cDNA clone MGC: 1950 IMAGE: 3357244), complete cds |
| NM_032611.1 | *Homo sapiens* protein tyrosine phosphatase type IVA, member 3 (PTP4A3), transcript variant 1, mRNA |
| AK311257.1 | *Homo sapiens* cDNA, FLJ18299 |
| U87168.1 | Human protein tyrosine phosphatase homolog hPRL-R mRNA, partial cds |
| AJ276554.1 | *Homo sapiens* mRNA for protein tyrosine phosphatase hPRL-3, short form |
| BC066043.1 | *Mus musculus* protein tyrosine phosphatase 4a3, mRNA (cDNA clone MGC: 90066 IMAGE: 6415021), complete cds |
| AK190358.1 | *Mus musculus* cDNA, clone: Y1G0102I03, strand: plus, reference: ENSEMBL: Mouse-Transcript-ENST: ENSMUST00000053232, based on BLAT search |
| CT010215.1 | *Mus musculus* full open reading frame cDNA clone RZPDo836H0950D for gene Ptp4a3, Protein tyrosine phosphatase 4a3; complete cds, incl. stopcodon |
| AK147489.1 | *Mus musculus* adult male brain UNDEFINED_CELL_LINE cDNA, RIKEN full-length enriched library, clone: M5C1053F14 product: protein tyrosine phosphatase 4a3, full insert sequence |
| AK172192.1 | *Mus musculus* activated spleen cDNA, RIKEN full-length enriched library, clone: F830102P03 product: protein tyrosine phosphatase 4a3, full insert sequence |
| AK143702.1 | *Mus musculus* 6 days neonate spleen cDNA, RIKEN full-length enriched library, clone: F430011C20 product: protein tyrosine phosphatase 4a3, full insert sequence |
| AF035645.1 | *Mus musculus* potentially prenylated protein tyrosine phosphatase mPRL-3 (Prl3) mRNA, complete cds |
| NM_008975.2 | Mus musculus protein tyrosine phosphatase 4a3 (Ptp4a3), mRNA |
| AK014601.1 | *Mus musculus* 0 day neonate skin cDNA, RIKEN full-length enriched library, clone: 4632430E19 product: protein tyrosine phosphatase 4a3, full insert sequence |
| AK004562.1 | *Mus musculus* adult male lung cDNA, RIKEN full-length enriched library, clone: 1200003F10 product: protein tyrosine phosphatase 4a3, full insert sequence |
| AK003954.1 | *Mus musculus* 18-day embryo whole body cDNA, RIKEN full-length enriched library, clone: 1110029E17 product: protein tyrosine phosphatase 4a3, full insert sequence |
| BC027445.1 | *Mus musculus* protein tyrosine phosphatase 4a3, mRNA (cDNA clone MGC: 36146 IMAGE: 4482106), complete cds |

A "PRL-3 polypeptide" may comprise or consist of a human PRL-3 polypeptide, such as the sequence having Unigene accession number AF041434.1.

Homologues variants and derivatives thereof of any, some or all of these polypeptides are also included. For example, PRL-3 may include Unigene Accession Number BC066043.1.

PRL-1 and PRL-3 Polypeptides

PRL-1 and PRL-3 polypeptides may be used for a variety of means, for example, for production or screening of anti-PRL-1 and anti-PRL-3 agents such as specific PRL-1 and PRL-3 binding agents, in particular, anti-PRL antibodies. These are described in further detail below. The expression of PRL-1 and PRL-3 polypeptides may be detected for diagnosis or detection of cancer, in particular breast cancer.

A "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins—Structure and Molecular Properties,* 2nd Ed., T. E. Creighton, W. H. Freeman and Company, New York, 1993 and Wold, F., *Posttranslational Protein Modifications: Perspectives and Prospects*, pgs. 1-12 in *Posttranslational Covalent Modification of Proteins*, B. C. Johnson, Ed., Academic Press, New York, 1983; Seifter et al., "Analysis for protein modifications and nonprotein cofactors", *Meth Enzymol* (1990) 182:626-646 and Rattan et al, "Protein Synthesis: Posttranslational Modifications and Aging", *Ann NY Acad Sci* (1992) 663:48-62.

The term "polypeptide" includes the various synthetic peptide variations known in the art, such as a retroinverso D peptides. The peptide may be an antigenic determinant and/or a T-cell epitope. The peptide may be immunogenic in vivo. The peptide may be capable of inducing neutralising antibodies in vivo.

As applied to PRL-1 and PRL-3, the resultant amino acid sequence may have one or more activities, such as biological activities in common with a PRL-1 or PRL-3 polypeptide, for example a human PRL-1 or PRL-3 polypeptide. For example, a PRL-1 or PRL-3 homologue may have a increased expression level in cancer cells compared to normal breast cells. In particular, the term "homologue" covers identity with respect to structure and/or function providing the resultant amino acid sequence has PRL-1 pr PRL-3 activity. With respect to sequence identity (i.e. similarity), there may be at least 70%, such as at least 75%, such as at least 85%, such as at least 90% sequence identity. There may be at least 95%, such as at least 98%, sequence identity. These terms also encompass polypeptides derived from amino acids which are allelic variations of the PRL-1 or PRL-3 nucleic acid sequence.

Where reference is made to the "activity" or "biological activity" of a polypeptide such as PRL-1 and PRL-3, these terms are intended to refer to the metabolic or physiological function of PRL-1 and PRL-3, including similar activities or improved activities or these activities with decreased undesirable side effects. Also included are antigenic and immunogenic activities of PRL-1 and PRL-3. Examples of such activities, and methods of assaying and quantifying these activities, are known in the art, and are described in detail elsewhere in this document.

Antibodies

The terms "antibody" and "immunoglobulin", as used in this document, may be employed interchangeably where the context permits. These term include fragments of proteolytically-cleaved or recombinantly-prepared portions of an antibody molecule that are capable of selectively reacting with or recognising PRL-1 or PRL-3 or an epitope thereof, such as an epitope of PRL-1 bound by 269 or an epitope of PRL-3 bound by 223 or 318.

Epitopes of PRL-1 include TYKNMR (SEQ ID NO: 13) and TLNKFI (SEQ ID NO: 14). Epitopes of PRL-3 include KAKFYN (SEQ ID NO: 35) and HTHKTR (SEQ ID NO: 39).

Non limiting examples of such proteolytic and/or recombinant fragments include Fab, F (ab') 2, Fab', Fv fragments, and single chain antibodies(scFv) containing a VL and VH domain joined by a peptide linker. These Fvs may be covalently or non-covalently linked to form antibodies having two or more binding sites.

By "ScFv molecules" we mean molecules wherein the VH and VL partner domains are linked via a flexible oligopeptide. A general review of the techniques involved in the synthesis of antibody fragments which retain their specific binding sites is to be found in Winter & Milstein (1991) Nature 349, 293-299.

Whole antibodies, and F(ab') 2 fragments are "bivalent". By "bivalent" we mean that the said antibodies and F(ab') fragments have two antigen combining sites. In contrast, Fab, Fv, ScFv and dAb fragments are monovalent having only one antigen combining site.

The anti-PRL antibody may comprise a high affinity antibody with an off rate from $10^{-2}s^{-1}$ to $10^{-4}s^{-1}$. The off rate may be about $2\times10^{-4}s^{-1}$.

The term "off-rate" as used in this document refers to the dissociation rate ($k_{off}$) of an antibody such as an anti-PRL antibody disclosed here. It may be measured using BIAevaluation software (Pharmacia). A low off rate is desirable as it reflects the affinity of an Fab fragment for an antigen.

The term "affinity" is defined in terms of the dissociation rate or off-rate ($k_{off}$) of a an antibody such as an anti-PRL antibody. The lower the off-rate the higher the affinity that a an antibody such as an anti-PRL antibody has for an antigen such as PRL-1 or PRL-3.

The anti-PRL antibody may comprise a peptide per se or form part of a fusion protein.

The anti-PRL antibodies described here include any antibody that comprise PRL-1 or PRL-3 binding activity, such as binding ability to intracellular PRL-1 or PRL-3 or binding to the same epitope bound by 269, 223 or 318 as the case may be, including TYKNMR (SEQ ID NO: 13), TLNKFI (SEQ ID NO: 14), KAKFYN (SEQ ID NO: 35) and HTHKTR (SEQ ID NO: 39).

The anti-PRL antibodies also include the entire or whole antibody, whether mouse, humanised or human, such antibody derivatives and biologically-active fragments. These may include antibody fragments with PRL-1 or PRL-3 binding activity that have amino acid substitutions or have sugars or other molecules attached to amino acid functional groups, etc.

The anti-PRL antibody may comprise isolated antibody or purified antibody. It may be obtainable from or produced by any suitable source, whether natural or not, or it may be a synthetic anti-PRL antibody, a semi-synthetic anti-PRL antibody, a derivatised anti-PRL antibody or a recombinant anti-PRL antibody.

Where the anti-PRL antibody is a non-native anti-PRL antibody, it may include at least a portion of which has been prepared by recombinant DNA techniques or an anti-PRL antibody produced by chemical synthesis techniques or combinations thereof.

The term "derivative" as used in this document includes chemical modification of an anti-PRL antibody. Illustrative of such modifications would be replacement of hydrogen by an alkyl, acyl, or amino group, for example. The sequence of the anti-PRL antibody may be the same as that of the naturally occurring form or it may be a variant, homologue, fragment or derivative thereof.

Antibody Variable Regions

The term "variable region", as used in this document, refers to the variable regions, or domains, of the light chains (VL) and heavy chains (VH) which contain the determinants for binding recognition specificity and for the overall affinity of the antibody against PRL-1 or PRL-3 (or variant, homologue, fragment or derivative), as the case may be.

The variable domains of each pair of light (VL) and heavy chains (VH) are involved in antigen recognition and form the antigen binding site. The domains of the light and heavy chains have the same general structure and each domain has four framework (FR) regions, whose sequences are relatively conserved, connected by three complementarity determining regions (CDRs). The FR regions maintain the structural integrity of the variable domain. The CDRs are the polypeptide segments within the variable domain that mediate binding of the antigen.

The term "constant region", as used in this document, refers to the domains of the light (CL) and heavy (CH) chain of the antibody (or variant, homologue, fragment or derivative) which provide structural stability and other biological functions such as antibody chain association, secretion, transplacental mobility, and complement binding, but which are not involved with binding a PRL-1 or PRL-3 epitope. The amino acid sequence and corresponding exon sequences in the genes of the constant region will be dependent upon the species from which it is derived. However, variations in the amino acid sequence leading to allotypes are relatively limited for particular constant regions within a species. An "allotype" is an antigenic determinant (or epitope) that distinguishes allelic genes.

The variable region of each chain is joined to the constant region by a linking polypeptide sequence. The linkage sequence is coded by a "J" sequence in the light chain gene, and a combination of a "D" sequence and a "J" sequence in the heavy chain gene.

Antibody 269, 223 and 318: Variable Region Sequences

Antibody 269

The nucleic acid sequence of the heavy chain of the variable region of monoclonal antibody 269 is as follows (SEQ ID NO: 1):

GGGAATTCATGAAATGCAGCTGGGTTATTCTCTTCCTGTTTTCAGTAAC

TGCAGGTGTCCACTCCCAGGTCCAGTTTCAGCAGTCTGGGGCTGAACTG

GCAAAACCTGGGGCCTCAGTGAAGATGTCCTGCAAGGCTTCTGGCTACA

CTTTTACTAGTTATCGGATGCACTGGGTAAAACAGAGGCCTGGACAGGG

TCTGGAATGGATTGGATACATTAATCCTAGCACTGGTTATACTGAGTAC

AATCAGAAGTTCAAGGACAAGGCCACATTGACTGCAGACAAATCCTCCA

GCACAGCCTACATGCAACTGAGCAGCCTGACATCTGAGGACTCTGCAGT

CTATTACTGTTCAAGCTATGGTAACTTCGGCTACTGGGGCCAAGGCACC

ACTCTCACAGTCTCCTCAGAGAGTCAGTCCTTCCCAAATGTCTTCCCCC

TCGTAAGCTTGGGA

The amino acid sequence of the heavy chain of the variable region of monoclonal antibody 269 is as follows (SEQ ID NO: 2):

EFMKCSWVILFLFSVTAGVHSQVQFQQSGAELAKPGASVKMSCKASGYT

FTSYRMHWVKQRPGQGLEWIGYINPSTGYTEYNQKFKDKATLTADKSSS

TAYMQLSSLTSEDSAVYYCSSYGNFGYWGQGTTLTVSSESQSFPNVFPL

VSLG

The nucleic acid sequence of the light chain of the variable region of monoclonal antibody 269 is as follows (SEQ ID NO: 3):

CTGTCTACTGCTCTCTGGTGAGAGTCAGTCTCACTTGTCGGGCAAGTCA

GGACATTGGTAGTAGCTTAAACTGGCTTCAGCAGAAAGCAGATGGAACC

ATTAAACGCCTGATCTATGCCACATCCAGTTTAGATTCTGGTGTCCCCA

AAAGGTTCAGTGGCAGTAGGTCTGGGTCAGATTATTCTCTCACCATCAG

CAGCCTTGAGTCTGAAGATTTTGTAGACTATTACTGTCTACAATATGCT

AGTTCTCCGTGGACGTTCGGTGGAGGCACCAAGCTGGAAATCAAACGGG

CTGATGCTGCACCTCACTGGAGATCCTGCAGATCACGCGAACTGTGGCT

GCACCATCTGTCTTCATCTTCCCGCCATCTGATGAGCAGTTGAAATCT

The amino acid sequence of the light chain of the variable region of monoclonal antibody 269 is as follows (SEQ ID NO: 4):

VYCSLVRVSLTCRASQDIGSSLNWLQQKADGTIKRLIYATSSLDSGVPK

RFSGSRSGSDYSLTISSLESEDFVDYYCLQYASSPWTFGGGTKLEIKRA

DAAPHWRSCRSRELWLHHLSSSSRHLMSS

Antibody 223

The nucleic acid sequence of the heavy chain of the variable region of monoclonal antibody 223 is as follows (SEQ ID NO: 5):

GGGAATTCATGGAATGGAGCTGGGTTATTCTCTTCCTCCTGTCAATAAT

TGCAGGTGTCCATTGCCAGGTCCAGCTGCAGCAGTCTGGACCTGAGCTG

GTGAAGCCTGGGGCTTCAGTGAGGATATCCTGCAAGGCTTCTGGCTACA

CCTTCACAAGCTACTATATACACTGGGTGAAGCAGAGGCCTGGACAGGG

ACTTGAGTGGATTGGATGGATTTATCCTGGAAATGTTAATACTGAGTAC

AATGAGAAGTTCAGGGGCAAGGCCACACTGACTGCAGACAAATCCTCCA

GCACAGCCTACATGCAGCTCAGCAGCCTGACCTCTGAGGACTCTGCGGT

CTATTTCTGTGCAAGTGAGGAGAGGAATTACCCCTGGTTTGCTTACTGG

GGCCAAGGGACTCTGGTCACTGTCTCTGCAGCCAAAACGACACCCCCAC

CCGTCTATCCCTTGGTCCCTGGAAGCTTGGGA

The amino acid sequence of the heavy chain of the variable region of monoclonal antibody 223 is as follows (SEQ ID NO: 6):

EFMEWSWVILFLLSIIAGVHCQVQLQQSGPELVKPGASVRISCKASGYT

FTSYYIHWVKQRPGQGLEWIGWIYPGNVNTEYNEKFRGKATLTADKSSS

TAYMQLSSLTSEDSAVYFCASEERNYPWFAYWGQGTLVTVSAAKTTPPP

VYPLVPGSLG

The nucleic acid sequence of the light chain of the variable region of monoclonal antibody 223 is as follows (SEQ ID NO: 7):

TGGGAATTCATGGAGACAGACACACTCCTGCTATGGGTGCTGCTGCTCT

GGGTTCCAGGCTCCACTGGTGACATTGTGCTGACCCAATCTCCAGCTTC

TTTGGCTGTGTCTCTAGGGCAGAGGGCCACCATCTCCTGCAAGGCCAGC

CAAAGTGTTGAAGATGATGGTGAAAATTATATGAACTGGTACCAACAGA

AACCAGGACAGTCACCCAAACTCCTCATCTATGCTGCATCCAATCTAGA

ATCTGGGATCCCAGCCAGGTTCAGTGGCAGTGGGTCTGGGACAGACTTC

ACCCTCAACATCCATCCTGTGGAGGAGGAGGATGCTGCAACCTATTACT

GTCAGCAAAGTAATGAGGATCCATTCACGTTCGGCTCGGGGACAAAGTT

GGAAATAAAACGGGCTGATGCTGCACCAACTGTATCCATCTTCCCACCA

TCCAGTAAGCTTGGG

The amino acid sequence of the light chain of the variable region of monoclonal antibody 223 is as follows (SEQ ID NO: 8):

WEFMETDTLLLWVLLLWVPGSTGDIVLTQSPASLAVSLGQRATISCKASQ

SVEDDGENYMNWYQQKPGQSPKLLIYAASNLESGIPARFSGSGSGTDFTL

NIHPVEEEDAATYYCQQSNEDPFTFGSGTKLEIKRADAAPTVSIFPPSSK

LG

Antibody 318

The nucleic acid sequence of the heavy chain of the variable region of monoclonal antibody 318 is as follows (SEQ ID NO: 9):

GGGAATTCATGGAATGGAGCTGGGTTTTCCTCTTCCTCCTGTCAATAAT

TGCAGGTGTCCATTGCCAGGTCCAGCTGCAGCAGTCTGGACCTGAGCTG

GTGAAGCCTGGGGCTTCAGTGAGGATATCCTGCAAGGCTTCTGGCTACA

CCTTCACAAACTACTATATGCACTGGGTGAAGCAGAGGCCTGGACAGGG

ACTTGAGTGGATTGGATGGATTTATCCTGGAAATGTTAATACTTATTAC

AATGAGAAGTTCAGGGCAAGGCCACACTGACTGCAGACAAATCCTCCAG

CACAGCCTACATGCAGCTCAGCAGCCTGACCTCTGAGGACTCTGCGGTC

TATTTCTGTGCAAGTGAGGAGAGAATTACCCCTGGTTTGCTTACTGGGG

CCAAGGGACTCTGGTCACTGTCTCTGCAGCCAAAACGACACCCCCATCC

GTCTATCCCCTGGTCCCTGGAAGCTTGGGA

The amino acid sequence of the heavy chain of the variable region of monoclonal antibody 318 is as follows (SEQ ID NO: 10):

EFMEWSWVFLFLLSIIAGVHCQVQLQQSGPELVKPGASVRISCKASGYT

FTNYYMHWVKQRPGQGLEWIGWIYPGNVNTYYNEKFRARPH.LQTNPPA

QPTCSSAA.PLRTLRSISVQVRRELPLVCLLGPRDSGHCLCSQNDTPIR

LSPGPWKLG

The nucleic acid sequence of the light chain of the variable region of monoclonal antibody 318 is as follows (SEQ ID NO: 11):

ACTAGTCGACATGGAGTCAGACACACTGCTGTTATGGGTACTGCTGCTC

TGGGTTCCAGGTTCCACTGGTGACATTGTGCTGACACAGTCTCCTGCTT

CCTTAGCTGTATCTCTGGGGCAGAGGGCCACCATCTCATACAGGGCCAG

CAAAAGTGTCAGTACATCTGGCTATAGTTATATGCACTGGAACCAACAG

AAACCAGGACAGCCACCCAGACTCCTCATCTATCTTGTATCCAACCTAG

AATCTGGGGTCCCTGCCAGGTTCAGTGGCAGTGGGTCTGGGACAGACTT

CACCCTCAACATCCATCCTGTGGAGGAGGAGGATGCTGCAACCTATTAC

TGTCAGCACATTAGGGAGCTTACACGTTCGGAGGGGGGACCAAGCTGGA

AATAAAACGGGCTGATGCTGCACCAACTGTATCCATCTTCCCACCATCC

ATAAGCTTGGGA

The amino acid sequence of the light chain of the variable region of monoclonal antibody 318 is as follows (SEQ ID NO: 12):

LVDMESDTLLLWVLLLWVPGSTGDIVLTQSPASLAVSLGQRATISYRAS

KSVSTSGYSYMHWNQQKPGQPPRLLIYLVSNLESGVPARFSGSGSGTDF

TLNIHPVEEEDAATYYCQHIRELTRSEGGPSWK

Anti-PRL1 and anti-PRL3 antibodies, according to the methods and compositions described here, may be generated from these variable region sequences by methods known in the art. For example, the heavy and light chain sequences may be recombined into a constant sequence for a chosen antibody, through recombinant genetic engineering techniques which are known to the skilled person.

Constant region sequences are known in the art, and are available from a number of databases, such as the IMGT/LIGM-DB database (described in Giudicelli et al, 2006, Nucleic Acids Research 34(Database Issue):D781-D784 and LeFranc et al (1995) *LIGM-DB/IMGT: An Integrated Database of Ig and TcR, Part of the Immunogenetics Database*. Annals of the New York Academy of Sciences 764 (1), 47-47 doi:10.1111/j.1749-6632.1995.tb55805.x) and the IMGT/GENE-DB database (described in Giudicelli et al, 2005, Nucleic Acids Res. 2005 Jan. 1; 33(Database issue):D256-61). IMGT/LIGM-DB and IMGT/GENE-DB are part of the ImMunoGeneTics Database located at www.ebi.ac.uk/imgt/.

Methods for combining variable regions with given sequences and constant regions to produce whole antibodies are known in the art and are described for example in Example 16 and in Hanson et al., (2006). *Respiratory Research*, 7:126. Fragments of whole antibodies such as Fv, F(ab') and F(ab')$_2$ fragments or single chain antibodies (scFv) may be produced by means known in the art.

Using the disclosed sequences and the methods described in the literature, for example, the heavy and light chains of the variable region of antibody 318, having the sequences shown above, may be transgenically fused to a mouse IgG constant region sequence to produce a mouse monoclonal anti-PRL-3 antibody. Similarly, the 318 variable region may be recombinantly expressed with the constant region of a human IgG antibody to produce a humanized anti-PRL-3 antibody. Variable regions of 223 and 269 antibodies may be engineered with mouse or human IgG constant regions to produce mouse monoclonal or humanized antibodies capable of binding to PRL-1 polypeptide.

Detection and Diagnostic Methods

Detection of Expression of PRL-1 and PRL-3

Expression of PRL-1 and PRL-3 in cancer tissue is up-regulated when compared to normal tissue.

Accordingly, we provide for a method of diagnosis of cancer, including metastatic, aggressive or invasive cancer, comprising detecting modulation of expression of PRL-1 and PRL-3, such as up-regulation of expression of PRL-1 and PRL-3 in a cell or tissue of an individual.

The method may comprise use of the anti-PRL antibodies described in this document. The anti-PRL antibodies may be used in immunoassays to detect and assay the quantity of PRL-1 or PRL-3 in a biological sample, and hence provide an indication of the level of expression of PRL-1 or PRL-3 in a cell, tissue, organ or individual from which the sample is derived. Immunoassays include ELISA, Western Blot, etc, and methods of employing these to assess PRL-1 and PRL-3 expression are known to the skilled reader.

Detection of PRL-1 and PRL-3 expression, activity or amount may be used to provide a method of determining the proliferative state of a cell. Thus, a proliferative cell is one with high levels of PRL-1 and PRL-3 expression, activity or amount compared to a normal cell. Similarly, a non-proliferative cell may be one with low levels PRL-1 and PRL-3 expression, activity or amount compared to a normal cell.

Such detection may also be used to determine whether a cell will become invasive or aggressive. Thus, detection of a high level of PRL-1 and PRL-3 expression, amount or activity of PRL-1 and PRL-3 in the cell may indicate that the cell is likely to be or become aggressive, metastatic or invasive. Similarly, if a cell has a low level of PRL-1 and PRL-3 expression, amount or activity, the cell is not or is not likely to be aggressive, metastatic or invasive.

It will be appreciated that as the level of PRL-1 and PRL-3 varies with the aggressiveness of a tumour, that detection of PRL-1 and PRL-3 expression, amount or activity may also be used to predict a survival rate of an individual with cancer, i.e., high levels of PRL-1 and PRL-3 indicating a lower survival rate or probability and low levels of PRL-1 and PRL-3 indicating a higher survival rate or probability, both as compared to individuals or cognate populations with normal levels of PRL-1 and PRL-3. Detection of expression, amount or activity of PRL-1 and PRL-3 may therefore be used as a method of prognosis of an individual with cancer.

Detection of PRL-1 and PRL-3 expression, amount or level may be used to determine the likelihood of success of a particular therapy in an individual with a cancer. It may be used in a method of determining whether a tumour in an individual is, or is likely to be, an invasive or metastatic tumour.

The diagnostic methods described in this document may be combined with the therapeutic methods described. Thus, we provide for a method of treatment, prophylaxis or alleviation of cancer in an individual, the method comprising detecting modulation of expression, amount or activity of PRL-1 and PRL-3 in a cell of the individual and administering an appropriate therapy to the individual based on the aggressiveness of the tumour.

Typically, physical examination X-rays are used for the detection of cancer. A biopsy of the tumour is typically taken for histopathological examination for the diagnosis of cancer. Detection of PRL-1 and PRL-3 expression, amount or activity can be used to diagnose, or further confirm the diagnosis of, cancer, along with the standard histopathological procedures. This may be especially useful when the histopathological analysis does not yield a clear result.

The presence and quantity of PRL-1 and PRL-3 polypeptides and nucleic acids may be detected in a sample as described in further detail below. Thus, the PRL-1 and PRL-3 associated diseases, including cancer, can be diagnosed by methods comprising determining from a sample derived from a subject an abnormally decreased or increased expression, amount or activity, such as a increased expression, amount or activity, of the PRL-1 and PRL-3 polypeptide or PRL-1 and PRL-3 mRNA.

The sample may comprise a cell or tissue sample from an organism or individual suffering or suspected to be suffering from a disease associated with increased, reduced or otherwise abnormal PRL-1 and PRL-3 expression, amount or activity, including spatial or temporal changes in level or pattern of expression, amount or activity. The level or pattern of expression, amount or activity of PRL-1 and PRL-3 in an organism suffering from or suspected to be suffering from such a disease may be usefully compared with the level or pattern of expression, amount or activity in a normal organism as a means of diagnosis of disease.

The sample may comprise a cell or tissue sample from an individual suffering or suspected to be suffering from cancer, such as a relevant tissue or cell sample.

In some embodiments, an increased level of expression, amount or activity of PRL-1 and PRL-3 is detected in the sample. The level of PRL-1 and PRL-3 may be increased to a significant extent when compared to normal cells, or cells known not to be cancerous. Such cells may be obtained from the individual being tested, or another individual, such as those matched to the tested individual by age, weight, lifestyle, etc.

In some embodiments, the level of expression, amount or activity of PRL-1 and PRL-3 is increased by 10%, 20%, 30% or 40% or more. In some embodiments, the level of expression, amount or activity of PRL-1 and PRL-3 is increased by 45% or more, such as 50% or more, as judged by cDNA hybridisation.

The expression, amount or activity of PRL-1 and PRL-3 may be detected in a number of ways, as known in the art, and as described in further detail below. Typically, the amount of PRL-1 and PRL-3 in a sample of tissue from an individual is measured, and compared with a sample from an unaffected individual. Both PRL-1 and PRL-3 nucleic acid, as well as PRL-1 and PRL-3 polypeptide levels may be measured.

Detection of the amount, activity or expression of PRL-1 and PRL-3 may be used to grade the cancer. For example, a high level of amount, activity or expression of PRL-1 and PRL-3 may indicate an aggressive, invasive or metastatic cancer. Similarly, a low level of amount, activity or expression of PRL-1 and PRL-3 may indicate a non-aggressive, non-invasive or non-metastatic cancer. Such a grading system may be used in conjunction with established grading systems.

Levels of PRL-1 and PRL-3 gene expression may be determined using a number of different techniques.

Measuring Expression of PRL-1 and PRL-3 at the RNA Level

PRL-1 and PRL-3 gene expression can be detected at the RNA level.

In one embodiment therefore, we disclose a method of detecting the presence of a nucleic acid comprising a PRL-1 and PRL-3 nucleic acid in a sample, by contacting the sample with at least one nucleic acid probe which is specific for the PRL-1 and PRL-3 nucleic acid and monitoring said sample for the presence of the PRL-1 and PRL-3 nucleic acid. For example, the nucleic acid probe may specifically bind to the PRL-1 and PRL-3 nucleic acid, or a portion of it, and binding between the two detected; the presence of the complex itself may also be detected.

RNA detection of expression of PRL-1 and PRL-3 may be used to supplement polypeptide expression assays, as described below, which may employ the anti-PRL antibodies described here.

Thus, in one embodiment, the amount of PRL-1 and PRL-3 nucleic acid in the form of PRL-1 and PRL-3 mRNA may be measured in a sample. PRL-1 and PRL-3 mRNA may be assayed by in situ hybridization, Northern blotting and reverse transcriptase—polymerase chain reaction. Nucleic acid sequences may be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994).

PRL-1 and PRL-3 RNA may be extracted from cells using RNA extraction techniques including, for example, using acid phenol/guanidine isothiocyanate extraction (RNAzol B; Biogenesis), or RNeasy RNA preparation kits (Qiagen). Typical assay formats utilising ribonucleic acid hybridisation include nuclear run-on assays, RT-PCR and RNase protection assays (Melton et al., *Nuc. Acids Res.* 12:7035. Methods for detection which can be employed include radioactive labels, enzyme labels, chemiluminescent labels, fluorescent labels and other suitable labels.

Each of these methods allows quantitative determinations to be made, and are well known in the art. Decreased or increased PRL-1 and PRL-3 expression, amount or activity can therefore be measured at the RNA level using any of the methods well known in the art for the quantitation of polynucleotides. Any suitable probe from a PRL-1 and PRL-3 sequence, for example, any portion of a suitable human PRL-1 and PRL-3 sequence may be used as a probe. Sequences for designing PRL-1 and PRL-3 probes may include a sequence having accession number NM_015472, or a portion thereof.

Typically, RT-PCR is used to amplify RNA targets. In this process, the reverse transcriptase enzyme is used to convert RNA to complementary DNA (cDNA) which can then be amplified to facilitate detection.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification methods have been described in the literature, for example, general reviews of these methods in Landegren, U. et al., *Science* 242:229-237 (1988) and Lewis, R., *Genetic Engineering News* 10:1, 54-55 (1990).

For example, the polymerase chain reaction may be employed to detect PRL-1 and PRL-3 mRNA.

The "polymerase chain reaction" or "PCR" is a nucleic acid amplification method described inter alia in U.S. Pat. Nos. 4,683,195 and 4,683,202. PCR can be used to amplify any known nucleic acid in a diagnostic context (Mok et al., 1994, *Gynaecologic Oncology* 52:247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, *Proc. Natl. Acad. Sci. USA* 87:1874). Ligation amplification reaction or ligation amplification system uses DNA ligase and four oligonucleotides, two per target strand. This technique is described by Wu, D. Y. and Wallace, R. B., 1989, *Genomics* 4:560. In the Q13 Replicase technique, RNA replicase for the bacteriophage Q13, which replicates single-stranded RNA, is used to amplify the target DNA, as described by Lizardi et al., 1988, *Bio/Technology* 6:1197.

A PCR procedure basically involves: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

Reverse transcription-polymerase chain reaction (RT-PCR) may be employed. Quantitative RT-PCR may also be used. Such PCR techniques are well known in the art, and may employ any suitable primer from a PRL-1 and PRL-3 sequence.

Alternative amplification technology can also be exploited. For example, rolling circle amplification (Lizardi et al., 1998, *Nat Genet* 19:225) is an amplification technology available commercially (RCAT™) which is driven by DNA polymerase and can replicate circular oligonucleotide probes with either linear or geometric kinetics under isothermal conditions. A further technique, strand displacement amplification (SDA; Walker et al., 1992, *Proc. Natl. Acad. Sci. USA* 80:392) begins with a specifically defined sequence unique to a specific target.

Measuring Expression of PRL-1 and PRL-3 at the Polypeptide Level

PRL-1 and PRL-3 expression can be detected at the polypeptide level.

In a further embodiment, therefore, PRL-1 and PRL-3 expression, amount or activity may be detected by detecting the presence or amount of PRL-1 and PRL-3 polypeptide in a sample. This may be achieved by using molecules which bind to PRL-1 and PRL-3 polypeptide. Suitable molecules/agents which bind either directly or indirectly to the PRL-1 and PRL-3 polypeptide in order to detect its presence include naturally occurring molecules such as peptides and proteins, for example antibodies, or they may be synthetic molecules.

Thus, we disclose a method of detecting the presence of a PRL-1 and PRL-3 polypeptide by contacting a cell sample with an antibody capable of binding the polypeptide and monitoring said sample for the presence of the polypeptide.

For example, the PRL-1 and PRL-3 polypeptide may be detected using an anti-PRL-1 and PRL-3 antibody as described here. Such antibodies may be made by means described in detail in this document. In a specific example, an anti-PRL-1 antibody may comprise an antibody capable of binding to the same epitope as monoclonal antibody 269. This may include monoclonal antibody 269 itself, an antibody comprising a variable region of antibody 269, or a humanised monoclonal antibody 269.

Similarly, an anti-PRL-3 antibody may comprise an antibody capable of binding to the same epitope as monoclonal antibody 223 or 318. This may include monoclonal antibody 223 or 318 itself, an antibody comprising a variable region of antibody 223 or 318, or a humanised monoclonal antibody 223 or 318.

The assay may conveniently be achieved by monitoring the presence of a complex formed between the antibody and the polypeptide, or monitoring the binding between the polypeptide and the antibody. Methods of detecting binding between two entities are known in the art, and include FRET (fluorescence resonance energy transfer), surface plasmon resonance, etc.

Standard laboratory techniques such as immunoblotting as described above can be used to detect altered levels of PRL-1 and PRL-3 protein, as compared with untreated cells in the same cell population.

Gene expression may also be determined by detecting changes in post-translational processing of PRL-1 and PRL-3 polypeptides or post-transcriptional modification of PRL-1 and PRL-3 nucleic acids. For example, differential phosphorylation of PRL-1 and PRL-3 polypeptides, the cleavage of PRL-1 and PRL-3 polypeptides or alternative splicing of PRL-1 and PRL-3 RNA, and the like may be measured. Levels of expression of gene products such as PRL-1 and PRL-3 polypeptides, as well as their post-translational modification, may be detected using proprietary protein assays or techniques such as 2D polyacrylamide gel electrophoresis.

Assay techniques that can be used to determine levels of PRL-1 and PRL-3 protein in a sample derived from a host are well-known to those of skill in the art. Antibodies can be assayed for immunospecific binding by any method known in the art.

The immunoassays which can be used include but are not limited to competitive and non-competitive assay systems using techniques such as western blots, radioimmunoassays, ELISA, sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such assays are routine in the art (see, for example, Ausubel et al., eds, 1994, *Current Protocols in Molecular Biology*, Vol. 1, John Wiley & Sons, Inc., New York, which is incorporated by reference herein in its entirety).

The specimen may be assayed for polypeptides/proteins by immunohistochemical and immunocytochemical staining (see generally Stites and Terr, Basic and Clinical Immunology, Appleton and Lange, 1994), ELISA, RIA, immunoblots, Western blotting, immunoprecipitation, functional assays and protein truncation test. Other assay methods include radioimmunoassays, competitive-binding assays, Western Blot analysis and ELISA assays.

ELISA assays are well known to those skilled in the art. Both polyclonal and monoclonal antibodies may be used in the assays. Where appropriate other immunoassays, such as radioimmunoassays (RIA) may be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Diagnostic Kits

We also provide diagnostic kits for detecting cancer in an individual, or susceptibility to cancer in an individual.

The diagnostic kit may comprise means for detecting expression, amount or activity of PRL-1 or PRL-3 in the individual, by any means as described in this document. The diagnostic kit may therefore comprise any one or more of the following: an anti-PRL antibody, an antibody capable of binding to the same epitope as monoclonal antibody 269, 223 or 318, monoclonal antibody 269, an antibody comprising a variable region of antibody 269, or a humanised monoclonal antibody 269; monoclonal antibody 223, an antibody comprising a variable region of antibody 223, or a humanised monoclonal antibody 223; monoclonal antibody 318, an antibody comprising a variable region of antibody 318, or a humanised monoclonal antibody 318.

The diagnostic kit may comprise instructions for use, or other indicia. The diagnostic kit may further comprise means for treatment or prophylaxis of breast cancer, such as any of the compositions described in this document, or any means known in the art for treating breast cancer. In particular, the diagnostic kit may comprise an anti-PRL1 or anti-PRL3 antibody as described, for example obtained by screening.

Prophylactic and Therapeutic Methods

We disclose methods of treating an abnormal conditions, such as cancer, related to excessive amounts of PRL-1 and PRL-3 expression or activity. Methods of preventing cancer (i.e., prophylaxis) also suitably employ the same or similar approaches.

In general terms, our methods involve manipulation of cancer cells, by modulating (such as down-regulating) the expression, amount or activity of PRL-1 and PRL-3 in the cell. The methods may involve destroying or eradicating cancer cells. The cancer cells may comprise PRL-1 and/or PRL-3 expressing cancer cells. The cancer cells may be ones which over-express PRL-1 and/or PRL-3, compared to non-cancerous cells. Our methods may comprise exposing a patient to an anti-PRL antibody, such as an anti-PRL-1 antibody or an anti-PRL-3 antibody, or both. The anti-PRL-1 antibody may comprise a humanised anti-PRL-1 antibody; likewise, the anti-PRL-3 antibody may comprise a humanised anti-PRL-3 antibody.

The cancer cells may be from PRL-1 and/or PRL-3 positive cancer patients. Thus, our methods may comprise eradicating PRL-1 and/or PRL-3-over-expressing cancer cells from PRL-3/-1-positive cancer patients.

Our methods may therefore comprise eradicating PRL-1 and/or PRL-3 over-expressing cells from PRL-3/-1-positive cancer patients using PRL-3/-1 humanised antibodies.

A step of detecting modulated PRL-1 and PRL-3 expression, amount or activity in a cell may be conducted before or after the manipulation step. The detection step may detect up-regulated or down-regulated PRL-1 and PRL-3 expression, amount or activity. Any of the methods of modulating or down-regulating PRL-1 and PRL-3, as described in detail elsewhere in this document, may be used.

In particular, the method may comprise exposing the cell to an anti-PRL-1 or anti-PRL-3 antibody capable of specifically binding to PRL-1 or PRL-3. Anti-PRL antibodies and methods of administering them are described in detail elsewhere in this document.

According to our methods, the cancer cell becomes non-cancerous or the invasive or metastatic cancer cell becomes non-invasive or non-metastatic as a result of the manipulation. The cancer may in particular comprise a cancer such as an invasive or metastatic cancer selected from the group consisting of: colorectal cancer, ovarian cancer, breast cancer, liver cancer, pancreatic cancer, prostate cancer, gastric cancer, lung cancer, penis cancer, cervical cancer, brain cancer, esophageal cancer, bladder carcinoma, kidney renal cell carcinoma, ovary lymphoma and skin melanoma.

As PRL-1 and PRL-3 is associated with aggressiveness and invasiveness of cancer, the level of PRL-1 and PRL-3 may be detected in a cell of an individual with cancer, in a cancer or non-cancer cell, and the aggressiveness of the cancer assessed. A high level of PRL-1 and PRL-3 amount, expression or activity compared with a normal cell indicates an aggressive or invasive cancer, and a stronger or harsher therapy may therefore be required and chosen. Similarly, a lower level may indicate a less aggressive or invasive therapy.

The approaches described here may be used for therapy of any PRL-1 and PRL-3 related disease in general. PRL-1 and PRL-3 related diseases include proliferative diseases and in particular include cancer. For example, a PRL-1 and PRL-3 related disease may include metastatic cancer, invasive cancer or aggressive cancer.

The methods and compositions described here suitably enable an improvement in a measurable criterion in an individual to whom the treatment is applied, compared to one who has not received the treatment.

For this purpose, a number of criteria may be designated, which reflect the progress of cancer or the well-being of the patient. Useful criteria may include tumour size, tumour dimension, largest dimension of tumour, tumour number, presence of tumour markers (such as alpha-feto protein), degree or number of metastates, etc.

Thus, as an example, a treated individual may show a decrease in tumour size or number as measured by an appropriate assay or test. A treated individual may for example show a 1%, 2%, 3%, 4%, 5%, 6%, 7%, 8%, 9%, 10%, 15%, 20%, 25%, 30%, 40%, 50%, 60%, 70%, 80%, 90%, 100% or more decrease in tumour size of a particular tumour, or decrease in tumour number, or both, compared to an individual who has not been treated.

For example, a PRL-1 and PRL-3 related disease may be defined as being "treated" if a condition associated with the disease is significantly inhibited (i.e., by 50% or more) relative to controls. The inhibition may be by at least 75% relative to controls, such as by 90%, by 95% or 100% relative to controls. The condition may comprise cell proliferation, or it may comprise cell cycle time, cell number, cell migration, cell invasiveness, tumour formation, tumour metastasis, tumour spread, etc. By the term "treatment" we mean to also include prophylaxis or alleviation of cancer.

The term proliferative disorder is used herein in a broad sense to include any disorder that requires control of the cell cycle. In particular, a proliferative disorder includes malignant and pre-neoplastic disorders. The methods and compositions described here are especially useful in relation to treatment or diagnosis of adenocarcinomas such as: small cell lung cancer, and cancer of the kidney, uterus, prostrate, bladder, ovary, colon and breast. For example, malignancies which may be treatable include acute and chronic leukemias, lymphomas, myelomas, sarcomas such as Fibrosarcoma, myxosarcoma, liposarcoma, lymphangioendotheliosarcoma, angiosarcoma, endotheliosarcoma, chondrosarcoma, osteogenic sarcoma, chordoma, lymphangiosarcoma, synovioma, mesothelioma, leimyosarcoma, rhabdomyosarcoma, colon carcinoma, ovarian cancer, prostate cancer, pancreatic cancer, breast cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, choriocarcinoma, renal cell carcinoma, hepatoma, bile duct carcinoma seminoma, embryonal carcinoma, cervical cancer, testicular tumour, lung carcinoma, small cell lung carcinoma, bladder carcinoma, epithelial carcinoma, glioma, astrocytoma, ependymoma, pinealoma, hemangioblastoma, acoustic neuoma, medulloblastoma, craniopharyngioma, oligodendroglioma, menangioma, melanoma, neutroblastoma and retinoblastoma.

The antibody approach to therapy involving use of anti-PRL antibodies may be combined with other approaches for therapy of such disorders including expression of anti-sense constructs directed against PRL-1 and PRL-3 polynucleotides as described here, and administering them to tumour cells, to inhibit gene function and prevent the tumour cell from growing or progressing.

Anti-sense constructs may be used to inhibit gene function to prevent growth or progression in a proliferative cell. Anti-sense constructs, i.e., nucleic acid, such as RNA, constructs complementary to the sense nucleic acid or mRNA, are described in detail in U.S. Pat. No. 6,100,090 (Monia et al.), and Neckers et al., 1992, *Crit Rev Oncog* 3(1-2):175-231, the teachings of which document are specifically incorporated by reference.

In a particular example, cancer may be treated or prevented by reducing the amount, expression or activity of PRL-1 and PRL-3 in whole or in part, for example by siRNAs capable of binding to and destroying PRL-1 and PRL-3 mRNA.

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., *Nature* 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai" file.

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the PRL-1 and PRL-3 nucleic acid sequence.

Alternatively, double-stranded (ds) RNA is a powerful way of interfering with gene expression in a range of organisms that has recently been shown to be successful in mammals (Wianny and Zernicka-Goetz, 2000, *Nat Cell Biol* 2:70-75). Double stranded RNA corresponding to the sequence of a PRL-1 and PRL-3 polynucleotide can be introduced into or expressed in oocytes and cells of a candidate organism to interfere with PRL-1 and PRL-3 activity.

Other methods of modulating PRL-1 and PRL-3 gene expression are known to those skilled in the art and include dominant negative approaches. Again, these may be combined with antibody therapy using anti-PRL antibodies. Thus, another approach is to use non-functional variants of PRL-1 and PRL-3 polypeptide in this document that compete with the endogenous gene product resulting in inhibition of function.

PRL-1 and PRL-3 gene expression may also be modulated by as introducing peptides or small molecules which inhibit gene expression or functional activity. Such peptides or small molecules may be administered in combination with anti-PRL antibodies for the treatment of cancer such as metastatic cancer.

Thus, compounds identified by assays as binding to or modulating, such as down-regulating, the amount, activity or expression of PRL-1 and PRL-3 polypeptide may be administered to tumour or proliferative cells to prevent the function of PRL-1 and PRL-3 polypeptide. Such a compound may be administered along with a pharmaceutically acceptable carrier in an amount effective to down-regulate expression or activity PRL-1 and PRL-3, or by activating or down-regulating a second signal which controls PRL-1 and PRL-3 expression, activity or amount, and thereby alleviating the abnormal condition.

Alternatively, gene therapy may be employed to control the endogenous production of PRL-1 and PRL-3 by the relevant cells such as cancer cells in the subject. For example, a polynucleotide encoding a PRL-1 and PRL-3 siRNA or a portion of this may be engineered for expression in a replication defective retroviral vector, as discussed below. The retroviral expression construct may then be isolated and introduced into a packaging cell transduced with a retroviral plasmid vector containing RNA encoding an anti-PRL-1 and PRL-3 siRNA such that the packaging cell now produces infectious viral particles containing the sequence of interest. These producer cells may be administered to a subject for engineering cells in vivo and regulating expression of the PRL-1 and PRL-3 polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

In some embodiments, the level of PRL-1 and PRL-3 is decreased in a cancer cell. Furthermore, in such embodiments, treatment may be targeted to, or specific to, such cancer cells. The expression of PRL-1 and PRL-3 may be specifically decreased only in diseased cells (i.e., those cells which are cancerous), and not substantially in other non-diseased cells. In these methods, expression of PRL-1 and PRL-3 may be not substantially reduced in other cells, i.e., cells which are not cancer cells. Thus, in such embodiments, the level of PRL-1 and PRL-3 remains substantially the same or similar in non-cancer cells in the course of or following treatment.

Polypeptide Sequences

It will be understood that polypeptide sequences disclosed here are not limited to the particular sequences set forth in this document, but also include homologous sequences obtained from any source, for example related cellular homologues, homologues from other species and variants or derivatives thereof, provided that they have at least one of the biological activities of an anti-PRL antibody, as the case may be.

This disclosure therefore encompasses variants, homologues or derivatives of the amino acid sequences set forth in this document, as well as variants, homologues or derivatives of the amino acid sequences encoded by the nucleotide sequences disclosed here. Such sequences are generally referred to as a "anti-PRL antibody" sequence.

Biological Activities

In some embodiments, the sequences comprise at least one biological activity of an anti-PRL antibody, as the case may be.

The biological activity may comprise an immunological activity. The anti-PRL antibody may comprise an identical or similar immunological activity as compared to antibody 269, 223 ort 318, or their humanised versions. By "immunological activity" we mean the capability of the anti-PRL antibody, to induce a specific immune response in appropriate animals or cells on binding with a PRL-1 or PRL-3 antigen.

The biological activity may comprise antigen binding activity. The anti-PRL antibody may bind to PRL-1 or an epitope thereof. The anti-PRL antibody may bind to the same epitope bound by antibody 269. The anti-PRL antibody may bind to PRL-3 or an epitope thereof. The anti-PRL antibody may bind to the same epitope bound by antibody 223 or the same epitope bound by antibody 318.

The anti-PRL antibody may bind to the antigen or epitope with the same, a reduced or elevated affinity or avidity. For example, the anti-PRL antibody may bind to the antigen or epitope with at least 10%, such as 20%, such as 30%, 40% 50%, 60%, 70%, 80%, 90% or more, affinity or avidity compared to the cognate antibody, e.g., 269, 223 or 318 or their humanised counterparts, as the case may be.

The activity may include inhibition of cancer activity as for example measured by reduction of tumour size or tumour number, or inhibition of metastatic activity, such as for example measured by the assays described in the Examples. The reduction or inhibition may be conveniently assayed by causing carcinogenesis in a test animal, administering the anti-PRL antibody to the animal and determining an effect of the anti-PRL antibody as compared to a similar control animal that has not been so treated. The Examples describe such an assay in detail.

The anti-PRL antibody may have tumour inhibition or metastasis inhibition activity that is the same as, reduced from, or elevated from, the cognate antibody. For example, the anti-PRL antibody may be at least 10%, such as 20%, such as 30%, 40% 50%, 60%, 70%, 80%, 90% or more, effective compared to the cognate antibody, e.g., 269, 223 or 318 or their humanised counterparts, as the case may be. By this we mean that, say, if the cognate antibody is capable of reducing tumour number by 90% (see the Examples), the anti-PRL antibody may be capable of reducing tumour number by 90%, 85%, 80%, 75%, 70%, 65%, 60%, 55%, 50%, 45%, 40%, 35%, 30%, etc, as compared to an untreated animal.

Other assays that detect antibody events can also be used, instead of, or in addition to, the assays described.

Homologues

The anti-PRL antibody polypeptides disclosed include homologous sequences obtained from any source, for example related viral/bacterial proteins, cellular homologues and synthetic peptides, as well as variants or derivatives thereof. Thus polypeptides also include those encoding homologues of anti-PRL antibody from other species including animals such as mammals (e.g. mice, rats or rabbits), in particular humans.

In the context of the present document, a homologous sequence or homologue is taken to include an amino acid sequence which is at least 60, 70, 80 or 90% identical, such as at least 95 or 98% identical at the amino acid level over at least 30, such as 50, 70, 90 or 100 amino acids with a relevant polypeptide sequence, for example as shown in the sequence listing herein. In the context of this document, a homologous sequence is taken to include an amino acid sequence which is at least 15, 20, 25, 30, 40, 50, 60, 70, 80 or 90% identical, such as at least 95 or 98% identical at the amino acid level, such as over at least 15, 25, 35, 50 or 100, such as 200, 300, 400 or 500 amino acids with the sequence of a relevant polypeptide. Although homology can also be considered in terms of similarity (i.e. amino acid residues having similar chemical properties/functions), in the context of the present document homology may be expressed in terms of sequence identity. The sequence identity may be determined relative to the entirety of the length the relevant sequence, i.e., over the entire length or full length sequence of the relevant gene, for example.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, the default values may be used when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). The GCG Bestfit program may be used.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package, or in the case of other software, the default matrix, such as BLOSUM62, may be used.

Once the software has produced an optimal alignment, it is possible to calculate % homology, such as % sequence identity. The software typically does this as part of the sequence comparison and generates a numerical result.

Variants and Derivatives

The terms "variant" or "derivative" in relation to the amino acid sequences as described here includes any substitution of, variation of, modification of, replacement of, deletion of or addition of one (or more) amino acids from or to the sequence. The resultant amino acid sequence may retain substantially the same activity as the unmodified sequence, such as having at least the same activity as the anti-PRL antibody polypeptides shown in this document, for example in the sequence listings. Thus, the key feature of the sequences—namely ability to bind to PRL polypeptides or tumour reduction activity, as described elsewhere—may be retained.

Polypeptides having the amino acid sequence shown in the Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Amino acid substitutions may include the use of non-naturally occurring analogues, for example to increase blood plasma half-life of a therapeutically administered polypeptide.

Natural variants of anti-PRL antibodies are likely to comprise conservative amino acid substitutions. Conservative substitutions may be defined, for example according to the Table below. Amino acids in the same block in the second column such as those in the same line in the third column may be substituted for each other:

| | Fragments | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Polypeptides disclosed here and useful as markers also include fragments of the above mentioned full length polypeptides and variants thereof, including fragments of the sequences set out in the sequence listings.

Polypeptides also include fragments of the full length sequence of any of the anti-PRL antibody polypeptides. Fragments may comprise at least one epitope. Methods of identifying epitopes are well known in the art. Fragments will typically comprise at least 6 amino acids, such as at least 10, 20, 30, 50 or 100 or more amino acids.

Polypeptide fragments of the anti-PRL antibody proteins and allelic and species variants thereof may contain one or more (e.g. 5, 10, 15, or 20) substitutions, deletions or insertions, including conserved substitutions. Where substitutions, deletion and/or insertions occur, for example in different species, such as less than 50%, 40% or 20% of the amino acid residues depicted in the sequence listings are altered.

Anti-PRL antibody and their fragments, homologues, variants and derivatives, may be made by recombinant means.

However, they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His (SEQ ID NO: 40), GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be such that it will not hinder the function of the protein of interest sequence. Proteins may also be obtained by purification of cell extracts from animal cells.

The anti-PRL antibody polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A anti-PRL antibody variant, homologue, fragment or derivative may also be in a substantially purified form, in which case it will generally comprise the protein in a preparation in which more than 90%, e.g. 95%, 98% or 99% of the protein in the preparation is a protein.

The anti-PRL antibody polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

The anti-PRL antibody polypeptides, variants, homologues, fragments and derivatives disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The anti-PRL antibody polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the anti-PRL antibody polypeptides, variants, homologues, fragments and derivatives disclosed here are expressed may be used in assay systems to identify candidate substances which interfere with or enhance the functions of the polypeptides in the cell.

Polynucleotide Sequences

The variable regions, monoclonal antibody sequences and humanised antibody sequences may comprise polynucleotides. These may comprise DNA or RNA.

They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present document, it is to be understood that the polynucleotides described herein may be modified by any method available in the art. Such modifications may be carried out in order to enhance the in vivo activity or life span of polynucleotides.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

Variants, Derivatives and Homologues

The terms "variant", "homologue" or "derivative" in relation to a nucleotide sequence described in this document include any substitution of, variation of, modification of, replacement of, deletion of or addition of one (or more) nucleotides from or to the sequence. The resulting sequence may be capable of encoding a polypeptide which has PRL binding activity as described elsewhere in this document.

As indicated above, with respect to sequence identity, a "homologue" has such as at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to a relevant sequence.

There may be at least 95% identity, such as at least 96% identity, such as at least 97% identity, such as at least 98% identity, such as at least 99% identity. Nucleotide homology comparisons may be conducted as described above. A sequence comparison program such as the GCG Wisconsin Bestfit program described above may be used for this purpose. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, such as 269, 223 and 318 variable region, antibody and humanised antibody or any variant, fragment or derivative thereof, or to the complement of any of the above. Nucleotide sequences may be at least 15 nucleotides in length, such as at least 20, 30, 40 or 50 nucleotides in length.

The term "hybridisation" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, such as at least 80 or 90% and such as at least 95% or 98% homologous to the corresponding nucleotide sequences presented herein over a region of at least 20, such as at least 25 or 30, for instance at least 40, 60 or 100 or more contiguous nucleotides.

The term "selectively hybridisable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with $^{32}$P.

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical polynucleotide sequences while an intermediate (or low) stringency hybridisation can be used to identify or detect similar or related polynucleotide sequences.

We disclose nucleotide sequences that can hybridise to a nucleic acid, or a fragment, homologue, variant or derivative thereof, under stringent conditions (e.g. 65° C. and 0.1×SSC {1×SSC=0.15 M NaCl, 0.015 M Na$_3$ Citrate pH 7.0}).

Where a polynucleotide is double-stranded, both strands of the duplex, either individually or in combination, are encompassed by the present disclosure. Where the polynucleotide is single-stranded, it is to be understood that the complementary sequence of that polynucleotide is also disclosed and encompassed.

Polynucleotides which are not 100% homologous to the sequences disclosed here but fall within the disclosure can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the disclosed sequences under conditions of medium to high stringency.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, such as at least 20, for example at least 25, 30 or 40 nucleotides in length, and are also encompassed by the term polynucleotides as used herein. Fragments may be less than 500, 200, 100, 50 or 20 nucleotides in length.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

PRL Polypeptides and Nucleic Acids

PRL-1 and PRL-3 polypeptide homologues, variants, derivatives and fragments may be defined similarly, as set out in the previous paragraphs.

Where the context permits, a reference to PRL-1 polypeptide should be taken to include reference to a PRL-1 polypeptide homologue, variant, derivative or fragment. Similarly, a reference to PRL-3 polypeptide should be taken to include reference to a PRL-3 polypeptide homologue, variant, derivative or fragment.

Similarly, where the context permits, a reference to PRL-1 nucleic acid should be taken to include reference to a PRL-1 nucleic acid homologue, variant, derivative or fragment. Similarly, a reference to PRL-3 polypeptide should be taken to include reference to a PRL-3 nucleic acid homologue, variant, derivative or fragment.

Anti-PRL Antibody Production

The anti-PRL antibody can be produced by recombinant DNA methods or synthetic peptide chemical methods that are well known to those of ordinary skill in the art.

By way of example, the anti-PRL antibody may be synthesized by techniques well known in the art, as exemplified by "Solid Phase Peptide Synthesis: A Practical Approach" E. Atherton and R. C. Sheppard, IRL Press, Oxford England. Similarly, multiple fragments can be synthesized which are subsequently linked together to form larger fragments. These synthetic peptide fragments can also be made with amino acid substitutions at specific locations in order to test for activity in vitro and in vivo.

The anti-PRL antibody can be synthesized in a standard microchemical facility and purity checked with HPLC and mass spectrophotometry. Methods of peptide synthesis, HPLC purification and mass spectrophotometry are commonly known to those skilled in these arts.

The anti-PRL antibody may also be expressed under in vitro and in vivo conditions in a transformed host cell into which has been incorporated the DNA sequences described here (such as variable sequences) or allelic variations thereof and which can be used in the prevention and/or treatment of cancer related diseases.

The term "vector" includes expression vectors and transformation vectors. The term "expression vector" means a construct capable of in vivo or in vitro expression. The term "transformation vector" means a construct capable of being transferred from one species to another.

Vectors which may be used for expression include recombinant viral vectors, in particular recombinant retroviral vectors (RRV) such as lentiviral vectors, adenoviral vectors including a combination of retroviral vectors.

The term 'recombinant retroviral vector" (RRV) refers to a vector with sufficient retroviral genetic information to allow packaging of an RNA genome, in the presence of packaging components, into a viral particle capable of infecting a target cell. Infection of the target cell includes reverse transcription and integration into the target cell genome. The RRV carries non-viral coding sequences which are to be delivered by the vector to the target cell. An RRV is incapable of independent replication to produce infectious retroviral particles within the final target cell. Usually the RRV lacks a functional gag pol and/or env gene and/or other genes essential for replication. Vectors which may be used include recombinant pox viral vectors such as fowl pox virus (FPV), entomopox virus, vaccinia virus such as NYVAC, canarypox virus, MVA or other non-replicating viral vector systems such as those described for example in WO9530018.

Pox viruses may be engineered for recombinant gene expression and for the use as recombinant live vaccines in a dual immunotherapeutic approach. The principal rationale for using live attenuated viruses, such as viruses, as delivery vehicles and/or vector based vaccine candidates, stems from their ability to elicit cell mediated immune responses. The viral vectors, as outlined above, are capable of being employed as delivery vehicles and as vector based vaccine candidates because of the immunogenicity of their constitutive proteins, which act as adjuvants to enhance the immune response, thus rendering a nucleotide sequence of interest (NOI) such as a nucleotide sequence encoding an anti-PRL antibody more immunogenic.

The pox virus vaccination strategies have used recombinant techniques to introduce NOIs into the genome of the pox virus. If the NOI is integrated at a site in the viral DNA which is non-essential for the life cycle of the virus, it is possible for the newly produced recombinant pox virus to be infectious, that is to say to infect foreign cells and thus to express the integrated NOI. The recombinant pox virus prepared in this way can be used as live vaccines for the prophylaxis and/or treatment of pathologic and infectious disease and/or cancer.

Other requirements for pox viral vector delivery systems include good immunogenicity and safety. MVA is a replication-impaired vaccinia strain with a good safety record. In most cell types and normal human tissue, MVA does not replicate. Limited replication of MVA is observed in a few transformed cell types such as BHK21 cells. Carroll et al (1997 Vaccine 15: 387-394) have shown that the recombinant MVA is equally as good as conventional recombinant vaccinia vectors at generating a protective CD8+T cell response and is an efficacious alternative to the more commonly used replication competent vaccinia virus. The vaccinia virus strains derived from MVA, or independently developed strains having the features of MVA which make MVA particularly suitable for use in a vaccine, are also suitable for use as a delivery vehicle.

The nucleotide sequence of interest, and of which expression is desired, may operably linked to a transcription unit. The term "transcription unit" as described herein are regions of nucleic acid containing coding sequences and the signals for achieving expression of those coding sequences independently of any other coding sequences. Thus, each transcription unit generally comprises at least a promoter, an optional enhancer and a polyadenylation signal. The term "promoter" is used in the normal sense of the art, e.g. an RNA polymerase binding site. The promoter may contain an enhancer element. The term "enhancer" includes a DNA sequence which binds to other protein components of the transcription initiation complex and thus facilitates the initiation of transcription directed by its associated promoter. The term "cell" includes any suitable organism. The cell may comprise a mammalian cell, such as a human cell.

The term "transformed cell" means a cell having a modified genetic structure. For example, as described here, a cell has a modified genetic structure when a vector such as an expression vector has been introduced into the cell. The term "organism" includes any suitable organism. The organism may comprise a mammal such as a human.

Here the term "transgenic organism" means an organism comprising a modified genetic structure. For example, the organism may have a modified genetic structure if a vector such as an expression vector has been introduced into the organism.

Antibody Expression

We further describe a method comprising transforming a host cell with a or the nucleotide sequences described in this document, such as 269, 223 or 318 variable regions, antibody sequences or humanized antibody sequences.

We also provide a method comprising culturing a transformed host cell—which cell has been transformed with a or the such nucleotide sequences under conditions suitable for the expression of the anti-PRL antibody encoded by said nucleotide sequences.

We further provide a method comprising culturing a transformed host cell—which cell has been transformed with a or the such nucleotide sequences under conditions suitable for the expression of the anti-PRL antibody encoded by said nucleotide sequences; and then recovering said anti-PRL antibody from the transformed host cell culture.

Thus, anti-PRL antibody encoding nucleotide sequences, fusion proteins or functional equivalents thereof, may be used to generate recombinant DNA molecules that direct the expression thereof in appropriate host cells.

By way of example, anti-PRL antibody may be produced in recombinant *E. coli*, yeast or mammalian expression systems, and purified with column chromatography.

In certain circumstances there are advantages of using antibody fragments, rather than whole antibodies. The smaller size of the fragments allows for rapid clearance, and may lead to improve tumour to non-tumour ratios. Fab, Fv, ScFv antibody fragments can all be expressed in and secreted from *E. coli*, thus allowing the production of large amounts of the such fragments.

The nucleotide sequences encoding the anti-PRL antibody may be operably linked to a promoter sequence capable of directing expression of the anti-PRL antibody encoding nucleotide sequences in a suitable host cell. When inserted into the host cell, the transformed host cell may be cultured under suitable conditions until sufficient levels of the anti- PRL antibody are achieved after which the cells may be lysed and the anti-PRL antibody is isolated.

Host cells transformed with the anti-PRL antibody encoding nucleotide sequences may be cultured under conditions suitable for the expression and recovery of the anti-PRL antibody from cell culture. The protein produced by a recombinant cell may be secreted or may be contained intracellularly depending on the sequence and/or the vector used. As will be understood by those of skill in the art, expression vectors containing the Anti-PRL antibody encoding nucleotide sequences can be designed with signal sequences which direct secretion of the anti-PRL antibody encoding nucleotide sequences through a particular prokaryotic or eukaryotic cell membrane. Other recombinant constructions may join the anti-PRL antibody encoding nucleotide sequence to a nucleotide sequence encoding a polypeptide domain which will facilitate purification of soluble proteins (Kroll D J et al (1993) DNA Cell Biol 12:441-5 3', see also the discussion below on vectors containing fusion proteins).

The anti-PRL antibody may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath J (1992) Protein Expr Purif 3-26328 1), protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase (Invitrogen, San Diego, Calif.) between the purification domain and the anti-PRL antibody is useful to facilitate purification.

The nucleotide sequences described here may be engineered in order to alter a the anti-PRL antibody encoding sequences for a variety of reasons, including but not limited to alterations which modify the cloning, processing and/or expression of the gene product. For example, mutations may be introduced using techniques which are well known in the art, e.g., site-directed mutagenesis to insert new restriction sites, to alter glycosylation patterns or to change codon preference.

In another embodiment, a or the natural, modified or recombinant anti-PRL antibody encoding nucleotide sequences may be ligated to a heterologous sequence to encode a fusion protein. By way of example, fusion proteins comprising the anti-PRL antibody or an enzymatically active fragment or derivative thereof linked to an affinity tag such as glutathione-S-transferase (GST), biotin, His6 (SEQ ID NO: 40), ac-myc tag (see Emrich et al 1993 Biocem Biophys Res Commun 197(1): 21220), hemagglutinin (HA) (as described in Wilson et al (1984 Cell 37 767) or a FLAG epitope (Ford et al 1991 Protein Expr Purif April; 2 (2):95-107). May be produced The fused recombinant protein may comprise an antigenic coprotein such as GST, beta-galactosidase or the lipoprotein D from *Haemophillls influenzae* which are relatively large co-proteins, which solubilise and facilitate production and purification thereof. Alternatively, the fused protein may comprise a carrier protein such as bovine serum albumin (BSA) or keyhole limpet haemocyanin (KLH). In certain embodiments, the marker sequence may comprise a hexa-histidine peptide, as provided in the pQE vector (Qiagen Inc) and described in Gentz et al (1989 PNAS 86: 821-824). Such fusion proteins are readily expressable in yeast culture (as described in Mitchell et al 1993 Yeast 5:715-723) and are easily purified by affinity chromatography. A fusion protein may also be engineered to contain a cleavage site located between the nucleotide sequence encoding the anti-PRL antibody and the heterologous protein sequence, so that the anti-PRL antibody may be cleaved and purified away from the heterologous moiety. In another embodiment, an assay for the target protein may be conducted using the entire, bound fusion protein. Alternatively, the co-protein may act as an adjuvant in the sense of providing a generalised stimulation of the immune system. The co-protein may be attached to either the amino or carboxy terminus of the first protein.

Although the presence/absence of marker gene expression suggests that the nucleotide sequence for anti-PRL antibody is also present, its presence and expression should be confirmed. For example, if the anti-PRL antibody encoding nucleotide sequence is inserted within a marker gene sequence, recombinant cells containing the anti-PRL antibody coding regions may be identified by the absence of the marker gene function. Alternatively, a marker gene may be placed in tandem with a anti-PRL antibody encoding nucleotide sequence under the control of a single promoter.

Expression of the marker gene in response to induction or selection usually indicates expression of the anti-PRL antibody as well.

Additional methods to quantitate the expression of a particular molecule include radiolabeling (Melby P C et al 1993 J Immunol Methods 159:235-44) or biotinylating (Duplaa C et al 1993 Anal Biochem 229-36) nucleotides, co amplification of a control nucleic acid. and standard curves onto which the experimental results are interpolated.

Quantitation of multiple samples may be speeded up by running the assay in an ELISA format where the anti-PRL antibody of interest is presented in various dilutions and a spectrophotometric or calorimetric response gives rapid quantitation.

Altered anti-PRL antibody nucleotide sequences which may be made or used include deletions, insertions or substitutions of different nucleotide residues resulting in a nucleotide sequence that encodes the same or a functionally equivalent anti-PRL antibody. By way of example, the expressed anti-PRL antibody may also have deletions, insertions or substitutions of amino acid residues which produce a silent change and result in a functionally equivalent anti-PRL antibody. Deliberate amino acid substitutions may be made on the basis of similarity in polarity, charge. solubility, hydrophobicity, hydrophilicity. and/or the amphipathic nature of the residues as long as the binding affinity of the anti-PRL antibody is retained. For example, negatively charged amino acids include aspartic acid and glutamic acid: positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Gene therapy whereby the anti-PRL antibody encoding nucleotide sequences as described here is regulated in vivo may also be employed. For example, expression regulation may be accomplished by administering compounds that bind to the anti-PRL antibody encoding nucleotide sequences, or control regions associated with the anti-PRL antibody encoding nucleotide sequence or its corresponding RNA transcript to modify the rate of transcription or translation.

By way of example, the anti-PRL antibody encoding nucleotide sequences described here may be under the expression control of an expression regulatory element, usually a promoter or a promoter and enhancer. The enhancer and/or promoter may be preferentially active in a hypoxic or ischaemic or low glucose environment, such that the anti-PRL antibody encoding nucleotide sequences is preferentially expressed in the particular tissues of interest, such as in the environment of a tumour cell or mass. Thus, any significant biological effect or deleterious effect of the anti-PRL antibody encoding nucleotide sequences on the individual being treated may be reduced or eliminated. The enhancer element or other elements conferring regulated expression may be present in multiple copies.

The promoter and/or enhancer may be constitutively efficient, or may be tissue or temporally restricted in their activity. Examples of suitable tissue restricted promoters/enhancers are those which are highly active in tumour cells such as a promoter/enhancer from a MUC1 gene, a CEA gene or a STV antigen gene. Examples of temporally restricted promoters/enhancers are those which are responsive to ischaemia and/or hypoxia, such as hypoxia response elements or the promoter/enhancer of agrp78 or agrp94 gene. The alpha fetoprotein (AFP) promoter is also a tumour-specific promoter. Another promoter-enhancer combination is a human cytomegalovirus (hCMV) major immediate early (MIE) promoter/enhancer combination.

The promoters may be tissue specific. That is, they may be capable of driving transcription of a anti-PRL antibody encoding nucleotide sequences in one tissue while remaining largely "silent" in other tissue types.

The term "tissue specific" means a promoter which is not restricted in activity to a single tissue type but which nevertheless shows selectivity in that they may be active in one group of tissues and less active or silent in another group. A desirable characteristic of such promoters is that they possess a relatively low activity in the absence of activated hypoxia-regulated enhancer elements, even in the target tissue. One means of achieving this is to use "silencer" elements which suppress the activity of a selected promoter in the absence of hypoxia.

The term "hypoxia" means a condition under which a particular organ or tissue receives an inadequate supply of oxygen.

The level of expression of a or the anti-PRL antibody encoding nucleotide sequences under the control of a particular promoter may be modulated by manipulating the promoter region. For example, different domains within a promoter region may possess different gene regulatory activities. The roles of these different regions are typically assessed using vector constructs having different variants of the promoter with specific regions deleted (that is, deletion analysis). This approach may be used to identify, for example, the smallest region capable of conferring tissue specificity or the smallest region conferring hypoxia sensitivity.

A number of tissue specific promoters, described above, may be used. In most instances, these promoters may be isolated as convenient restriction digestion fragments suitable for cloning in a selected vector. Alternatively, promoter fragments may be isolated using the polymerase chain reaction. Cloning of the amplified fragments may be facilitated by incorporating restriction sites at the 5' end of the primers.

Combination Therapy

The anti-PRL antibodies described here may be used in combination with other compositions and procedures for the treatment of diseases.

By way of example, the anti-PRL antibodies may also be used in combination with conventional treatments of diseases such as cancer. For example, a tumor may be treated conventionally with surgery, radiation or chemotherapy combined with a anti-PRL antibody or a anti-PRL antibody may be subsequently administered to the patient to extend the dormancy of micrometastases and to stabilize any residual primary tumor.

The anti-PRL antibody can be delivered with a therapeutically effective agent at the same moment in time and at the same site. Alternatively, the anti-PRL antibody and the therapeutically effective agent may be delivered at a different time and to a different site. The anti-PRL antibody and the therapeutically effective agent may even be delivered in the same delivery vehicle for the prevention and/or treatment of cancer.

Anti-PRL antibodies may be used in combination with cytotoxic agents for the prevention and/or treatment of angiogenesis and/or cancer. Cytotoxic agents such as ricin, linked to anti-PRL antibodies, anti-PRL antibodies antisera, anti-PRL antibodies receptor agonists and antagonists provide a tool for the destruction of cells that express PRL-1 or PRL-3. These cells may be found in many locations, including but not limited to, micrometastases and primary tumours.

Anti-PRL antibodies may be used in combination with a pro-drug activating enzyme in gene therapy. Instead of or as well as being selectively expressed in target tissues, the anti-PRL antibody may be used in combination with another molecule, such as a pro-drug activation enzyme or enzymes which have no significant effect or no deleterious effect until the individual is treated with one or more pro-drugs upon which the enzyme or enzymes act. In the presence of the pro-drug activation enzyme, active treatment of an individual with the appropriate pro-drug leads to enhanced reduction in tumour growth or survival.

A pro-drug activating enzyme may be delivered to a tumour site for the treatment of a cancer. In each case, a suitable pro-drug is used in the treatment of the patient in combination with the appropriate pro-drug activating enzyme. An appropriate pro-drug is administered in conjunction with the vector. Examples of pro-drugs include: etoposide phosphate (with alkaline phosphatase, Senter et al 1988 Proc Natl Acad Sci 85: 48424846); 5-fluorocytosine (with cytosine deaminase, Mullen et al 1994 Cancer Res 54: 1503-1506); Doxorubicin-N-p-hydroxyphenoxyacetamide (with Penicillin-V-Amidase, Kerr et al 1990 Cancer Immunol Immunother 31: 202-206); Para-N-bis(2-chloroethyl) aminobenzoyl glutamate (with carboxypeptidase G2); Cephalosporin nitrogen mustard carbamates (with beta-lactamase); SR4233 (with P450 Reductase); Ganciclovir (with HSV thymidine kinase, Borrelli et al 1988 Proc Natl Acad Sci 85: 7572-7576); mustard pro-drugs with nitro reductase (Friedlos et al 1997 J Med Chem 40: 1270-1275) and Cyclophosphamide (with P450 Chen et a/1996 Cancer Res 56: 1331-1340).

Examples of pro-drug activation enzymes include a thymidine phosphorylase which activates the 5-fluoro-uracil pro-drugs capcetabine and furtulon; thymidine kinase from Herpes Simplex Virus which activates ganciclovir; a cytochrome P450 which activates a pro-drug such as cyclophosphamide to a DNA damaging agent; and cytosine deaminase which activates 5-fluorocytosine. An enzyme of human origin may be used.

Other suitable molecules include those that are of therapeutic and/or diagnostic application such as, but are not limited to: sequences encoding cytokines, chemokines, hormones, antibodies, engineered immunoglobulin-like molecules, a single chain antibody, fusion proteins, enzymes, immune co-stimulatory molecules, immunomodulatory molecules, anti-sense RNA, a transdominant negative mutant of a target protein, a toxin, a conditional toxin, an antigen, a tumour suppressor protein and growth factors, membrane proteins, vasoactive proteins and peptides, anti-viral proteins and ribozymes, and derivatives thereof (such as with an associated reporter group). When included, such coding sequences may be typically operatively linked to a suitable promoter, which may be a promoter driving expression of a ribozyme(s), or a different promoter or promoters, such as in one or more specific cell types.

The molecules may be proteins which are secreted from the cell. Alternatively the molecules are not secreted and are active within the cell. In either event, the molecules may demonstrate a bystander effector or a distant bystander effect; that is the production of the expression product in one cell leading to the killing of additional, related cells, either neighbouring or distant (e.g. metastatic), which possess a common phenotype.

Suitable molecules for use in the treatment or prophylaxis of cancer include proteins (or nucleic acids encoding proteins) which: destroy the target cell (for example a ribosomal toxin), act as: tumour suppressors (such as wild-type p53); activators of anti-tumour immune mechanisms (such as cytokines, co-stimulatory molecules and immunoglobulins); inhibitors of angiogenesis; or which provide enhanced drug sensitivity (such as pro-drug activation enzymes); indirectly stimulate destruction of target cell by natural effector cells (for example, strong antigen to stimulate the immune system or convert a precursor substance to a toxic substance which destroys the target cell (for example a prodrug activating enzyme). Encoded proteins could also destroy bystander tumour cells (for example with secreted antitumour antibody-ribosomal toxin fusion protein), indirectly stimulate destruction of bystander tumour cells (for example cytokines to stimulate the immune system or procoagulant proteins causing local vascular occlusion) or convert a precursor substance to a toxic substance which destroys bystander tumour cells (eg an enzyme which activates a prodrug to a diffusible drug).

Antisense transcripts or ribozymes which interfere with expression of cellular genes for tumour persistence (for example against aberrant myc transcripts in Burkitts lymphoma or against bcr-abl transcripts in chronic myeloid leukemia) may be delivered to enhance cancer cell killing function or metastasis preventing function of the anti-PRL antibodies. The use of combinations of such molecules is also envisaged.

Examples of hypoxia regulatable therapeutic molecules can be found in PCT/GB95/00322 (WO-A-9521927).

Anti-PRL Antibody Conjugates

The targeting of cells expressing PRL-1 or PRL-3 antigen with the anti-PRL antibodies described here facilitates the development of drugs to modulate the activity of cells expressing PRL-1 or PRL-3.

Different anti-PRL antibodies can be synthesized for use in several applications including but not limited to the linkage of a anti-PRL antibody to cytotoxic agents for targeted killing of cells that bind the anti-PRL antibody.

The anti-PRL antibody described here can be coupled to other molecules using standard methods. The amino and carboxyl termini of the anti-PRL antibody may be isotopically and nonisotopically labeled with many techniques, for example radiolabeling using conventional techniques (tyrosine residues—chloramine T. iodogen. lactoperoxidase; lysine residues—Bolton-Hunter reagent). These coupling techniques are well known to those skilled in the art. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

The anti-PRL antibodies may be chemically coupled to isotopes, enzymes, carrier proteins, cytotoxic agents, fluorescent molecules and other compounds for a variety of applications. The efficiency of the coupling reaction is determined using different techniques appropriate for the specific reaction. For example, radiolabeling of an PRL-1 or PRL-3 polypeptide with $^{125}I$ is accomplished using chloramine T and Na$^{125}$I of high specific activity. The reaction is terminated with sodium metabisulfite and the mixture is desalted on disposable columns. The labeled antibody is eluted from the column and fractions are collected. Aliquots are removed from each fraction and radioactivity measured in a gamma counter. In this manner, the unreacted Na$^{125}$I is separated from the labeled PRL-1 or PRL-3 polypeptide. The peptide fractions with the highest specific radioactivity are stored for subsequent use such as analysis of the ability to bind to a anti-PRL antibody.

The use of labelled anti-PRL antibodies with short lived isotopes enables visualization quantitation of PRL-1 or PRL-3 binding sites in vivo using autoradiographic, or modern radiographic or other membrane binding techniques such as positron emission tomography in order to locate tumours with anti-PRL antibody binding sites. This application provides important diagnostic and research tools.

In other embodiments, the anti-PRL antibody may be coupled to a scintigraphic radiolabel, a cytotoxic compound or radioisotope, an enzyme for converting a non-toxic prodrug into a cytotoxic drug, a compound for activating the immune system in order to target the resulting conjugate to a colon tumour, or a cell-stimulating compound. Such conjugates have a "binding portion", which consists of the anti-PRL antibody, and a "functional portion", which consists of the radiolabel, toxin or enzyme.

The antibody may alternatively be used alone in order simply to block the activity of the PRL-1 or PRL-3 antigen, particularly by physically interfering with its binding of another compound.

The binding portion and the functional portion of the conjugate (if also a peptide or polypeptide) may be linked together by any of the conventional ways of cross linking polypeptides, such as those generally described in O'Sullivan et of (Anal. Biochem 1979: 100, 100-108). For example, one portion may be enriched with thiol groups and the other portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether-bonds, for example achieved with m-maleimidobenzoyl-N-hydroxysuccinimide ester, are generally more stable in vivo than disulphide bonds.

Alternatively, if the binding portion contains carbohydrates, such as would be the case for an antibody or some antibody fragments, the functional portion may be linked via the carbohydrate portion using the linking technology in EP 0 088 695.

The functional portion of the conjugate may be an enzyme for converting a non-toxic prodrug into a toxic drug, for example the conjugates of Bagshawe and his colleagues (Bagshawe (1987) Br. 1. Cancer 56, 531; Bagshawe et of (Br. 1. Cancer 1988: 58, 700); WO 88/07378) or cyanide-releasing systems (WO 91/11201).

The functional portion of the anti-PRL antibody conjugate, when the anti-PRL antibody conjugate is used for diagnosis, may comprise or consist of a radioactive atom for scintigraphic studies, for example technetium 99m ($^{99m}$Tc) or iodine-123 ($^{123}$I), or a spin label for nuclear magnetic resonance (nmr) imaging (also known as magnetic resonance imaging, mri), such as iodine-123 again, iodine-313, indium-111, fluorine-19, carbon-13, nitrogen-15, oxygen-17, gadolinium, manganese or iron.

When used in a compound for selective destruction of the tumour, the functional portion of the anti-PRL antibody may comprise a highly radioactive atom, such as iodine-131, rhenium-186, rhenium-188, yttrium-90 or lead-212, which emits enough energy to destroy neighbouring cells, or a cytotoxic chemical compound such as methotrexate, adriamicin, vinca alkaliods (vincristine, vinblastine, etoposide), daunorubicin or other intercalating agents.

The radio- or other labels may be incorporated in the anti-PRL antibody conjugate in known ways. For example, the peptide may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can be attached via a cysteine residue in the peptide. Yttrium-90 can be attached via a lysine residue. The IODOGEN method (Fraker et of (1978) Biochem. Biophys. Res. Commun. 80: 49-57 can be used to incorporate iodine-123. "Monoclonal Antibodies in Immunoscinigraphy" (Chatal, CRC Press 1989) describes other methods in detail.

It may not be necessary for the whole enzyme to be present in the conjugate but, of course, the catalytic portion must be present. So-called "abzymes" may be used, where a anti-PRL antibody is raised to a compound involved in the reaction one wishes to catalyse, usually the reactive intermediate state. The resulting antibody can then function as an enzyme for the reaction.

The conjugate may be purified by size exclusion or affinity chromatography, and tested for dual biological activities. The antigen immunoreactivity may be measured using an enzyme-linked immunosorbent assay (ELISA) with immobilised antigen and in a live cell radio-immunoassay. An enzyme assay may be used for β-glucosidase using a substrate which changes in absorbance when the glucose residues are hydrolysed, such as oNPG (o-nitrophenyl-β-D-glucopyranoside), liberating 2-nitrophenol which is measured spectrophotometrically at 405 nm.

The stability of the conjugate may be tested in vitro initially by incubating at 37° C. in serum, followed by size exclusion FPLC analysis. Stability in vivo can be tested in the same way in mice by analysing the serum at various times after injection of the conjugate. In addition, it is possible to radiolabel the anti-PRL antibody with $^{125}$I, and the enzyme with $^{131}$I before conjugation, and to determine the biodistribution of the conjugate, free anti-PRL antibody and free enzyme in an animal, for example a mouse.

Alternatively, the conjugate may be produced as a fusion compound by recombinant DNA techniques whereby a length of DNA comprises respective regions encoding the two portions of the conjugate either adjacent to one another or separated by a region encoding a linker peptide which does not destroy the desired properties of the conjugate.

Conceivably, two of the functional portions of the compound may overlap wholly or partly. The DNA is then expressed in a suitable host in known ways.

Diagnostic Kits

We also disclose diagnostic methods and kits for detection and measurement of PRL-1 or PRL-3 in biological fluids and tissues, and for localization of PRL-1 or PRL-3 in tissues.

The anti-PRL antibodiess can also be used in a diagnostic method and kit to detect and quantify antibodies capable of binding PRL-1 or PRL-3. These kits may permit detection PRL-1 or PRL-3 which, in certain situations, may indicate the spread of micrometastases by primary tumours in situ. Patients that have such circulating anti-PRL-1 or PRL-3 antibodies may be more likely to develop tumours and cancers, and may be more likely to have recurrences of cancer after treatments or periods of remission.

Kits for measurement of PRL-1 or PRL-3 are also contemplated. The anti-PRL antibodies that possess high titer and specificity can be used to establish easy to use kits for rapid, reliable, sensitive. and specific measurement and localization of PRL-1 or PRL-3 in extracts of plasma, urine, tissues. and in cell culture media.

These assay kits include but are not limited to the following techniques; competitive and non-competitive assays, radioimmunoassay, bioluminescence and chemiluminescence assays, fluorometric assays, sandwich assays, immunoradiometric assays. dot blots, enzyme linked assays including ELISA, microtiter plates, antibody coated strips or dipsticks for rapid monitoring of urine or blood. and immunocytochemistry. For each kit the range, sensitivity, precision, reliability, specificity and reproducibility of the assay are established. Intraassay and interassay variation is established at 20%, 50% and 80% points on the standard curves of displacement or activity.

One example of an assay kit commonly used in research and in the clinic is a radioimmunoassay (RIA) kit. After successful radioiodination and purification of an anti-PRL antibody, the antiserum possessing the highest titer is added at several dilutions to tubes containing a relatively constant amount of radioactivity, such as 10,000 cpm, in a suitable buffer system. Other tubes contain buffer or pre immune serum to determine the non-specific binding. After incubation at 4° C. for 24 hours, protein A is added and the tubes are vortexed, incubated at room temperature for 90 minutes, and centrifuged at approximately 2000-2500 times g at 4° C. to precipitate the complexes of antiserum bound to the labeled anti-PRL antibody. The supernatant is removed by aspiration and the radioactivity in the pellets counted in a gamma counter. The antiserum dilution that binds approximately 10 to 40% of the labeled anti-PRL antibody after subtraction of the non-specific binding is further characterized.

An immunohistochemistry kit may also be used for localization of PRL-1 or PRL-3 in tissues and cells. This immunohistochemistry kit provides instructions, a anti-PRL antibody, and possibly blocking serum and secondary antiserum linked to a fluorescent molecule such as fluorescein isothiocyanate, or to some other reagent used to visualize the primary antiserum. Immunohistochemistry techniques are well known to those skilled in the art.

This immunohistochemistry kit permits localization of PRL-1 or PRL-3 in tissue sections and cultured cells using both light and electron microscopy. It is used for both research and clinical purposes. For example, tumours are biopsied or collected and tissue sections cut with a microtome to examine sites of PRL-1 or PRL-3 production. Such information is useful for diagnostic and possibly therapeutic purposes in the detection and treatment of cancer.

Pharmaceutical Compositions

The anti-PRL antibodies may be effective in treating cancer related diseases.

We disclose a method of treating cancer related disease with an effective amount of a anti-PRL antibody described here. The anti-PRL antibodies may be provided as isolated and substantially purified proteins and protein fragments in pharmaceutically acceptable compositions using formulation methods known to those of ordinary skill in the art.

The anti-PRL antibody may be administered in the form of a pharmaceutical composition. Such a pharmaceutical composition may include a therapeutically effective amount of anti-PRL antibody, together with a suitable excipient, diluent or carrier.

The anti-PRL antibody may in particular be introduced into the circulation of a patient, for example by being injected into a patient via, e.g., a vein.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

These compositions can be administered by standard routes. These include but are not limited to: oral, rectal, ophthalmic (including intravitreal or intracameral), nasal, topical (including buccal and sublingual), intrauterine, vaginal or parenteral (including subcutaneous, intraperitoneal, intramuscular, intravenous, intradermaL intracranial, intratracheal, and epidural) transdermal, intraperitoneal. intracranial, intracerebroventricular, intracerebral, intravaginal, intrauterine, or parenteral (e.g., intravenous, intraspinal, subcutaneous or intramuscular) routes.

The anti-PRL antibody formulations may conveniently be presented in unit dosage form and may be prepared by conventional pharmaceutical techniques. Such techniques include the step of bringing into association the active ingredient and the pharmaceutical carriers) or excipient(s). In general, the formulations are prepared by uniformly and intimately bringing into association the active ingredient with liquid carriers or finely divided solid carriers or both, and then, if necessary, shaping the product.

In addition, the anti-PRL antibodies may be incorporated into biodegradable polymers allowing for sustained release of the compound, the polymers being implanted in the vicinity of where drug delivery is desired, for example, at the site of a tumor or implanted so that the anti-PRL antibody is slowly released systemically. The biodegradable polymers and their use are described, for example, in detail in Brem et of (1. Neurosurg 1991 74:441-446). Osmotic minipumps may also be used to provide controlled delivery of high concentrations of anti-PRL antibodies through cannulae to the site of interest, such as directly into a metastatic growth or into the vascular supply to that tumor.

The anti-PRL antibodies may be linked to cytotoxic agents which are infused in a manner designed to maximize delivery to the desired location. For example, ricin-linked high affinity anti-PRL antibodies are delivered through a cannula into vessels supplying the target site or directly into the target. Such agents are also delivered in a controlled manner through osmotic pumps coupled to infusion cannulae.

Preferred unit dosage formulations are those containing a daily dose or unit, daily sub-dose, as herein above recited, or an appropriate fraction thereof, of the administered ingredient. It should be understood that in addition to the ingredients, particularly mentioned above, the formulations described here may include other agents conventional in the art having regard to the type of formulation in question.

The anti-PRL antibody conjugates may be administered in any suitable way. usually parenterally, for example intravenously or intraperitoneally, in standard sterile, non-pyrogenic formulations of diluents and carriers, for example isotonic saline (when administered intravenously). Once the anti-PRL antibody conjugate has bound to the target cells and been cleared from the bloodstream (if necessary), which typically takes a day or so, the pro-drug is administered, usually as a single infused dose, or the tumour is imaged. If needed, because the anti-PRL antibody conjugate may be immunogenic, cyclosporin or some other immunosuppressant can be administered to provide a longer period for treatment but usually this will not be necessary.

The dosage of the anti-PRL antibody described here will depend on the disease state or condition being treated and other clinical factors such as weight and condition of the human or animal and the route of administration of the compound.

Depending upon the half-life of the anti-PRL antibody in the particular animal or human, the anti-PRL antibody can be administered between several times per day to once a week. It is to be understood that the methods and compositions described here have application for both human and veterinary use. The methods described here contemplate single as well as multiple administrations, given either simultaneously or over an extended period of time.

The timing between administrations of the anti-PRL antibody conjugate and pro-drug may be optimised in a routine way since tumour/normal tissue ratios of conjugate (at least following intravenous delivery) are highest after about 4-6 days, whereas at this time the absolute amount of conjugate bound to the tumour, in terms of percent of injected dose per gram, is lower than at earlier times.

Therefore, the optimum interval between administration of the anti-PRL antibody conjugate and the pro-drug will be a compromise between peak tumour concentration of enzyme and the best distribution ratio between tumour and normal tissues. The dosage of the anti-PRL antibody conjugate will be chosen by the physician according to the usual criteria. At least in the case of methods employing a targeted enzyme such as β-glucosidase and intravenous amygdalin as the toxic pro-drug, 1 to 50 daily doses of 0.1 to 10.0 grams per square meter of body surface area, preferably 1.0-5.0 g/m$^2$ are likely to be appropriate. For oral therapy, three doses per day of 0.05 to 10.0 g, preferably 1.0-5.0 g, for one to fifty days may be appropriate. The dosage of the anti-PRL antibody conjugate will similarly be chosen according to normal criteria, particularly with reference to the type, stage and location of the tumour and the weight of the patient. The duration of treatment will depend in part upon the rapidity and extent of any immune reaction to the anti-PRL antibody conjugate.

Diseases

Anti-PRL antibodies described here, for example in the form of pharmaceutical compositions, may be used in the treatment of cancer.

For the purposes of this document, the term "cancer" can comprise any one or more of the following: acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CML), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary CNS lymphoma, prostate cancer, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and Wilms' tumor.

Anti-PRL antibodies described here, for example in the form of pharmaceutical compositions, can also be used in the treatment of cancer related disorders.

Such disorders include but not limited to: solid tumours; blood born tumours such as leukemias; tumor metastasis; benign tumours, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; coronary collaterals; cerebral collaterals) arteriovenous malformations; ischemic limb angiogenesis; neovascular glaucoma; retrolental fibroplasia; diabetic neovascularisation; *helicobacter* related diseases, fractures, vasculogenesis, hematopoiesis, ovulation, menstruation and placentation.

EXAMPLES

Example 1

Cell Lines: CHO-K1, A2780 and CT26

CHO-K1 cells, A2780 human ovarian cancer cells and CT26 mouse colon cancer cells are purchased from ATCC (Manassas, Va.).

Example 2

Generation of CHO Cell Pools Stably Expressing EGFP-PRL-3 or EGFP-PRL-1

CHO cell pools stably expressing EGFP-PRL-3 or EGFP-PRL-1 are generated as described in a previous study[8]. Briefly, the cells are cultured in RPMI 1640 medium supplemented with 10% fetal bovine serum and selected in 1 mg/ml G418 for 20-30 days. The cells ($10^6$ cells/ml) are then subjected to EGFP sorting by FACS Vantage, SE mode (Becton Dickinson) and re-grown in culture to establish stable cell pools.

Example 3

Generation of AT-3 Cells Stably Expressing EGFP-PRL-3 or AT-1 Cells Stably Expressing EGFP-PRL-1

To obtain EGFP-PRL-3 or EGFP-PRL-1 tumours, 8-week old nude mice (Jackson Labs, USA) are each injected via the tail vein with EGFP-PRL-3- or EGFP-PRL-1-expressing cells ($5\times10^5$). Mice are sacrificed at 3 weeks after the tail vein injection. Lungs carrying EGFP-PRL-3 or EGFP-PRL-1 tumours are removed. EGFP-PRL-tumours are dissected out individually under the fluorescent microscope (Zeiss, M2 Bio Quad). To generate cell lines derived from these tumours, each EGFP-PRL-tumour is washed twice in PBS under sterile conditions. The tumour is cut into tiny pieces and cultured at 37° C. with 5% $CO_2$ with RPMI 1640, 10% FBS and 1% antibiotics (Sigma). AT-3 tumour cell line is derived from the EGFP-PRL-3 tumour; while AT-1 tumour cell line is derived from the EGFP-PRL-1 tumour. The cells are trypsinized and split at a ratio of 1:3 into new dishes. The tumour cell lines homogeneously expressed EGFP-PRL-3 or EGFP-PRL-1 are confirmed by indirect immunofluorescence.

Example 4

Generation of Specific PRL-3 mAbs Clones 223, 318 and PRL-1 mAb Clone 269

These antibodies are generated as follows (see also reference 19): Hybridomas are generated using ClonaCell-HY Hybridoma Cloning Kit from Stemcell Technologies, Inc. (Vancouver, British Columbia, Canada). The procedures are followed according to the manufacturer's directions. Briefly, the following are done: (a) immunization of BALB/c mice with GST-mouse whole PRL-1, or PRL-3 fusion protein, respectively; (b) growth of BALB/c parental myeloma cells SP2/0; (c) preparation of BALB/c mice for spleenocytes from immunized mice; (d) fusion of spleenocytes with SP2/0 cells; and (e) selection and characterizations of the hybridoma clones.

Two control ascites: 1. Ascitic fluid derived from hybridoma 6A7M against human glycophorin A (obtained from ATCC). 2. Ascitic fluid against to GS28 Golgi complex marker.

Example 5

Experimental Metastasis Assay

Reference is made to reference 20. All animal studies have been approved by the Review Board of the Institute of Molecular and Cell Biology, Singapore. We follow the policies from the Animal Facility Center of The Agency for Science, Technology and Research (A* STAR), Singapore[5,8,19]. Nude mice are injected with one million cancer cells via their tail vein on day 1. The treated mice are administrated with PRL-mAbs via tail vein twice a week.

Example 6

Western Blot Analysis

Detailed steps are described in reference 19.

Example 7

Confocal Microscopy and Analysis of EGFP-PRL-3-Expressing Cancer Cells

AT-3, AT-1, or parental CHO cells are grown on cover slips and washed once with PBSCM (PBS containing 1 mM $MgCl_2$ and 1 mM $CaCl_2$). Cells are then fixed in 2.7% paraformaldehyde for 20 min at room temperature (RT, 24° C.). After two more washes with PBSCM, cells are permeabilized for 15 min with 0.12% Saponin in PBSCM (this step is omitted for non-permeabilized cells) and incubated with anti-PRL-3 mAb. The cells are washed gently three times with PBSCM and incubated with anti-mouse IgG conjugated with Texas Red (Sigma) for 4 hours at RT. AT-3 or AT-1 cells are directly visualized with fluorescence microscopy in green. To examine antibodies taken up in live parental CHO cells, cells are first incubated with mouse anti-GS28 antibody at 4° C. for 2 h. The cells are washed gently three times with PBSCM and then fixed in 0.6% paraformaldehyde for 20 min at room temperature (RT, 24° C.). The cells are incubated with anti-mouse IgG conjugated with FITC (Sigma) for 4 hours at RT. To-pro-3 iodide is used to stain the DNA of every parental CHO cell in blue. Confocal imaging is performed with a Zeiss LSM 510 image Browser.

Example 8

Immunohistochemistry (IHC)

Using monoclonal mouse PRL-3 (clone 223 or 318) or mouse PRL-1 (clone 269) antibodies (1:300 dilution) and VECTASTAIN ABC kit-Peroxidases Rabbit IgG PK-4001 (Orton Southgate, Peterborough, England) to perform IHC experiments, we investigated PRL-3 and PRL-1 protein expressions on human colon and breast cancer specimens from Cybrdi (Frederick, Md.). The human low and high density multiple malignant tumour arrays (TS42040704) and (TS43040303) are purchased from BioGenex (San Ramon, Calif.). The formalin-fixed, paraffin-embedded slides are baked at 54° C. for 10 min and then de-waxed in fresh xylene for 5 min (2×). The slides are subjected to rehydration with sequential 100%, 95%, 80%, and 75% Ethanol, PBS (2 min for each change), then in 0.01M sodium citrate pH 6.0 buffer, followed by antigen retrieval 2100-Retriever Pick Cell Laboratories (Amsterdam, North Holland, 1098SM, NL) for 15 min. The slides are cooled for 4 h in the cooker. The slides are washed three times with PBS (5 min each) and transferred into PBS with 0.6% $H_2O_2$ in the dark for 20 min. The slides are washed in PBS several times and treated in PBS-0.2% Tween 20 for 20 min at 24° C. The blocking step and antibodies incubations are performed according to the manufacturer's instructions.

Example 9

An Animal Model Allows Rapid Formation of Aggressive Metastatic Lung Tumours

This Example describes the generation of PRL-overexpressing tumours in mice and provision of an animal model for future PRL-cancer therapy.

Reference is made to FIG. 1.

Firstly, nude mice are used as an in vivo "cell sorter" to select cells with high metastatic activities. $1 \times 10^6$ EGFP-PRL-3- or EGFP-1-expressing CHO cells are injected into the circulation of nude mice via the tail vein. Dozens of metastatic tumours or foci are formed in the lung of each nude mouse at three weeks post-injection.

Secondly, a single such lung metastatic EGFP-PRL-tumour is then dissected out and minced in culture dishes to establish a more aggressive and homogeneous EGFP-PRL-3 expressing metastatic cell line named AT-3 or EGFP-PRL-1 expressing tumour cell line named AT-1.

Thirdly, $1 \times 10^6$ of AT3 or AT1 cells are injected into nude mice again via the tail vein. Fourthly, we divided the mice into untreated or treated groups with different antibodies administrated via tail vein injection on days 3, 6, and 9-post inoculation of the tumour cells.

An animal model in which PRL-3 or PRL-1 over-expressing cells rapidly formed metastatic tumours is designed. With such aggressive metastatic tumours as background, one should be able to observe any suppression of tumourigenicity if treatment with anti-PRL-mAbs is effective.

Our animal model recapitulates the aggressive metastatic activities of PRL-expressing cells and is useful in dissecting metastatic events occurring after invasion or intravasation.

Example 10

PRL-3 mAb or PRL-1 mAb Blocks the Formation of EGFP-PRL-3 or EGFP-PRL-1 Metastatic Lung Tumours with ~90% Efficacy in Mice Four groups of control mice (FIG. 2A, a, untreated; b, PBS-treated; c & d, two unrelated antibodies) showed massive and widespread EGFP-PRL-3 metastatic tumours (~140-150 loci) in their lungs on day 15-post-injection of cells.

Strikingly, the other four groups of mice that received three doses of PRL-3 mAbs in the form of either purified IgG or unpurified ascitic fluid from hybridoma clone 223 (FIG. 2A e and g) or clone 318 (FIG. 2A f and h) showed a dramatic reduction in EGFP-PRL-3-expressing tumours (~15-20 loci) in their lungs.

Figure 2A:
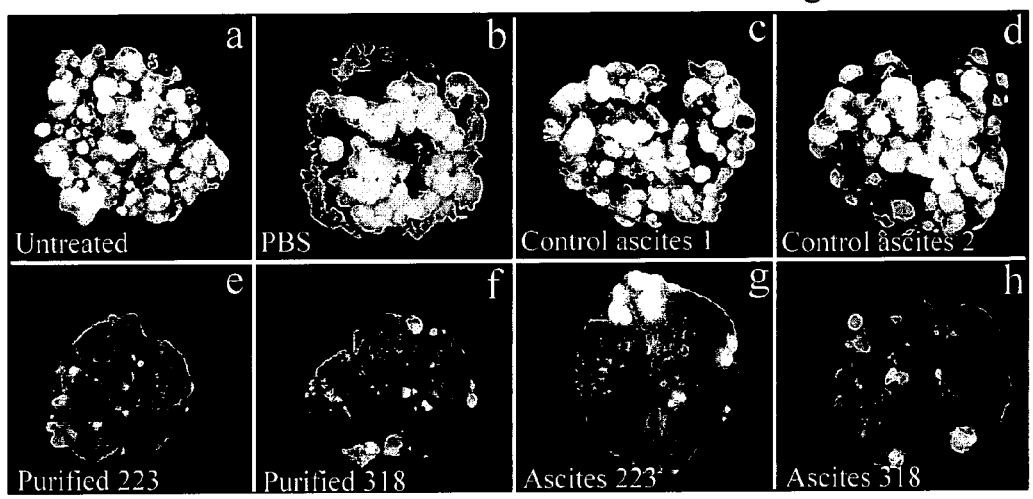
FIG. 2. PRL-3 and PRL-1 mAbs specifically inhibit the formations of their respective metastatic lung tumors. A. $1 \times 10^6$ AT3 cells (described in FIG. 1) are injected into nude mice via the tail vein. Mice are either untreated (a, n=10) or PBS-treated (b, n=10), or treated with two unrelated antibodies (c, n=5; d, n=5). PRL-3 mAb 223 is in the form of purified IgG (e) or ascitic fluid (g); PRL-3 mAb 318 is in the form of purified IgG (f) or ascitic fluid (h) administrated via the tail vein. The different antibodies are injected on days 3, 6, and 9 post-inoculation of AT3 cells. Lungs are dissected out on day 15 post-injection and photographed under fluorescence microscopy to show the GPF-positive metastatic tumours. Images a, b, e, and f are lungs from female mice. Images c, d, g, and h are lungs from male mice. B. The total numbers of tumour in A are quantified in the Y axis as the average of tumour lesions from each group, while the X axis displays the various groups of mice with different treatments. The results from mice injected with AT-3 cells are shown in columns 1-7. The mice injected with AT-1 cells are either treated with PBS or with mAb 269 against PRL-1 (columns 8-9). n=numbers of mice in each group.
Figure 2B:
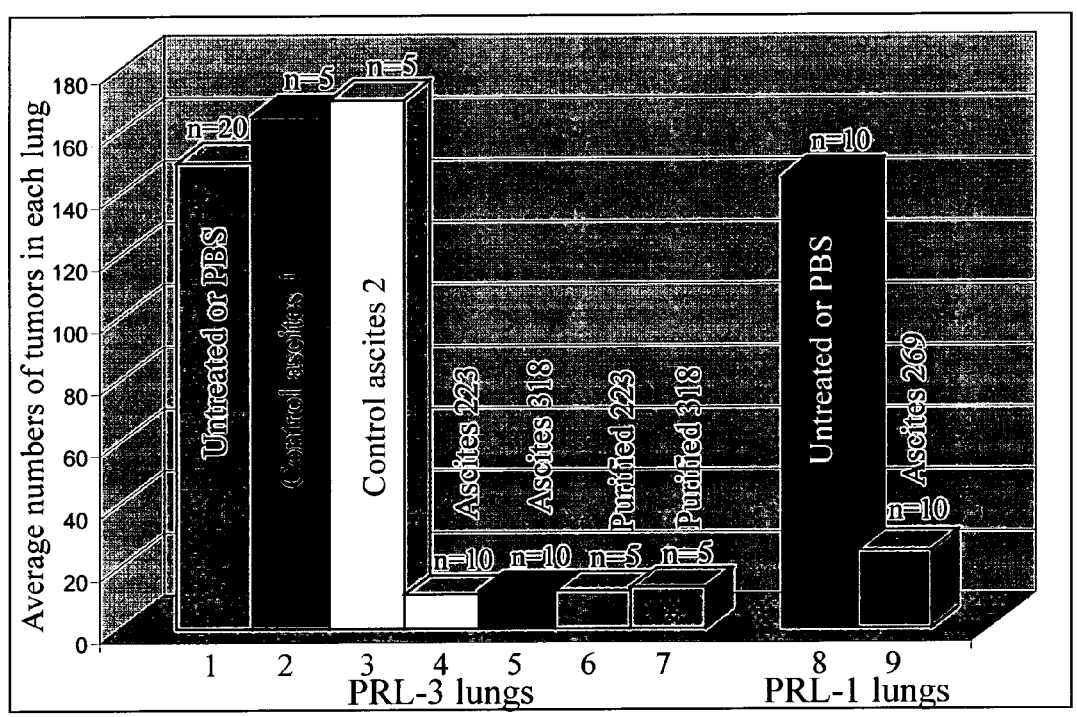

Similarly, the PRL-1 mAb significantly reduced the formation of metastatic tumours derived from the inoculation of EGFP-PRL-1-expressing AT-1 cells (FIG. 2B, lane 9). Overall, mice (n=40) treated with PRL monoclonal antibodies showed inhibition of metastatic lung tumours by ~90% compared to control mice (n=40). PRL-3 mRNA (but not protein) has been detected in the heart[5].

In this regard, it is worth emphasizing that animals treated with the PRL-3 mAb did not exhibit noticeable cardiotoxicity or other undesirable side effects.

Example 11

PRL-1 mAb Specifically Blocks the Formation of PRL-1 (but not PRL-3) Metastatic Tumours while PRL-3 mAb Specifically Blocks the Formation of PRL-3 (but not PRL-1) Metastatic Tumours This Example demonstrates that the effects of the antibodies are specific.

Figure 3:
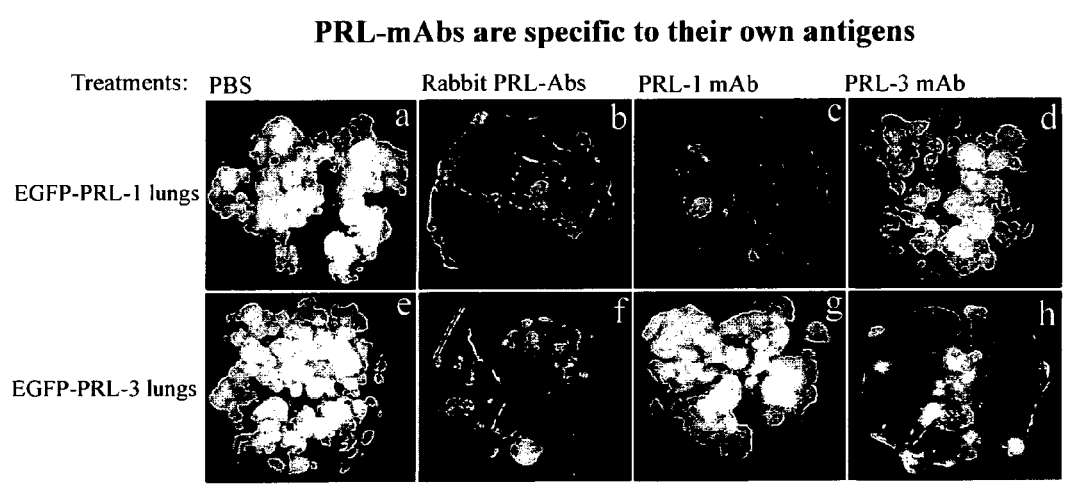
FIG. 3. PRL-1 mAb specifically blocks PRL-1 but not PRL-3 metastatic tumours; while PRL-3 mAb specifically blocks PRL-3 but not PRL-1 metastatic tumours. We injected one million cancer cells (AT-1 or AT-3) either EGFP-PRL-1 or -PRL-3 into each mouse via its tail vein on day 1. Mice are then divided into groups respectively receiving PBS, rabbit PRL antibodies, PRL-1 mAb or PRL-3 mAb via their tail veins on day 3, 6, and 9 post-cancer cell injections. Lungs (panels: a-d) derived from mice carrying AT-1 cancer cells expressing EGFP-PRL-1 or lungs (e-h) derived from mice carrying AT-3 cancer cells expressing EGFP-PRL-3 are dissected out and photographed on day 15. PRL-1 and PRL-3 metastatic tumours in lungs are not blocked by mock-PBS treatment (a, e) but are both effectively blocked by rabbit antibodies (b, f). PRL-1 mAb inhibits the formation of tumours in which PRL-1 is overexpressed (c) but not when PRL-3 is overexpressed (g). Similarly, PRL-3 mAb blocks the formation of metastatic tumours in which PRL-3 is overexpressed (h) but not when PRL-1 is overexpressed (d). Therefore, these individual PRL-mAbs are specific in blocking formation of lung metastatic tumours of cells expressing the target antigen, respectively.

Reference is made to FIG. 3.

We show that formation of lung metastatic tumours by PRL-1- and PRL-3-expressing cells is not blocked by mock-PBS treatment (a, e) but is effectively blocked by rabbit PRL antibodies (b, f) as the rabbit antibodies react with all three PRLs (PRL-1, PRL-2 and PRL-3).

We show PRL-1 mAb blocks the formation of lung metastatic tumours in which PRL-1 is overexpressed (c) but not PRL-3 is overexpressed (g).

Similarly, PRL-3 mAb inhibits (reducing tumour numbers) the formation of lung metastatic tumours in which PRL-3 is overexpressed (h) but not PRL-1 is overexpressed (d).

Example 12

PRL-3 mAbs Effectively Inhibit the Formation of Metastatic Tumours by A2780 Cells that Express Endogenous PRL-3 but not CT26 Cells that do not Express Endogenous PRL-3

The dramatic efficacy of PRL-mAbs therapies depends on targeting cells that have high levels of expression of the EGFP-PRL proteins so far.

We then performed a crucial experiment to assess if the antibodies could block metastasis of cancer cells that naturally express PRL-3 protein. Candidate cancer cell lines that are ideal to be used in this experiment should have two properties: 1. naturally expressed PRL-3 protein. 2. be able to cause metastatic tumour formation in mice rapidly.

We found A2780 human ovarian cancer cell line has these two properties and confirmed that A2780 cells express PRL-3 protein naturally (FIG. 4A, lane 2), which is reported previously[9].

Figure 4A:
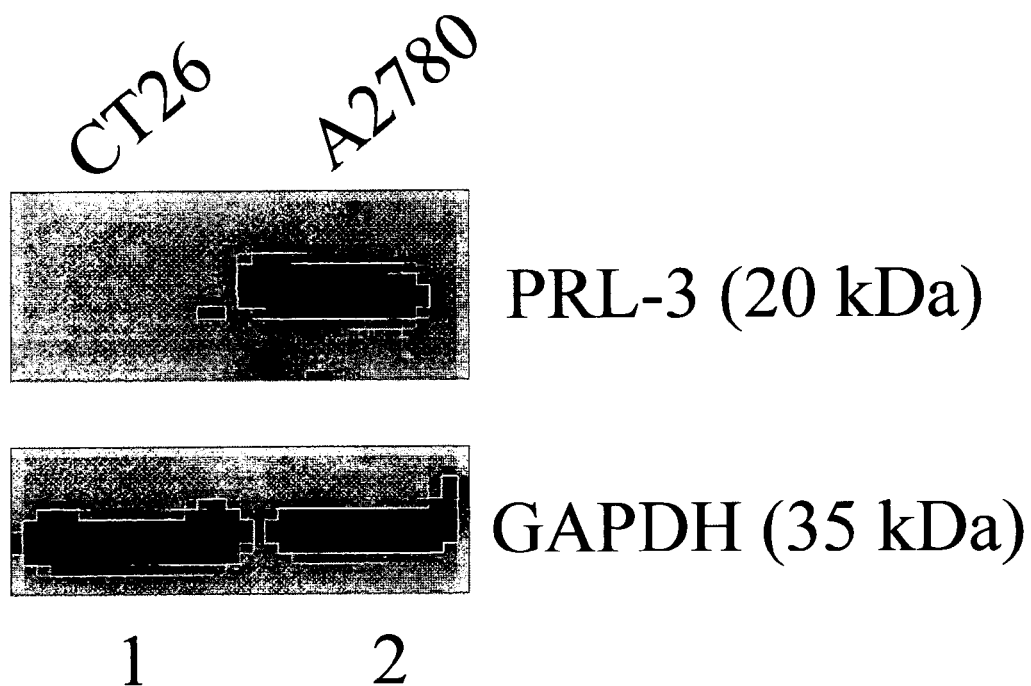
FIG. 4. PRL-3 mAbs effectively block metastatic tumour formation by A2780 PRL-3-positive cancer cells; but have no effect on metastatic tumour formation by CT26 PRL-3 negative cancer cells. A. A2780 but not CT26 cells express endogenous PRL-3. Cell lysates prepared from CT26 mouse colon cancer cell line and A2780 human ovarian cancer cell line are analyzed by western blotting to detect PRL-3. GAPDH is used as a loading control. B. PRL-3 antibody treatment does not affect lung tumour formation of CT26 PRL-3 negative cells at 2-week post cancer cell inoculation. All major tissues are examined for tumour formation. Gross appearances the animals as well as the dissected lungs of treated mice (panel a) and of untreated mice (panel b) are imaged. Extensive tumour formation is observed in all lungs as indicated by black arrows. C. PRL-3 antibody treatment inhibits pathologic appearances and tumour formation of A2780 PRL-3 positive cells in experimental metastasis assay at 1-month post cancer cells inoculation. All major tissues are examined for tumour formation. Gross appearances of the animals and tumours (indicated by black arrows) dissected out from untreated animals are imaged. Tumours are not found in treated mice.
Figure 4B:
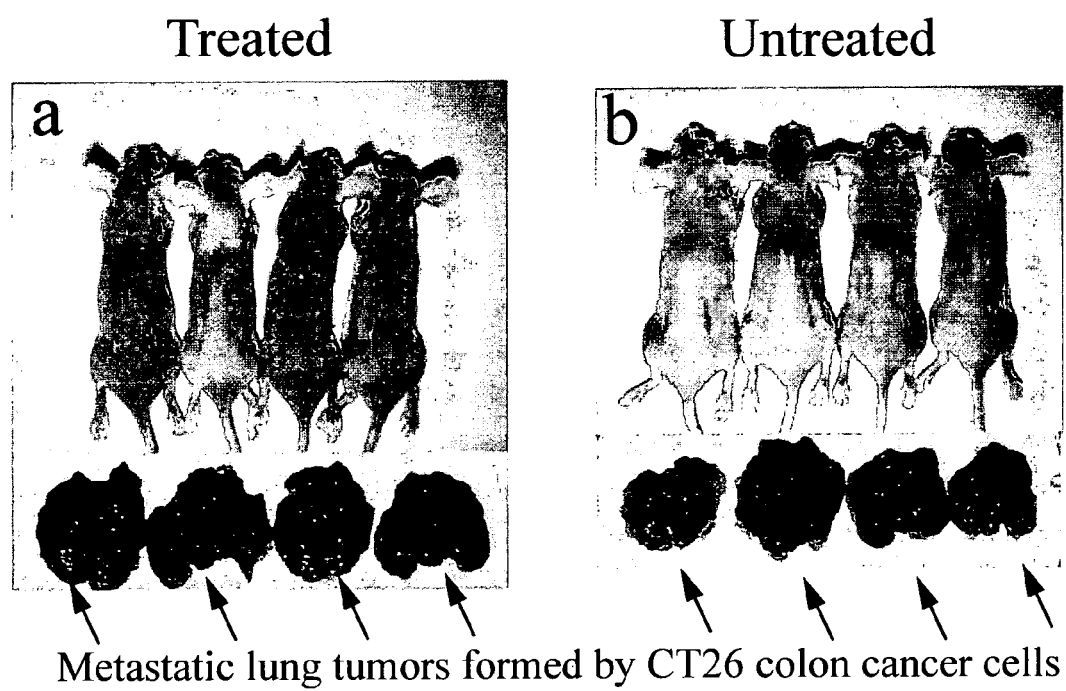

Meanwhile, we identified a mouse colon cancer cell line CT26 that does not express PRL-3 protein (FIG. 4A, lane 1). CT26 cancer cell line is selected as a negative control for this experiment as it has strong metastatic activity in lungs of nude mice at 2-week post inoculation of the cancer cells (FIG. 4B).

Expectedly, no difference is found between treated (FIG. 4B, a) and untreated (FIG. 4B, b) groups of mice receiving CT26 cells, which all show pathologic appearance in weight loss.

Rapid formation of aggressive lung metastatic tumours by CT26 cells is not inhibited by PRL-3 mAbs (FIG. 4B, bottom a) as compared with lungs (FIG. 4B, bottom b) from untreated mice, suggesting that the PRL-mAbs do not inhibit the formation of lung metastatic tumours in which PRL-3 phosphatase is not expressed naturally.

Figure 4C:
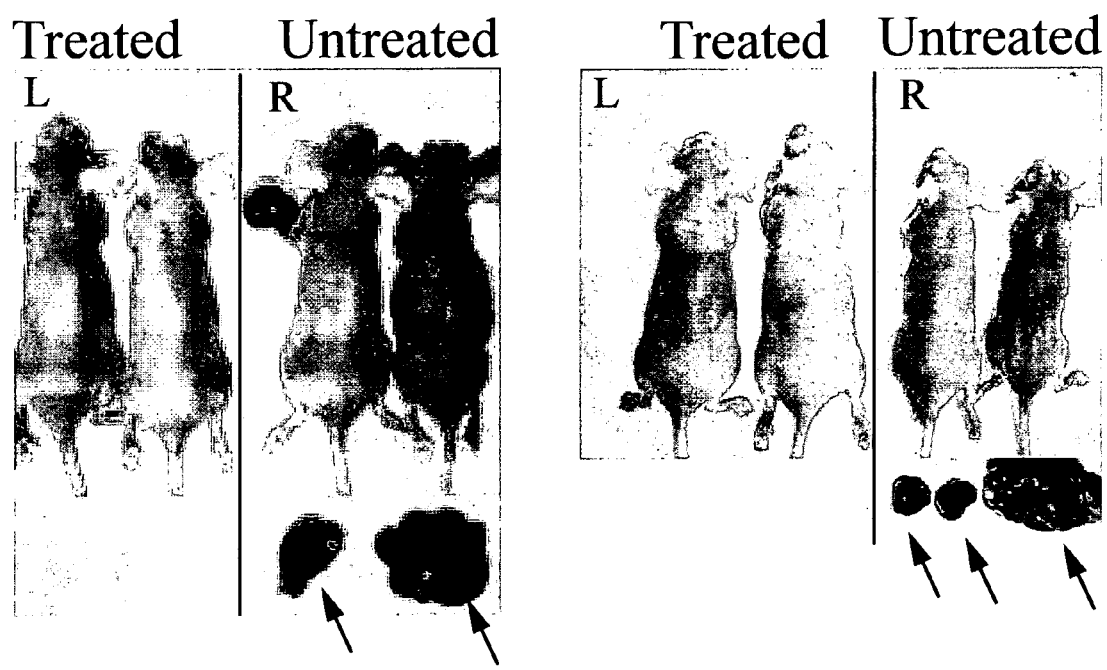

In contrast, significant differences are found between treated and untreated mice at 1-month post-inoculation of A2780 human cancer cells that express endogenous PRL-3 protein. Pathologic appearances (unhealthy and skinny) as well as multiple tumours formed by A2780 PRL-3 positive-cells are observed only in untreated mice (FIG. 4C, R-side) but not in treated mice (FIG. 4C, L-side). The treated mice remain healthy for a prolonged period of time.

These results suggest that PRL-3 mAbs are able to block metastatic tumour formation of cancer cells naturally expressing PRL-3 but has no effect on cancer cells that do not express endogenous PRL-3.

Example 13

PRL-3- or PRL-1-Expressing Cells Taking Up their Respective PRL-Antibodies

The precise mechanism by which anti-PRL antibodies inhibit tumour formation needs to be further investigated. To determine whether tumour cells can take up PRL mAbs, we examined PRL-3 mAb staining using an indirect immunofluorescence assay in non-permeabilized AT-3 cells over-expressing EGFP-PRL-3.

Figure 5A:
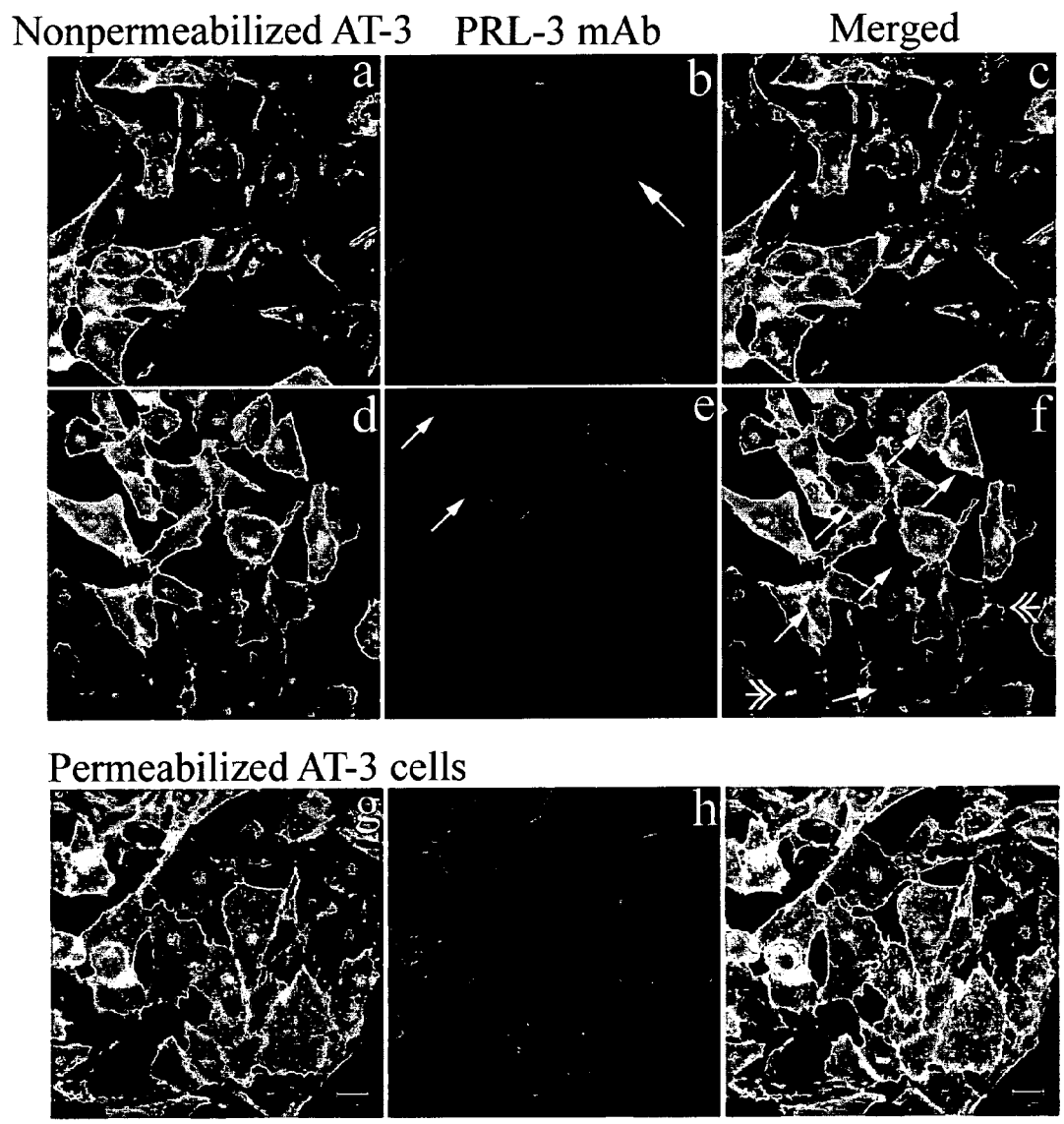
FIG. 5. Antibody uptake in AT-3 cancer cells and parental CHO cells are revealed by indirect immunofluorescence. A, EGFP-PRL-3 is expressed in all non-permeabilized AT-3 cells as detected by EGFP (a, d). A few cells are completely labeled with PRL-3 mAb[19] (white arrows indicated in b, e panels); 40% of non-permeabilized cells are partially labeled in red with the PRL-3 mAbs; the internalized antibody seems to be distributed in a polarized manner at cell edges (single-head arrows indicated in 0 and some in membrane protrusions (double-head arrows indicated in 0; while the remainder of the cells remained unlabeled (c and f cells in green only). B. To-pro-3 iodide is used to stain the DNA of every parental CHO cell in blue. Live cells (10-20%) capable of taking up mouse anti-GS28 are shown in green (a, b, and c). The majority (60-70%) of live cells that are serum-starved overnight are able to take up mouse anti-GS28 shown in green (d, e, and f). White arrows indicate some cells (perhaps in some stages of cell cycle) that are not able to up-take antibody. Bars, 20 µm.

Some non-permeabilized AT-3 cells appeared fully stained with the anti-PRL-3 mAb (FIG. 5A, white arrows indicated in b & e panels). 40% of these cells are partially stained in red, but >50% of the cells are completely unlabeled (FIG. 5A, b, e) compared to permeabilized AT-3 cells showing 100% staining in red with anti-PRL-3 mAb (FIG. 5A, h).

The data indicate that large PRL mAbs are still able to either partially or completely penetrate into non-permeabilized cancer cells.

Analogous results are obtained using an anti-PRL-1 mAb (clone #269) with CHO cells that over-express EGFP-PRL-1 (data not shown).

Figure 5B:
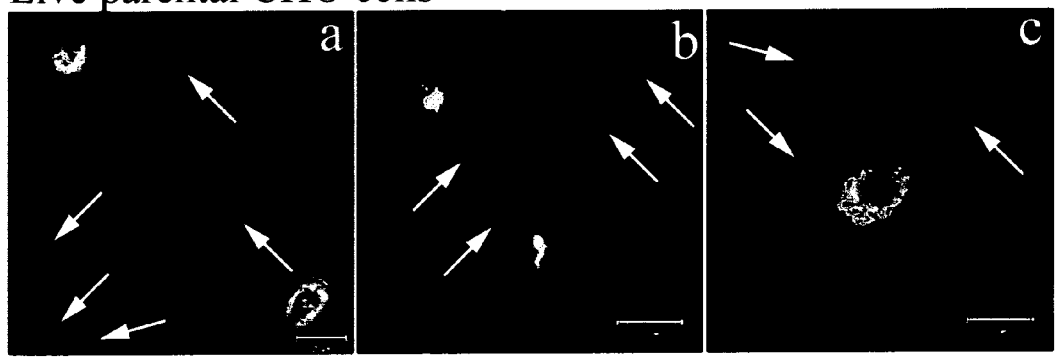
Figure 5B:
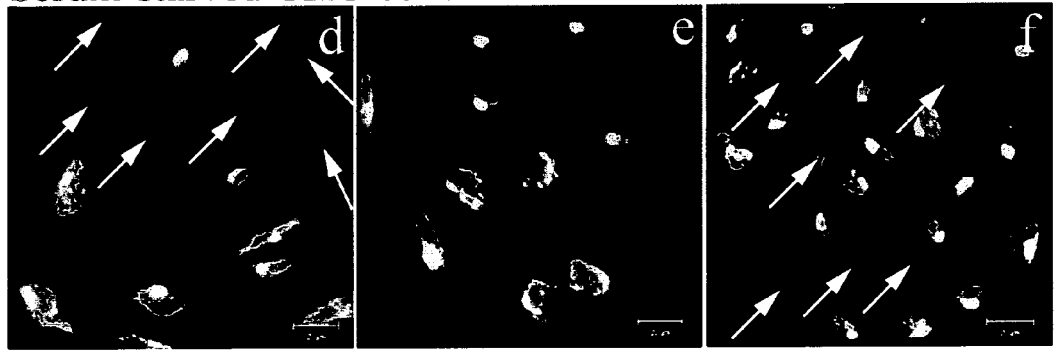

To further confirm the antibody can access into cells internally, we select an antibody against to Golgi apparatus marker (GS28) and show that the GS28 mAb can penetrate into CHO live cells in culture (FIG. 5B a-c). Furthermore, the majority (60-70%) of live cells that are serum-starved overnight shows higher efficacy in taking up mouse anti-GS28 by unknown mechanisms (shown in green FIG. 5B d-f).

To investigate if the up-take of the antibody is a general cell phenomenon or not, three PRL-unrelated antibodies are tested on two other cell lines. These are mouse anti-GS28 and rabbit anti-PTEN antibodies on non-permeabilized human mammary epithelial cells (MCF-10A); and mouse anti-GS28 and rabbit anti-p53 on human breast cancer cells (MCF-7).

Figure 6:
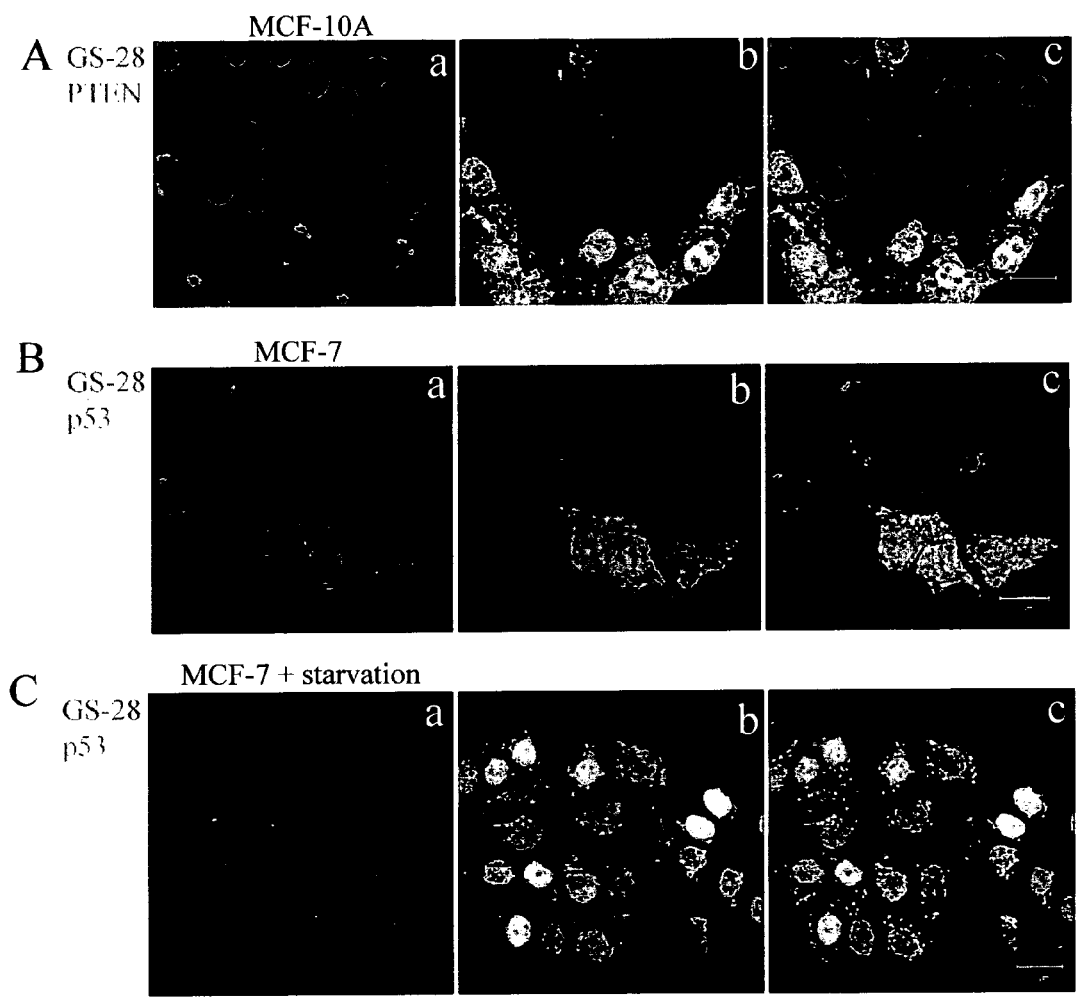
FIG. 6. The general phenomenon of antibody uptake in normal and cancer cells is revealed by indirect immunofluorescence with double staining: A, mouse anti-GS28 (in Red) and rabbit anti-PTEN (in green) antibodies are added to non-permeabilized MCF-10A normal cells. B. mouse anti-GS28 (in red) and rabbit anti-p53 (in green) antibodies are added to non-permeabilized MCF-7 cancer cells. C. mouse anti-GS28 (in red) and rabbit anti-p53 (in green) antibodies are added to non-permeabilized, 16 h serum-starved MCF-7 cells. To-pro-3 iodide is used to stain DNA (blue). Bars, 20 µm.

Again, we found that regardless of whether the antibody source is rabbit or mouse, a fraction of non-permeabilized cells (about 10%) showed efficient uptake of both antibodies in the same cells (FIG. 6A, B). When MCF-7 cells are serum-starved overnight, the non-permeabilized MCF-7 cells are able to take up both GS28 and p53 antibodies with highly efficiency (FIG. 6C).

The indirect immunofluorescence double staining reveals a general phenomenon of antibody uptake in normal and cancer cells. Antibodies can be taken up by non-permeabilized cells, and this is enhanced by serum starvation of cells. The results suggest that intracellular proteins may also be targeted using monoclonal antibody therapies.

Example 14

Over-Expression of PRL-3 and PRL-1 is Associated with a Variety of Metastatic Cancers To evaluate the clinical and prognostic significance of PRL-mAbs as potential drugs against PRL-3- or PRL-1-related cancers, we sought to additionally assess a spectrum of known PRL-mediated cancers which include colon, breast, lung, brain, ovary, melanoma, and gastric cancers[3-12,19].

Using a PRL-3 mAb to perform immunohistochemistry on human multiple cancer tissue arrays, we found that PRL-3 protein is up-regulated in 15% (26/158 cases) of colon cancers, 16.5% (19/96 cases) of breast cancers, and 15% (2/13 cases) of esophagus cancers.

Over-expression of PRL-3 is closely associated with squamous cell carcinoma in lung, penis, and cervix cancers. Selected samples are shown in FIG. 7A.

Figure 7:
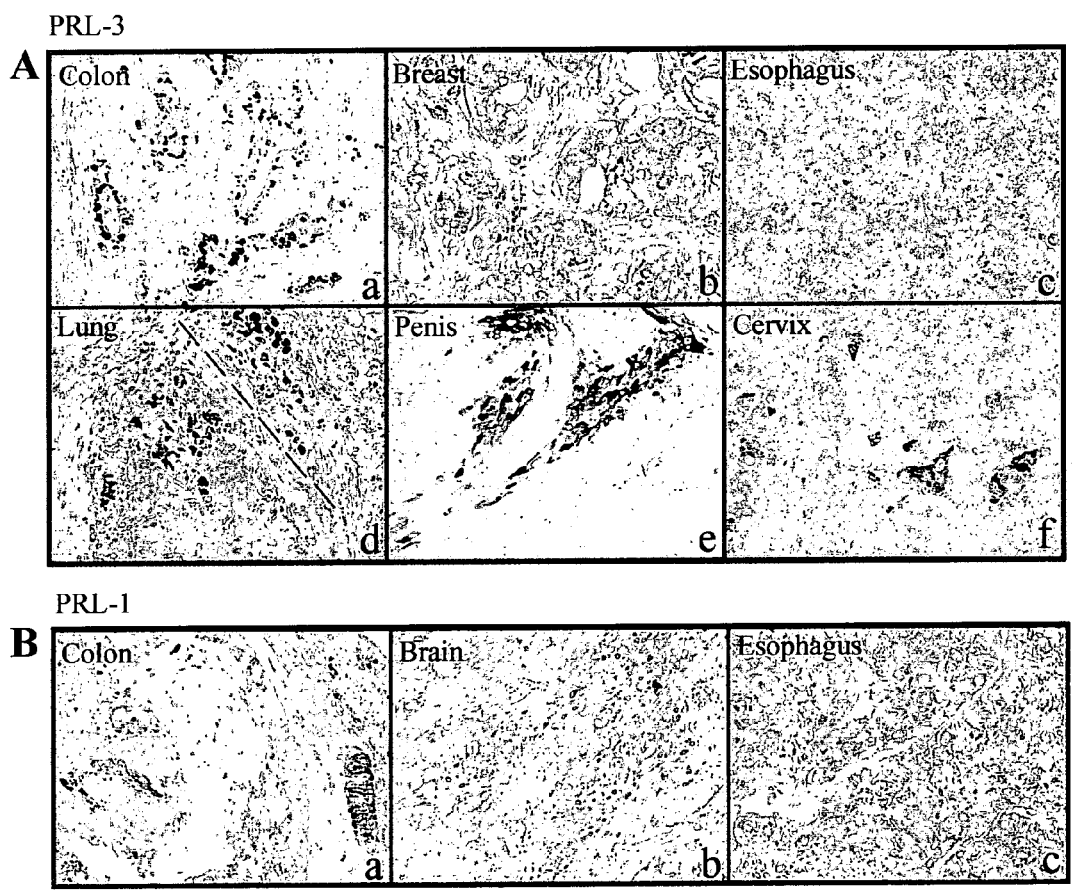
FIG. 7. PRL-3 and PRL-1 are over-expressed in multiple human cancers. A. PRL-3 mAbs (clone 223 or 318) are used to examine the expression of PRL-3 in various human cancer samples. Examples of PRL-3 over-expression are shown in human colon (26/158 cases, a), breast (19/96 cases, b), esophagus (2/13 cases, c), lung (d, the smoke deposits at the upper right-hand side of the dotted line stained black), penis (e), and cervix cancers (f). The PRL-3 positive signals are shown in brown by immunohistochemistry with 3,3'-diaminobenzidine chromogen (DAB). Magnification of all images is ×400. B. PRL-1 mAb (clone 269) is used to examine the expression of PRL-1 in various human cancer samples. Examples of PRL-1 over-expression in human colon (8/128 cases, a, ×200 magnification), brain (5/20 cases, b, ×200), and esophagus (1/13 cases, c, ×400) are shown.

PRL-1 protein is over-expressed in 6.2% (8/128 cases) of colon cancers; in 20% (5/20 cases) of brain cancers, and in 7.6% (1/13 cases) of esophagus cancers (FIG. 7B). In these cancer samples, PRL-positive signals are mainly localized at the plasma membrane and the cytoplasm.

Example 15

Discussion (Example 1 to Example 14)

Metastasis is the most fearsome aspect of cancer. We and others have shown that over-expression of PRL-3 and PRL-1 is associated with a variety of human cancers[3-12,19]. In this study, we further demonstrate that PRL-3 protein is up-regulated in colon, breast and esophagus cancers. Over-expression of PRL-3 is closely associated with squamous cell carcinoma in lung, penis, and cervix cancers. PRL-1 protein is also over-expressed in colon, brain and esophagus cancers.

Targeting cancer cells that over-express intracellular PRL to prevent cancer metastasis by exogenous reagents is a challenging task. Monoclonal antibodies (mAbs) constitute the most rapidly growing class of human therapeutics and are proven agents for recognizing and destroying malignant cells. In order to block PRL-mediated cancer metastases, we need to ablate PRL-expressing cancer cells to prevent them from further spreading. We attempt to approach this challenging aim with monoclonal antibody therapy in mice. Using an experimental metastasis assay in which cultured PRL-tumour cells are directly introduced into each mouse via its tail, we examined in vivo growth and tumour formation of cancer cells. There are four major steps in the process of cancer metastasis. Firstly, cancer cells have to enhance migratory ability in order to escape and dissociate from primary tumour. Secondly, cancer cells need to enter and survive in the blood circulation (intravasation). Thirdly, cancer cells ought to get out from the blood vessels (extravasation) in order to land on a new organ. Fourthly, cancer cells (seeds) need to survive in the distant organs (soils) to grow up into metastatic tumours. We started our metastatic assay at the step of intravasation by injecting one million EGFP-PRL-cancer cells directly into blood vessel via the tail vein (FIG. 1). The process of cancer metastasis is a long and difficult journey; only about 0.01% (~100 tumours out of $1 \times 10^6$ cancer cells) of cancer cells is estimated to reach their final destination successfully. By the end of the experiment, we observed about 100-150 metastatic lung tumours in untreated mice (FIG. 2A, a-d) and about 10-15 metastatic lung tumours in mice treated with PRL-specific mAbs (FIG. 2A, e-h). Our studies represent the first examples of effectively (~90%) blocking experimental metastasis in mice by using mAbs against their respective phosphatases despite their intracellular localization. In addition, we showed that PRL-mAb is specific to its own antigen. PRL-1 mAb specifically blocks the formation of PRL-1 but not PRL-3 metastatic tumours; while PRL-3 mAb specifically blocks the formation of PRL-3 but not PRL-1 metastatic tumours (FIG. 3). Furthermore, we demonstrated that the PRL-3 mAbs do not block tumour formation by CT26 mouse colon cancer cells in which the endogenous PRL-3 phosphatase is not expressed (FIG. 4A, B). Significantly, we show that PRL-3 mAbs effectively block the formation of metastatic tumours by a human ovarian cancer cell line A2780 that expresses endogenous PRL-3 protein. The effective inhibition of metastatic tumour formation by PRL-3 positive naturally-occurring human cancer cells is important as it indicates that PRL-3 mAb or its humanized antibodies may be candidates to treat human cancers associated with PRL-3 overexpression. Although the comparison of PRL-3 antibody's inhibitory effect on A2780 human ovarian cancer cells with the non-inhibitory effect on mouse CT26 colon cancer cells indicates the antibody is targeting cancer cells endogenously expressing PRL-3, future studies employing isogenic cancer cells differing only in the expression levels of PRL-3 are required to convincingly demonstrate this point.

There are a number of possible mechanisms responsible for PRL-3 antibody-mediated inhibition of tumour formation in the experimental metastasis assay Firstly, the antibody may potentially enter into PRL-3 expressing cells to target intracellular PRL-3 and neutralize its function. The uptake of antibody against PRL-3 by a fraction of PRL-3 expressing cancer cells in culture and the enhancement of antibody uptake upon serum-starvation seem to support this mode of action. Secondly, a small fraction of PRL-3 may be externalized and displayed on the surface of the PRL-3 expressing cells. Binding of antibody to surface-exposed PRL-3 may trigger immune responses such as complement-mediated cytotoxicity (CDC), antibody-dependent cellular cytotoxicity (ADCC), and/or complement-dependent cellular cytotoxicity (CDCC) to destroy the cancer cells. Thirdly, intracellular PRL-3 could be proteolytically processed and antigenic fragments may be presented on the cell surface by class I major histocompatibility antigen so that the cancer cells become targets of cytotoxic T cells.

To address the first possibility for how these PRL-mAbs inhibit cancer metastasis driven by their respective intracellular antigens, we provide evidence that the uptake by PRL-3- or PRL-1-expressing cells of their respective PRL-antibodies might be a general phenomenon as we also found that a PRL-unrelated antibody to the Golgi marker-GS28 can penetrate into live CHO cells in culture and the antibody uptake is enhanced by serum starvation of the cells (FIG. 5B).

An important question is whether the antibody penetration occurs specifically in cancer cells or in untransformed cell types as well, and if other classes of antibody can also enter cells. Three PRL-unrelated antibodies are tested on two other cell lines. These are mouse anti-GS28 and rabbit anti-PTEN antibodies on non-permeabilized human mammary epithelial cells (MCF-10A); and mouse anti-GS28 and rabbit anti-p53 on human breast cancer cells (MCF-7).

Again, we found that regardless of whether the antibody source is rabbit or mouse, a fraction of non-permeabilized cells (about 10%) showed efficient uptake of both antibodies in the same cells (FIG. 6A, B). When MCF-7 cells are serum-starved overnight, the non-permeabilized MCF-7 cells are able to take up both GS28 and p53 antibodies with high efficiency (about 70% FIG. 6C).

Serum-starvation is used to arrest cells at G1 and G0 phases[21]. It is possible that particular stages of the cell cycle can contribute to the abilities of cells to take up the antibodies. In vivo, cancer cells are under hypoxic stress and serum deprivation, conditions that might enhance the abilities of cancer cells to take up antibodies.

The findings suggest a hitherto unrecognized general phenomenon that cells are able to take up antibodies to neutralize intracellular antigens. In particular, we have demonstrated that PRL-3 and PRL-1 antibodies specifically target their respective intracellular proteins and ablate tumour formation with no detectable side effects in these animals. Although the specific steps of tumour formation in the experimental metastasis assay inhibited by PRL-3 antibody remain to be defined by future studies, our results indicate that single cells (or micro-metastases consisting of cluster cells) seeded in the lung or other secondary tissues are likely the targets of PRL-3 antibody as reflected by the dramatic reduction in the numbers of tumour nodules. Since the seeding of cancer cells in secondary tissues and progression of micrometastases into macrometastases are major limiting steps in cancer spread, targeting these stages with PRL-3 antibodies is of potential clinical relevance in preventing cancer metastasis.

Here we provide evidence to demonstrate the PRL-3 mAbs are correctly targeted to tumours with endogenous expression of PRL-3. Our data finally suggest that intracellular proteins may also be targeted using monoclonal antibody therapies to ablate metastatic tumour formation. We propose that cancer researchers consider reevaluating a wide spectrum of intracellular oncoproteins as possible targets of mAbs for anticancer therapy.

Example 16

Generation of Specific PRL-3 and PRL-1 Mouse/Human Chimeric mAbs (Clone #318, 269)

For PRL-3 chimeric mAb, the total RNA is extracted from $6 \times 10^6$ hybridoma cells (clone#318) using RNeasy Mini Kit (QIAGEN, cat#74104). DNAse is used during RNA extraction. The RNAs are then reverse-transcribed into cDNA using SuperScript II RNase H (Invitrogen, Cat 18064-014). The resulting total cDNAs are used as templates to generate 'universal variable region' using Ig-Prime Kits (Novagen, cat#69831-3) for PCR (95° C., 54° C., 72° C.) with 30 cycles. The PCR fragment is cloned into PCRII-TOPO-Vector with TA cloning kit (Invitrogen, part#45-0640). The PCR fragment is cut with Mfe1 and XhoI then inserted into respective sites of a human IgG1 constant region expression vector-pCMV-human IgG1 (18) to join mouse variable region of heavy chain (clone #318) with human IgG1 constant region. Similar PCR procedures are performed for mouse variable region of light chain with ends containing restriction sites for ApaL1 and Pst 1 are used to PCR the mouse variable light chain (clone #318). The PCR fragment is cut with ApaL1 and Pst I and then inserted into respective sites of a human IgG1 constant region expression vector containing variable region of heavy chain of clone #318. The complete construct is transiently transfected into 293T cells which are cultured with ultra-low IgG FBS (Gibco, 16250-078). The chimeric mAb is harvested from the culture supernatant and concentrated up to 40 times with centrifugal filter devices (Millipore, cat#UFC900596). The chimeric mAb is tested for its specificity by indirect immunofluorescence (IF) and Western blot analysis. To generate PCR fragment for PRL-1 (clone #269) variable region of light chain, similarly, mRNAs is extracted from hybridoma cells #269 and the mRNAs are then reverse-transcribed into cDNAs that are used to retrieve the coding sequence of the variable region of heavy and light chains. To generate PCR fragment for PRL-1 variable region of light chain, similar procedures are carried as mentioned above.

Example 17

Generation of DLD-1-EGFP-PRL-3 Tumour Cell Line

DLD-1 colon carcinoma cells from ATCC CCL-221 (Mannassas, Va.). EGFP-PRL-3 expression construct is transfected into DLD-1 cells using Lipofectamine 2000 from Invitrogen (Carlsbad, Calif.). To obtain EGFP-PRL-3 tumours, 8-week old nude mice (Jackson Labs, USA) are each injected into the hips of nude mice to form xenograft tumour. Mice are sacrificed at 3 weeks after cancer cell inoculation. Tumours are removed and examined under the fluorescent microscope (Zeiss, M2 Bio Quad). To generate DLD-1-EGFP-PRL-3 tumour cell line, EGFP-tumour is washed twice in PBS under sterile conditions; cut into tiny pieces and cultured at 37° C. with 5% $CO_2$ with RPMI 1640, 10% FBS and 1% antibiotics (Sigma). The cells are trypsinized and split at a ratio of 1:3 into new dishes. The tumour cell lines homogeneously expressed EGFP-PRL-3 or EGFP-PRL-1 are confirmed by indirect immunofluorescence.

Example 18

Cell Lines: HCT116 (CCL-247), DLD-1 (CCL-221), B16F0 (CRL-6475), B16F10 (CRL-6322), A2780

HCT116 (CCL-247) is a human colorectal carcinoma cell line. DLD-1 (CCL-221) is a human colorectal adenocarcinoma cell line. B16F0 (CRL-6475) and B16F10 (CRL-6322) are two mouse melanoma cell lines. All four cell lines are purchased from ATCC. A2780 is a human ovarian cancer cell line and is purchased from ECACC (Cat#93112519 UK).

Example 19

Experimental Animals

Reference is made to document A19. All animal studies have been approved by our Institute's Review Board. We follow the policies from the Animal Facility Center of The Agency for Science, Technology and Research (A* STAR), Singapore. Eight-week nude mice (Jackson Labs, USA) are used. $1 \times 10^6$ cancer cells are injected into the circulation of nude mice via the tail vein on day 1. Either chimeric mAb for treated mice or PBS for untreated mice is administrated into tail vein on day 3.

Example 20

Generation of Specific PRL-3 Mouse/Human Chimeric mAb (Clone #318)

Figure 8A:
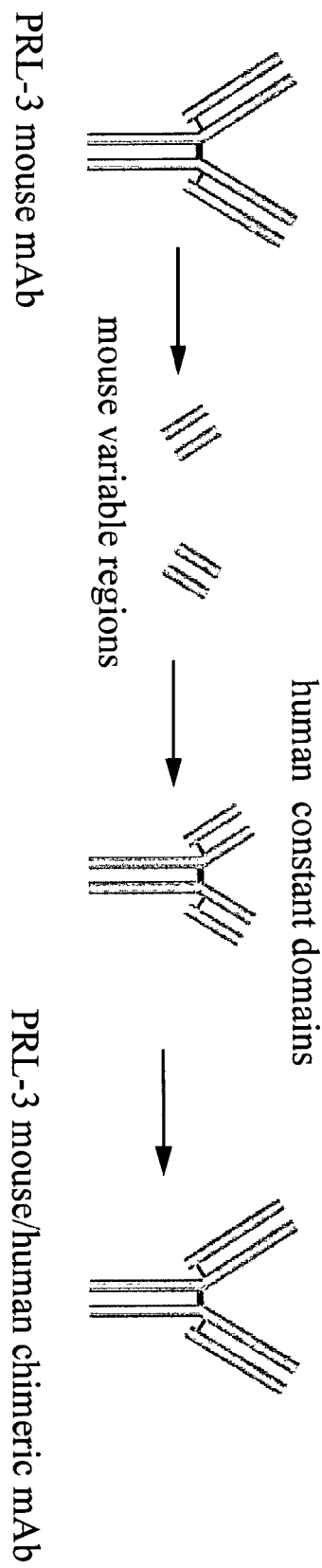
FIG. 8. PRL-3 and PRL-1 chimeric mAbs specifically react only to their respective antigen. A. A model is shown to illustrate an outline of the major steps for chimeric mAb construction B. By IF, PRL-3 chimeric mAb (#318) is tested on DLD-1 cells that overexpress EGFP-PRL-3 (a) and showed that the PRL-3 chimeric mAb could recognize EGFP-PRL-3 in these cells (b). Merged image is shown in c. Similarly, PRL-1 chimeric mAb (#269) is also tested on DLD-1 human colorectal cancer cells that overexpress EGFP-PRL-1 (d) and showed that the PRL-1 mAb could recognize EGFP-PRL-1 in these cells (e). Merged image is shown in f. Bars: 20 µm. C. By western blot analysis, the PRL-3 chimeric mAb are assessed on 4 cell lysates derived from DLD-1 cells that overexpress EGFP-PRL-3 (lane 1), and CHO cells that overexpress myc-PRL-3 (lane 2), myc-PRL-1 (lane 3) or myc-PRL-2 (lane 4). PRL-3 chimeric mAb only react with EGFP-PRL-3 and myc-PRL-3 but not with myc-PRL-1 and myc-PRL-2. D. the PRL-1 chimeric mAb is assessed on 3 GST-PRL proteins: GST-PRL-1 (lane 1), GST-PRL-2 (lane 2) and GST-PRL-3 (lane 3). PRL-1 chimeric mAb react only with GST-PRL-1 but not with GST-PRL-2 and GST-PRL-3.

We are encouraged by the fact that PRL-1 and PRL-3 mouse mAbs could specifically target their respective intracellular PRL phosphatases and inhibit cancer metastases in experimental animals (reference A16). In an attempt to bring the laboratory work to clinic, we engineered a mouse/human chimeric mAb against PRL-3 to reduce the potential antigenicity of the mouse mAb in human. The PRL-3 chimeric mAb is successfully developed in which the constant domains of the human IgG molecule (reference A18) are combined with the mouse variable regions (heavy and light chains) of PRL-3 mAb clone#318 by transgenic fusion of the immunoglobulin genes (FIG. 8A) that is performed by a recombinant DNA technology. The expression construct is transfected into Human Embryonic Kidney cells expressing simian virus 40 T antigen (293T) cells to produce the chimeric PRL-3 mAb that is then harvested from the culture medium and further concentrated by 40 times.

Example 21

Generation of Specific PRL-1 Mouse-Human Chimeric mAb (Clone #269)

We carried out the similar strategy to generate PRL-1 mouse variable regions of heavy and light chains, and then are respectively interested into the constant domains of the human IgG expression vector (reference A18) to generate chimeric PRL-1 mAb.

Example 22

The PRL-3 and PRL-1 Chimeric mAbs Specifically Target to their Antigens

Figure 8B:
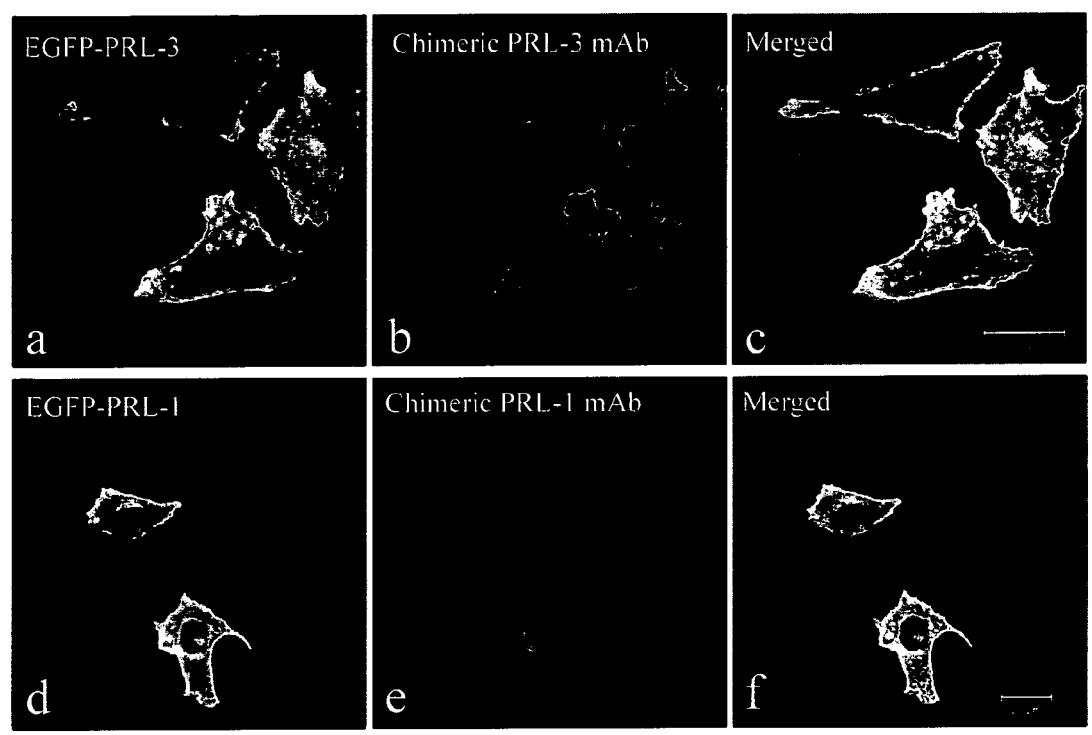
Figure 8C:
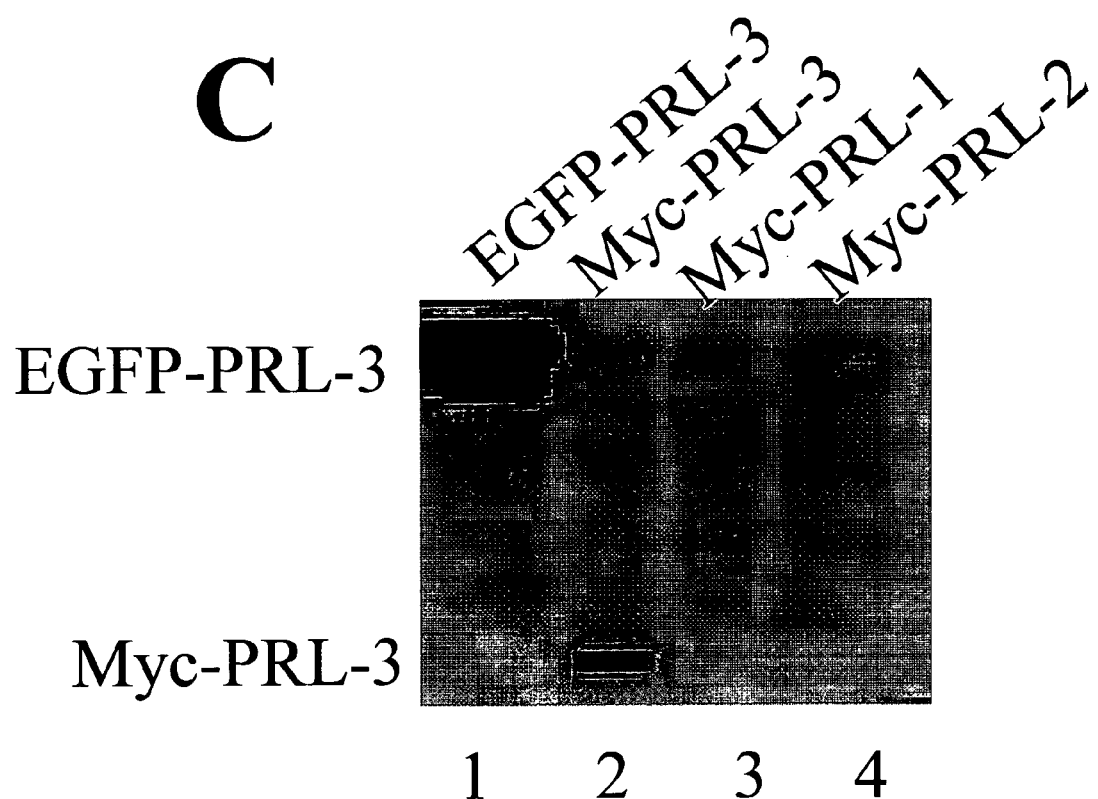
Figure 8D:
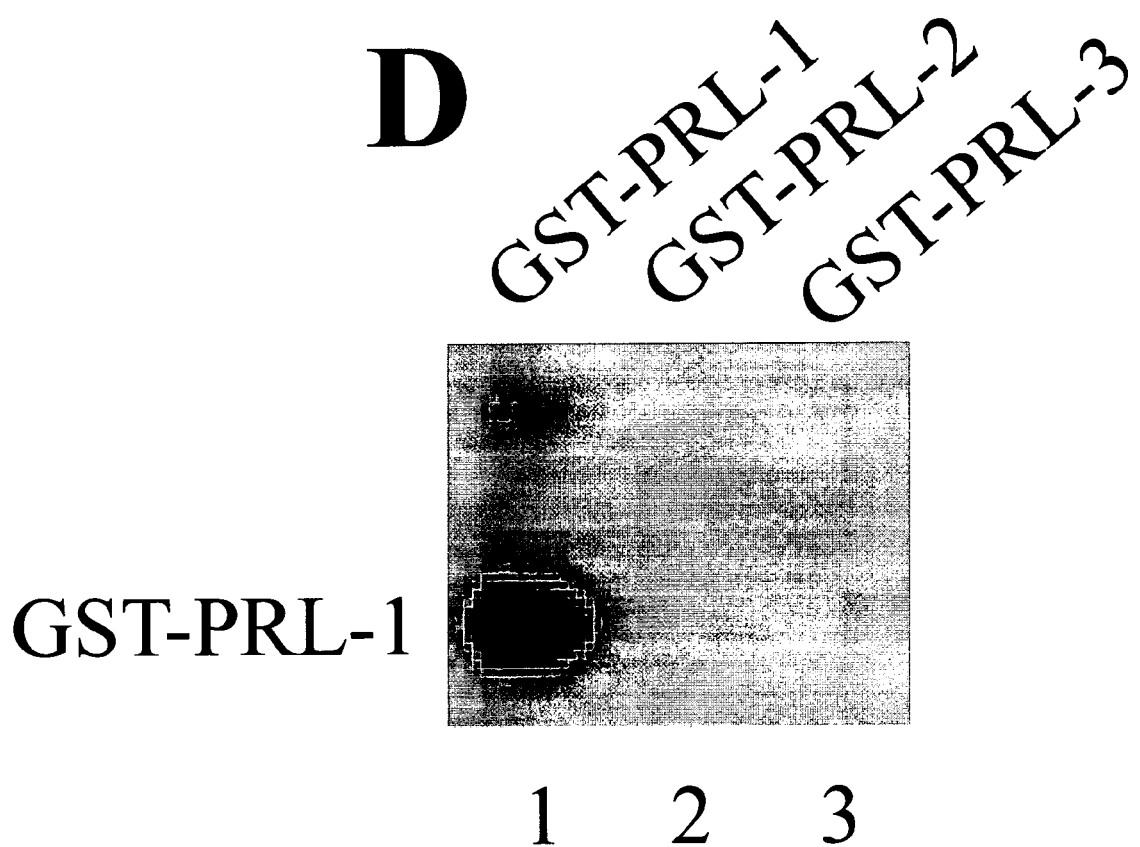

The PRL-3 and PRL-1 chimeric mAbs are confirmed for their antigen specificities by performing indirect immuofluorescence (IF) (FIG. 8B) and western blot analyses (FIG. 8C and FIG. 8D). The data show that the PRL-3 chimeric mAb recognizes only PRL-3 but not PRL-1 and -2 proteins; while the PRL-1 chimeric mAb binds only to PRL-1 but not to PRL-2 and -3 proteins.

Example 23

PRL-3 Chimeric Antibody Effectively Inhibits the Formation of Metastatic Tumours by A2780 Cells and HCT116 that Express Endogenous PRL-3; but not DLD-1 Cells that do not Express Endogenous PRL-3

Figure 9A:
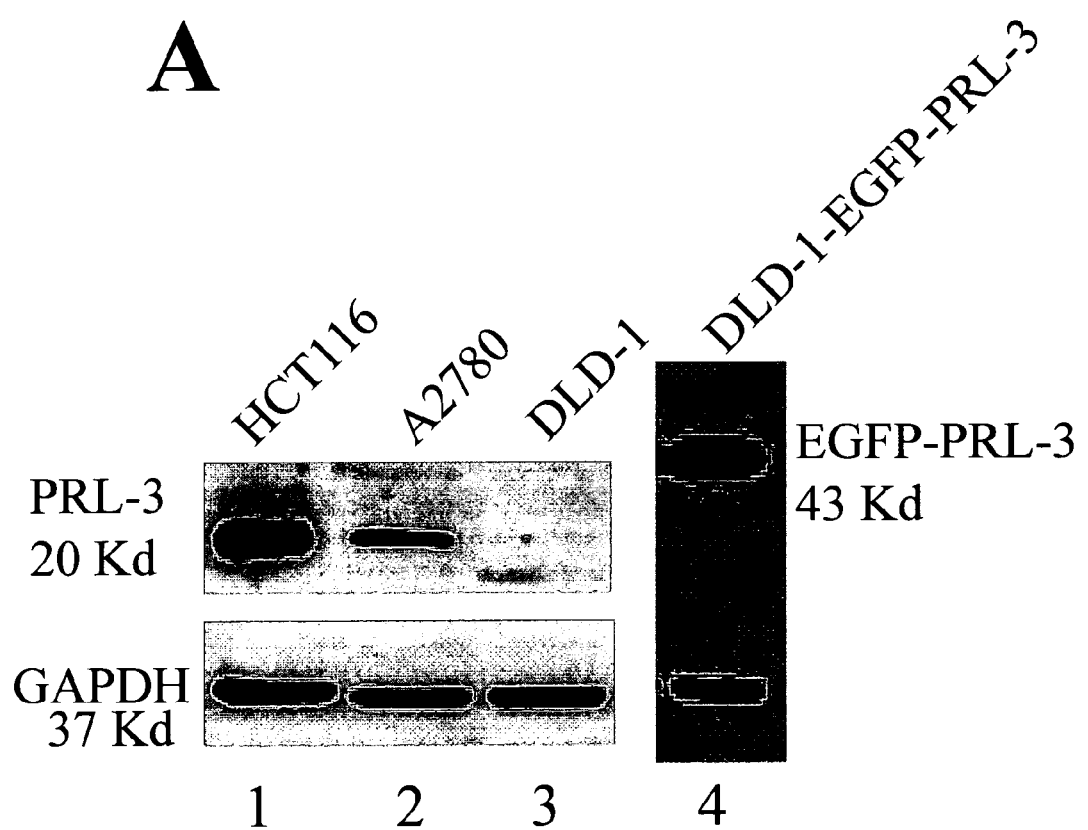
FIG. 9. PRL-3 chimeric mAb dramatically inhibits the formation of metastatic tumours by A2780 cells and HCT116 that express endogenous PRL-3; but not DLD-1 cells that do not express endogenous PRL-3. A. The total cell lysates are prepared from HCT116, A2780, DLD-1 cancer cells, and DLD-1 cells that overexpress EGFP-PRL-3. The endogenous PRL-3 protein is detected in HCT116 and A2780 but not in DLD-1 cells. The exogenous EGFP-PRL-3 is only detected in lane 4. For B, C, and D: Nude mice are injected with $1 \times 10^6$ cancer cells via tail veins on day 1. The mice are either administrated with PRL-3 chimeric mAb (treated) or PBS (untreated). The time period of each experiment are determined and ended when untreated mice are too sick. The photos are taken at the ends of each experiment. B. treatment for HCT116 cells, treated mice at the left and untreated mice at the right. C. treatment for A2780 cells, treated mice at the left and untreated mice at the right. D. a. treatment for DLD-1 cells, treated mice at the left and untreated mice at the right. b. treatment for DLD-1 cells expressing EGFP-PRL-3, untreated mice at the left and treated mice at the right.
Figure 9B:
Figure 9C:
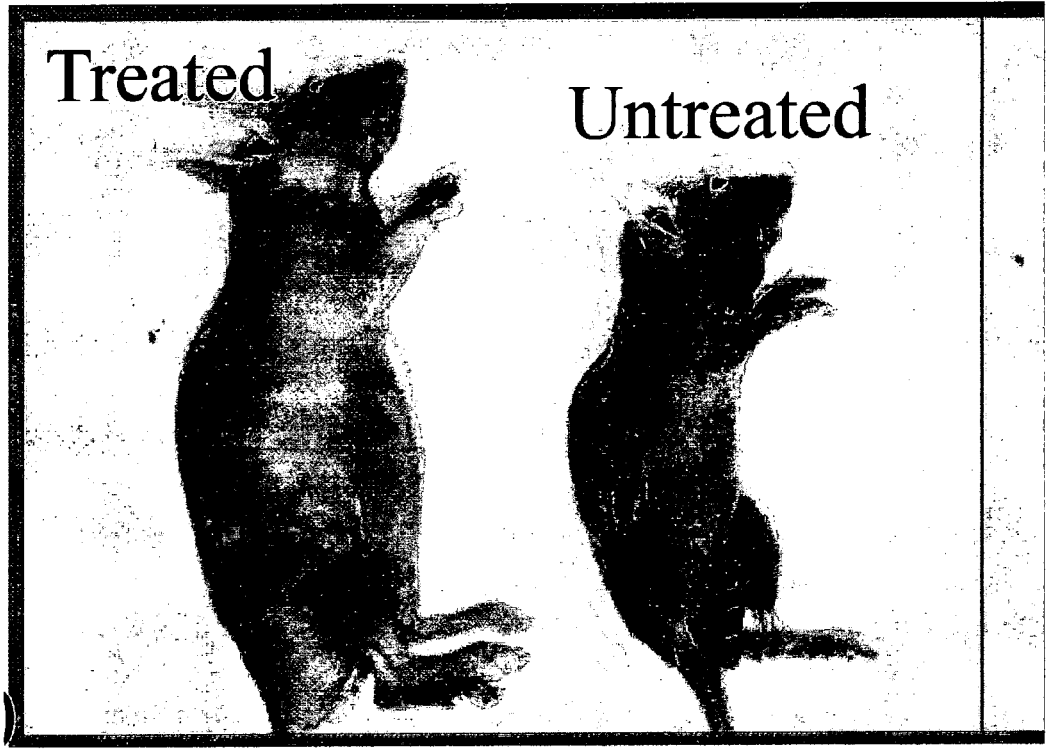
Figure 9C:
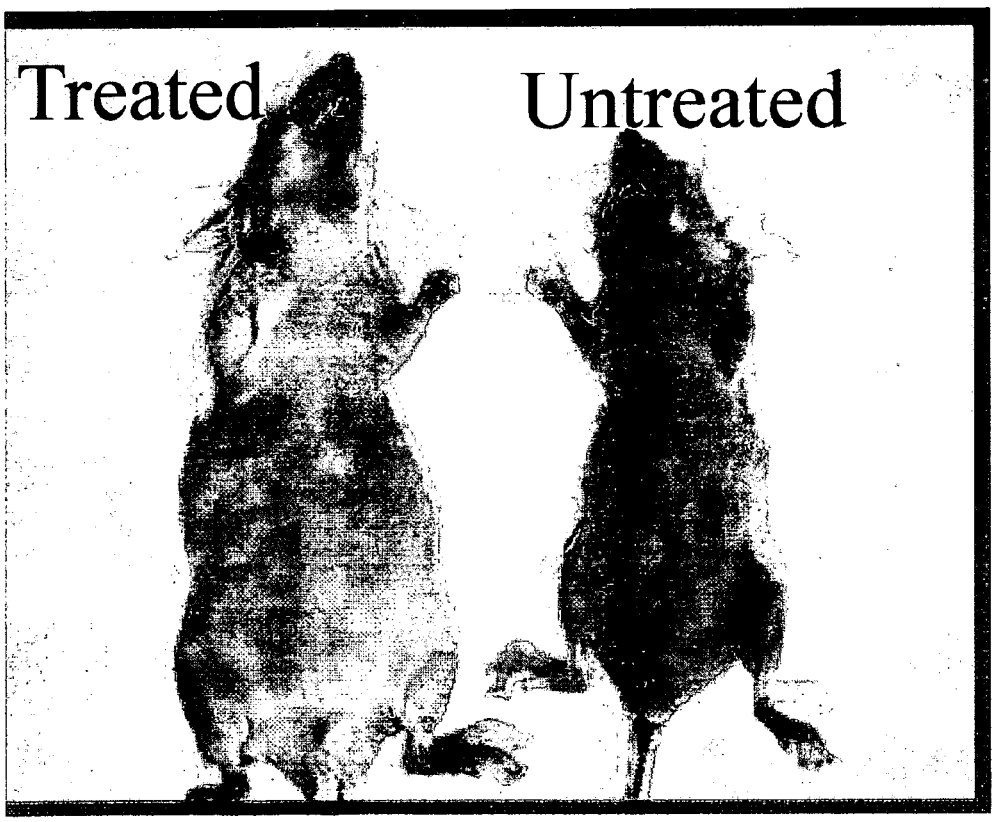
Figure 9D:
Figure 9D:
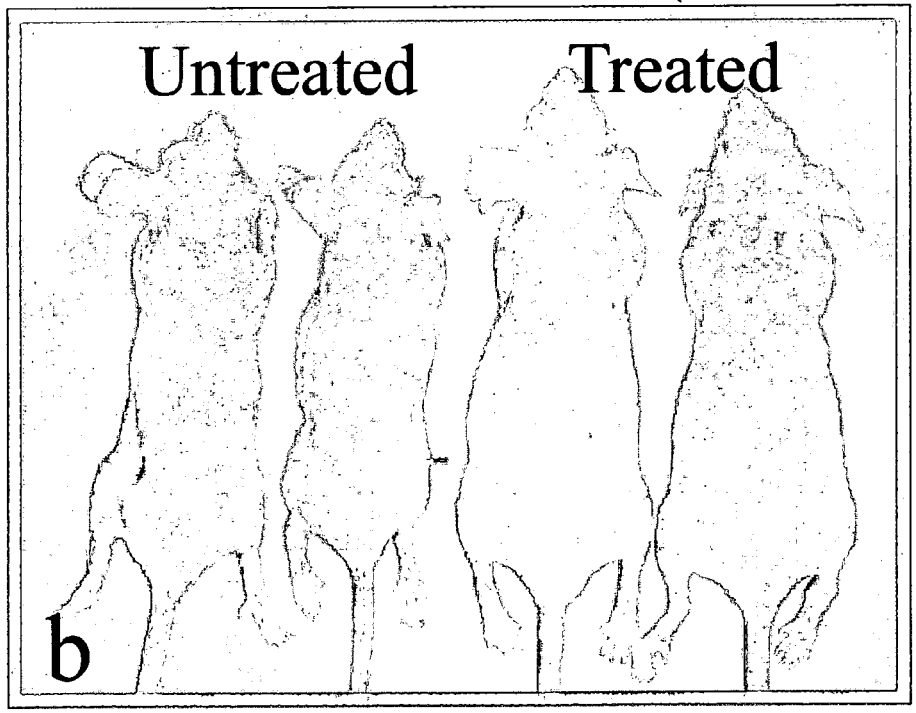
Figure 10A:
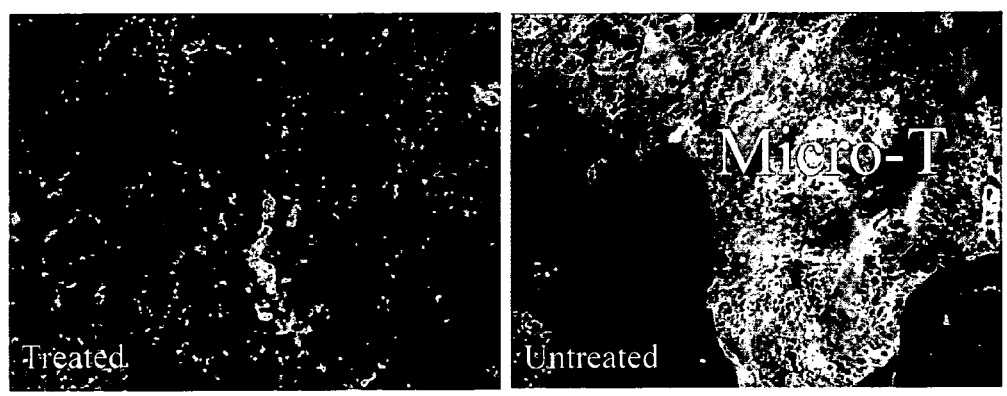
FIG. 10. PRL-3 enhances lung metastatic tumour formation and cancer cell survival in the blood circulation. A. Lung sections from treated and untreated mice are shown. Multiple micro-tumours (indicated with Micro-T) is seen under fluorescence microscope in lung section from untreated mice but less found in lung sections from treated mice. B. Blood samples obtained from tail veins from treated and untreated mice are smeared on the glass slides and examined for EGFP-PRL-3 cancer cells under fluorescence microscope. Arrows indicate the EGFP-PRL-3 positive cancer cells.
Figure 10B:

A crucial experiment is performed to assess if the PRL-3 chimeric mAb could target and block the formation of metastatic tumours derived from cancer cells that naturally express PRL-3 protein. Dozens of cancer cells are screened for PRL-3 expression by western blot analysis. The candidate cancer cell lines that are ideal to be used in this experiment should have two properties: 1. naturally expressed PRL-3 protein. 2. be able to cause metastatic tumour formation rapidly. We found A2780 human ovarian cancer cell line and HCT116 human colorectal cancer cell line have these two properties and confirmed that A2780 cells and HCT116 cells express PRL-3 protein naturally (FIG. 9A lane 1, 2). A2780 cells are reported previously as PRL-3 positive cell line (reference A4). Remarkably, significant differences are found between PRL-3 chimeric mAb treated and untreated mice at 1-month post-inoculation of HCT116 (n=5) or A2780 (n=8) cells. Pathologic appearances (unhealthy and skinny) are observed only in untreated mice (FIG. 9B and FIG. 9C, L-side) but not in treated mice (FIG. 9B and FIG. 9C, R-side). The treated mice remain healthy for a prolonged period of time. These results suggest that PRL-3 chimeric mAb is able to block metastatic tumour formation of cancer cells naturally expressing PRL-3. In contrast, we identified a human colon cancer cell line DLD-1 that does not express PRL-3 protein (FIG. 9A, lane 3). The DLD-1 cells are serviced as a negative control for this experiment. Expectedly, no difference is found between treated (FIG. 9D, L-side) and untreated (FIG. 9D, R-side) groups (n=5) of mice receiving DLD-1 cells, which all show healthy appearance, at 3.5-month post-inoculation of DLD-1 cells. Strikingly, DLD-1 cells engineered to overexpress EGFP-PRL-3 could cause pathological phenotype in mice at 2-month post-inoculation of the cells. Multiple micro-metastatic tumours are found in the lungs of nude mice carrying these exogenous PRL-3 expressing cancer cells. The EGFP-PRL-3 positive cells are also found in the blood smear of the untreated mice (FIG. 10A n=5) at this time; suggesting that PRL-3 could prolong cell survival in the blood stream. In contrast, mice received PRL-3 chimeric mAb treatment showed significantly difference in their sizes and healthy appearance for a prolonged period of time. Micro-metastatic tumours are not found in the lungs of treated nude mice carrying these exogenous PRL-3 expressing cancer cells. The EGFP-PRL-3 positive cells are less found in the blood smear of the treated mice (FIG. 10B n=5). The results suggest that PRL-3 chimeric mAb is able to block metastatic tumour formation of cancer cells that either express endogenous PRL-3 naturally or express engineered PRL-3 exogenously. Importantly, the antibody has no effect on cancer cells that do not express endogenous PRL-3.

Example 24

PRL-3 Chimeric Antibody Effectively Inhibits the Formation of Metastatic Tumours by B16F0 Cells that Express Endogenous PRL-3; but not B16F10 Cells that do not Express Endogenous PRL-3

Figure 11A:
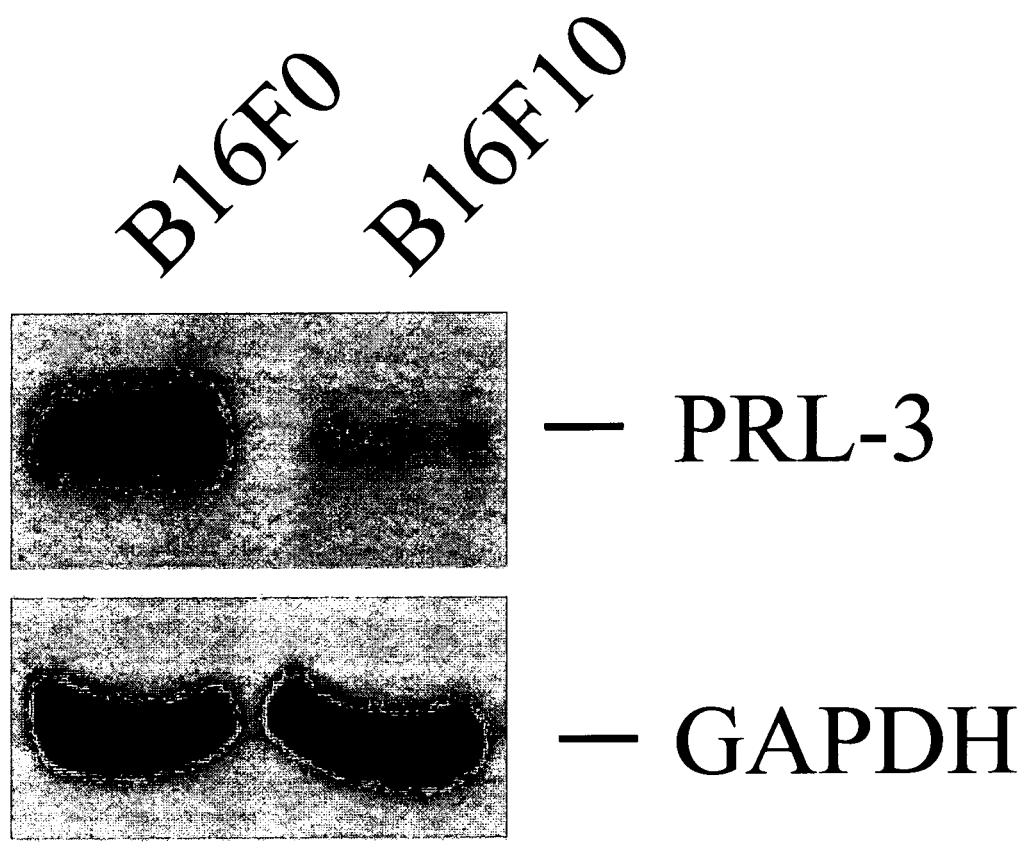
FIG. 11. PRL-3 chimeric antibody effectively inhibits the formation of metastatic tumours by B16F0 cells that express endogenous PRL-3; but not B16F10 cells that do not express endogenous PRL-3. A. Total cell lysates are prepared from B16F0 and B16F10 cancer cells. The endogenous PRL-3 protein is detected only in B16F0 but not in B16F10 cells. B. Nude mice are injected with $1 \times 10^6$ B16F0 cells on day 1 followed by chimeric mAb treatment. Treated mice at the left and untreated mice at the right are shown. Tumours are found in the adrenal, liver, bone, and abdomen in untreated mice. PRL-3 mAb could eliminate the formations of tumour in most tissues of treated mice. C. Nude mice are injected with $1 \times 10^6$ B16F10 cells on day 1. Treated mice at the top and untreated mice at the bottom are shown. Dozens of lung metastatic tumours are found both in treated and untreated mice.
Figure 11B:
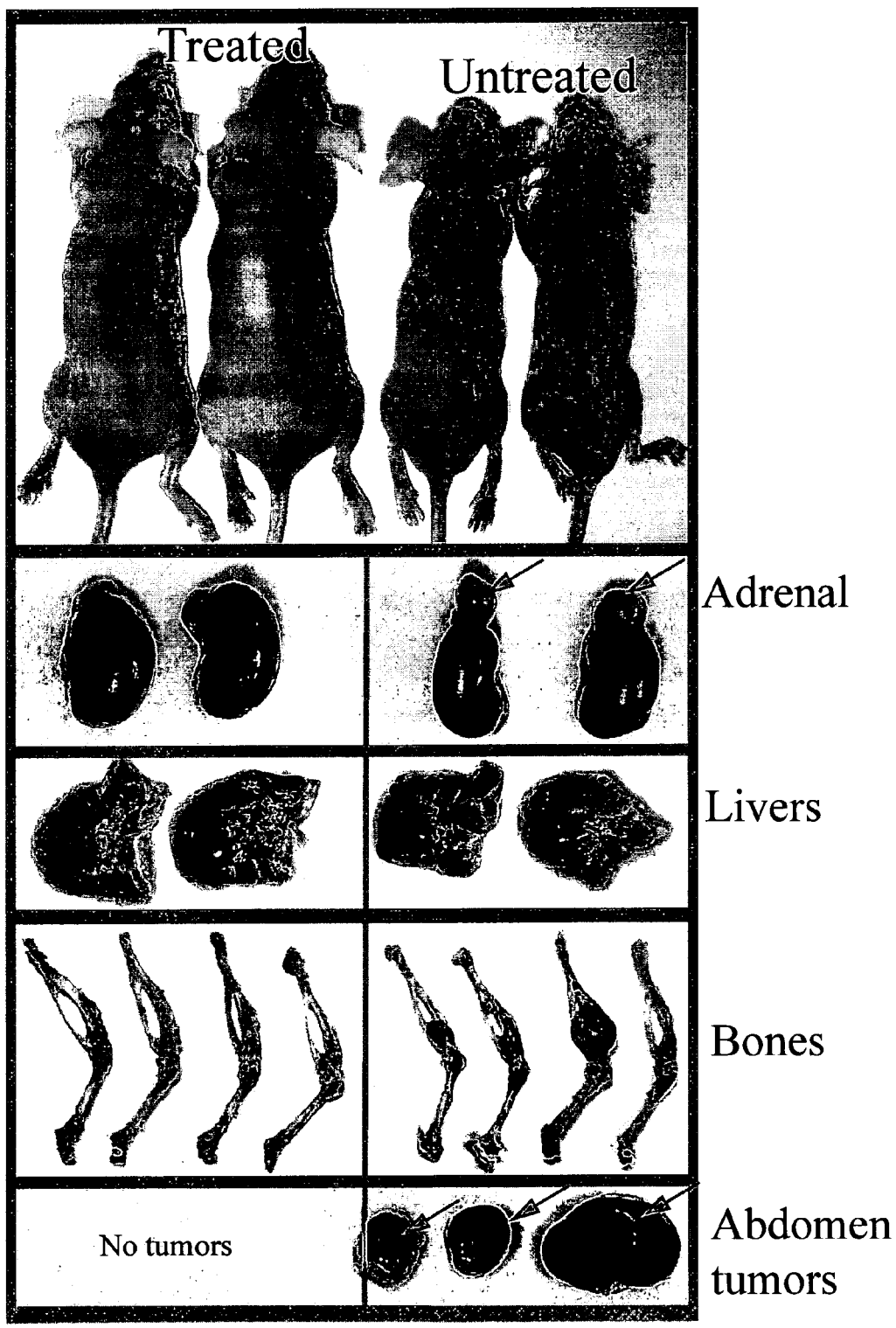
Figure 11C:
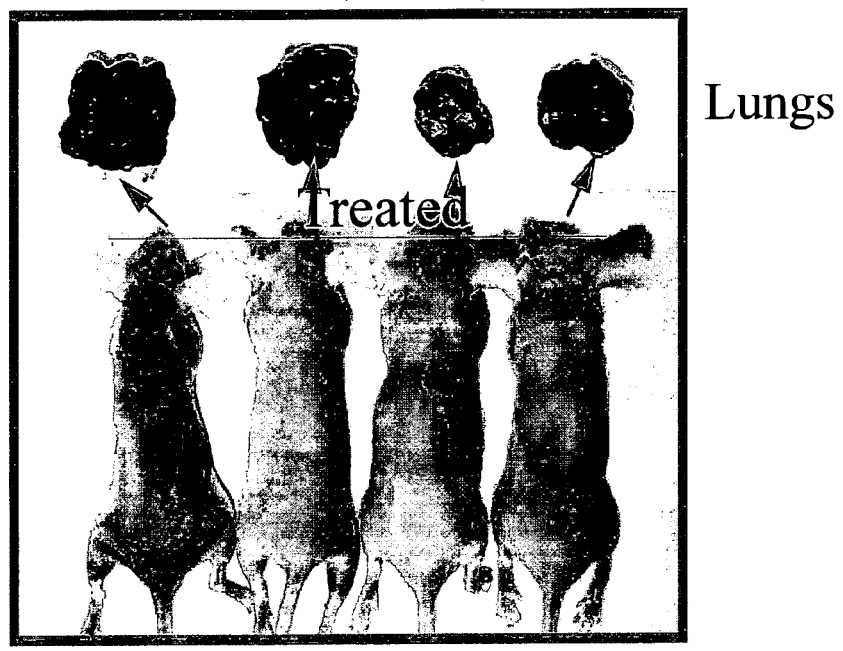
Figure 11D:
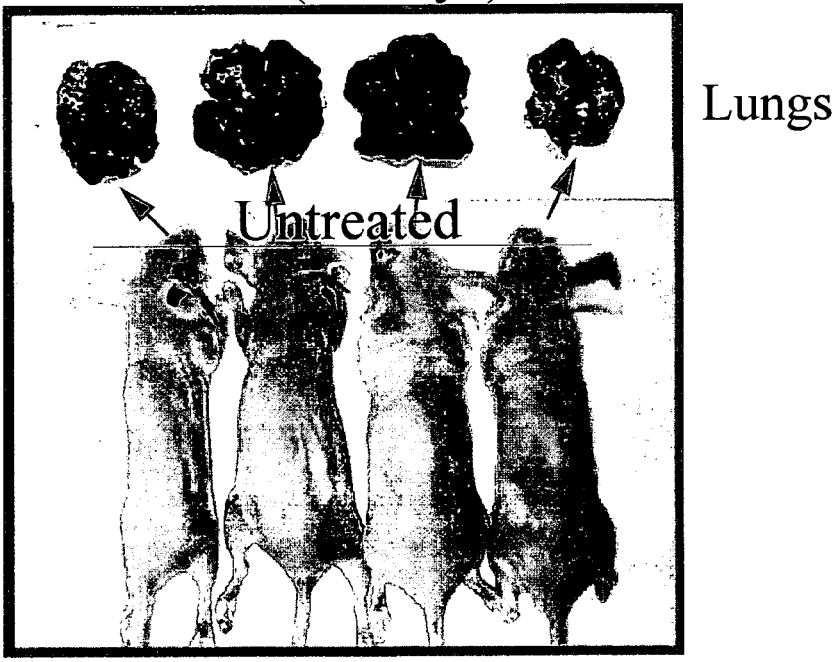

We had demonstrated that the antibody could block metastatic tumours formed by human cancer cells. Now, we use two mouse melanoma cell lines: B16F0 and B16F10 to perform addition mAbs treatments. Both cell lines form multiple metastatic tumours rapidly in mice. For untreated mice carrying B16F0 cancer cells that express endogenous PRL-3 protein (FIG. 11A), metastatic tumours are found in adrenal (arrows indicated), livers, bones and abdomen (FIG. 11B, R-side). Again, we showed that the chimeric mAb could efficiency wipe out metastatic tumours formation in many tissues of treated mice (FIG. 11B, L-side). In a parallel control experiment, dozens of metastatic tumours are found in lungs of untreated or treated mice that carrying B16F10 cancer cells that do not express endogenous PRL-3 protein (FIG. 11A), as one can see that there are no significant differences in numbers of lung metastatic tumours between treated (FIG. 11 upper panel) and untreated mice (lower panel). So far, the results obtained from PRL-3 chimeric mAb treatment on several PRL-3 positive and negative cancer cell lines suggest that the efficiency of the treatment is tightly correlated with whether the formation of metastatic tumour is caused by the PRL-3-overexpression. If the metastatic property of cancer cells is not due to PRL-3 overexpression (B16F10 cells), the administration of PRL-3 chimeric mAb has no effect in blocking tumour formation (FIG. 11C).

Example 25

Discussion (Examples 15 to 24)

Most cancer patients die from metastases and not from their primary disease. Cancer metastasis is a multistep process. The first important step of cancer metastasis involves neoplastic epithelial cells losing cell-cell adhesion and gaining motility, which drive cancer cells to disassociate from the primary site of the tumour and to invade adjacent tissue. The second step requires cancer cells to acquire an ability to get into the blood circulation (intravasation) of the host. These two initial steps might take a long time to incubate and achieve. Here, we used an experimental metastasis assay (reference A 19) and started our experiment at the step of intravasation by directly injecting one million of cancer cells into blood circulation via the tail vein of mice (on day 1) which mimic the rest of metastatic process. We treated the animal with PRL-3 chimeric mAb on day 3, following by twice weekly of the mAb administrations. Taken together from the outcomes of the previous (reference A16) and current antibody treatments, our findings suggest: 1. the process of cancer metastasis is a long and difficult journey; starting with one million cancer cells (seed), by the end of the experiment; we observed about 100 metastatic lung tumours in untreated mice and about 10-15 metastatic lung tumours in mice treated with PRL-specific mAbs (reference A16), the data reflect that only about 0.01% of cancer cells are estimated to reach their final destination successfully. 2. In this study, again, we found fewer numbers of micro-tumour in lung sections from treated mice comparing with those from untreated mice (FIG. 10A); suggesting that the mAb could act on reducing the number but not the size of tumours. 3. The efficiency of the treatment is also highly associated with what time we begin to introduce the chimeric mAbs. If the treatment is not started early enough but delayed to 1-week after cancer cells inoculation, the results would not be as good as early treatment (day 3); these findings implicate that PRL-3 mAb might play a role in neutralizing and eradicating the PRL-3 cancer cells when they are still moving and wondering in the blood stream. Delayed treatment might allow cancer cells to have a chance to pass through the blood vessel (extravasation) and land on distal organ for seeding; the mAb might have less chance to arrest the PRL-3 positive cancer cells beyond extravasation and seeding. This hypothesis is supported by the prolonged presence of DLD-1-EGFP-PRL-3 cells in the circulation of untreated mice and clear reduction of these cells in mice received mAb treatment. 4. Most importantly, PRL-3 chimeric antibody could only effectively block the formation of metastatic tumours that derive from the cancer cells expressing endogenous PRL-3; but not cancer cells that do not express endogenous PRL-3. Therefore, our PRL-3 mAb treatment is very specific to its own antigen. Notably, the mAb acts better through the blood stream but not through local response, we generated xenograft tumours by injecting one million of PRL-3 cancer cells locally in the hip area of the nude mice, we then injected mAb to the similar areas twice weekly starting on day 3, we found that the mAb has no effect in reducing the size of local xenograft tumours (data not shown).

The detailed cellular and molecular mechanisms responsible for PRL-3 mAb to inhibit PRL-3 mediated metastatic tumour formation in the experimental metastasis assay are currently unknown and need to be defined by future study. The results that PRL-3 chimeric mAb could ablate metastatic tumours of PRL-3 expressing cancer cells in mice are encouraging and suggest a concept for other intracellular targets in clinic. Our study might open up new and enormous opportunities for antibody therapy using mAbs against intracellular oncogene products to treat various cancers and cancer metastases. As PRL-1, PRL-2 and PRL-3 are overexpressed in various cancers; we would anticipate the widely needs of the PRL-chimeric mAbs that could be the forerunners of novel medicine to combat various PRL intracellular phosphatses associated tumours. We could select and treat some types of cancer patients (for example: who suffer pancreatic cancer) that would relapse-recurrence within a short period of time when the primary cancer is first diagnosed. The differences between treated and untreated groups of patient would be able to reveal if the chimeric mAbs have effects or not within a short period of time.

Example 26

Anti-PRL3 Antibody 318 Binds to both Intracellular and Externalised or Secreted PRL3 Polypeptide An experiment is conducted as follows:

1. Grow A2780, HCT116, B16F0, B16 F10 cells in 10 cm culture dish each till 80% confluent.

2. PBS wash for several times.

3. Change medium (8 ml) into FBS-free overnight.

4. *next day, harvest medium and spin 3K, discard the pellet, spin 14K again and keep the supernatant (*lyses cells from the dishes, check each cell line for PRL-3 expression in FIG. 12A)

5. use GAPDH as a protein loading control for cell lysates (FIG. 12B)

6. Check the medium under microscopy to make sure there is no cell in the medium.

7. Concentrated the medium and run SDS gel for secreted or externalized PRL-3 in culture medium (FIG. 12C).

Figure 12:
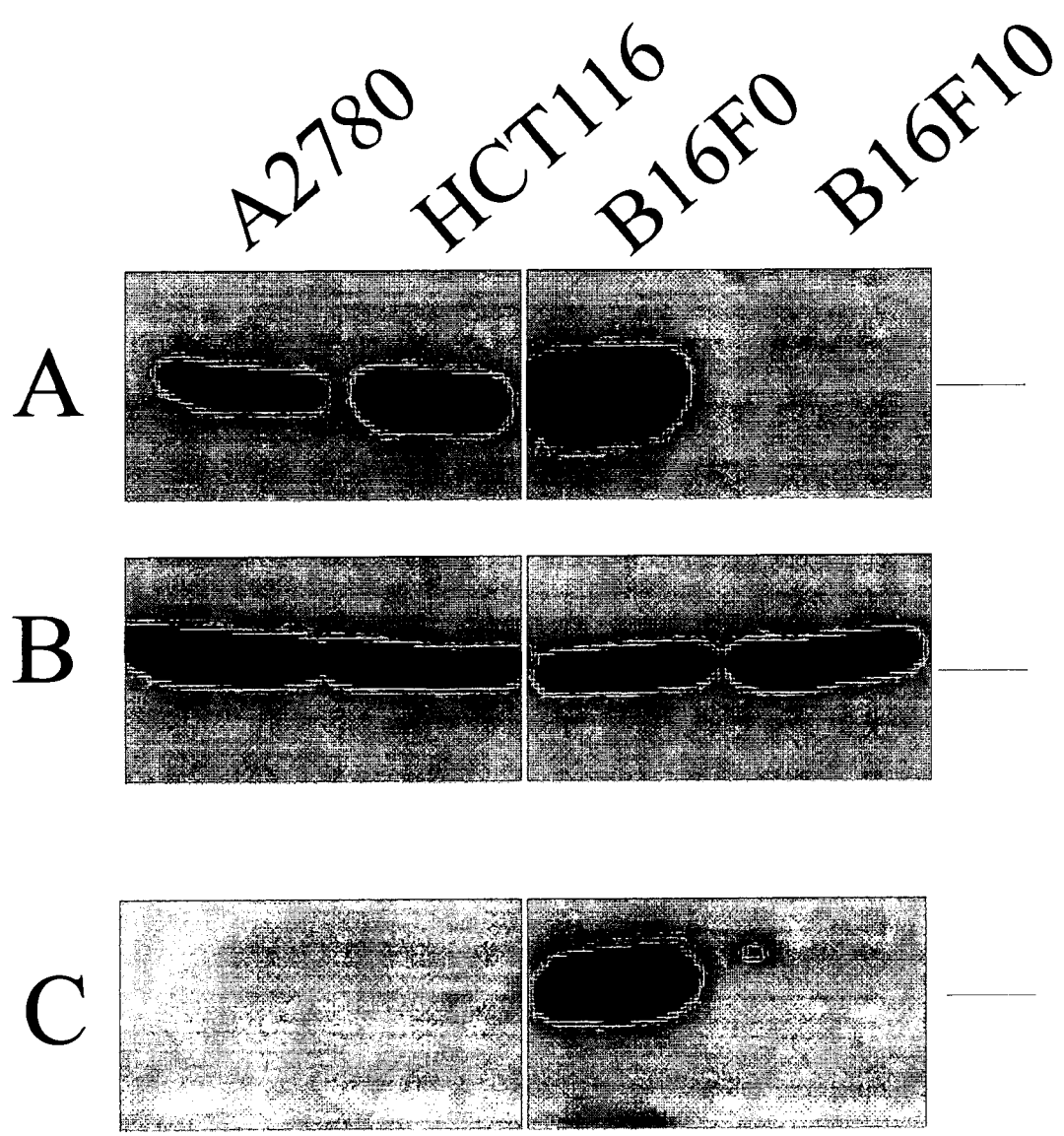
FIG. 12. Anti-PRL3 antibody 318 binds to both intracellular and externalised/secreted PRL-3 polypeptide. A. Intracellular PRL3, B. GAPDH control, C. Externalised/secreted PRL-3 polypeptide.

The results are shown in FIG. 12.

FIG. 12A. Western blot demonstrates that A2780, HCT116, and B16F0 are three cancer cell lines that express endogenous PRL-3 protein, while B16F10 is a PRL-3 non-expressing cancer cells.

FIG. 12B. GAPDH is used as a protein loading control.

FIG. 12C. Western blot analysis on four culture media that are harvested from the four cancer cell lines. PRL-3 phosphatase is found to be secreted out from B16F0 cells into culture medium while PRL-3 phosphatase was not found to be secreted out from the rest of the three cells, suggesting that the secretion of PRL-3 phosphatase could relate to cell type specific phenomena. The data suggest that in vivo, PRL-3 can be secreted into the blood stream in cancer patients. Phosphatase secretion has never been reported in our literature.

Example 27

Epitope Mapping of Anti-PRL1 and Anti-PRL3 Antibodies

Epitopes for each of the anti-PRL antibodies 269 and 318 are mapped as follows.

First, we exclude most of the amino acids that are identical among all three PRLs. Second, we select the differences in amino acid sequences among the three PRLs. Third, 28 peptides are specially designed for these specific regions that might be able to distinguish from each other for the binding of their respective antibody to its own specific regions.

We specially designed 28 PRL-1, PRL-2, and PRL-3 specific polypeptide spots and ordered from Genemed Synthesis, Inc. (www.genemedsyn.com). The 28 peptide spots are arranged as a map in Table E1 below that also indicates each polypeptide sequence corresponding to the spots to FIGS. 13A and 13B.

TABLE E1

28 peptides tested for epitope binding against anti-PRL1 antibody and anti-PRL3 antibody.

| Reference | A | B | C | D | E | f |
|---|---|---|---|---|---|---|
| 1 | TYKNMR | TLNKFI | NKFIEE | VCEATY | DTTLVE | KEGIHV |
| 2 | PSNQIV | KDSNGH | NGHRNN | SYENMR | TLNKFT | NKFTEE |
| 3 | VCDATY | DKAPVE | KEGIHV | PPNQIV | RDTNGH | SYRHMR |
| 4 | TLSTFI | STFIED | VCEVTY | DKTPLE | KDGITV | KAKFYN |
| 5 | PPGKVV | YNDPGS | KDPHTH | HTHKTR | | |

Figure 13A:
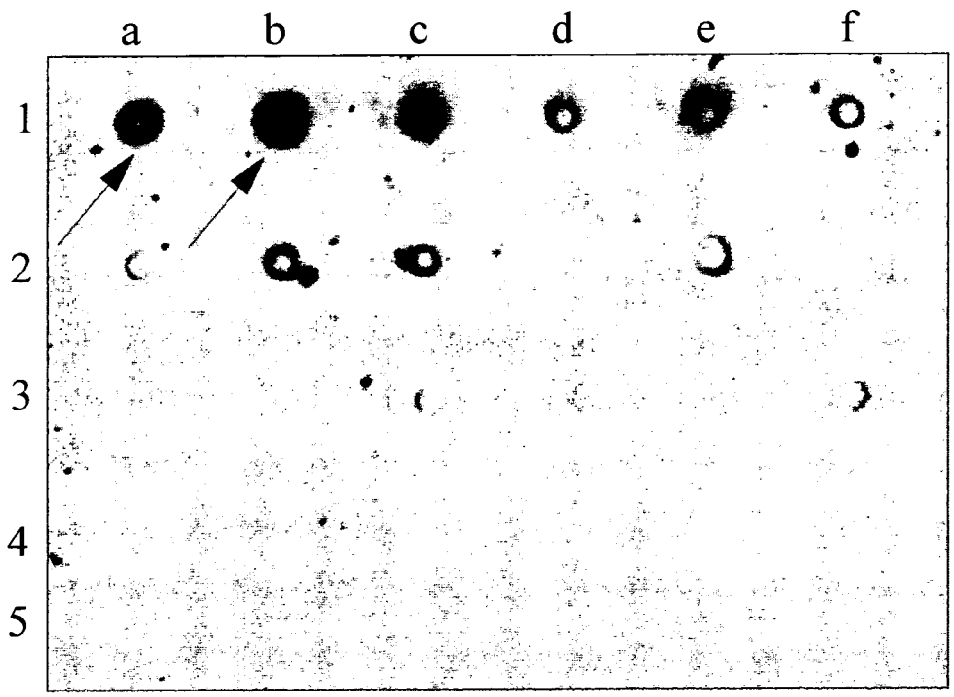
FIG. 13. Epitope mapping of anti-PRL1 antibody 269 and anti-PRL3 antibody 318. A. Peptides bound by anti-PRL1 antibody 269 as shown by Western Blot. B. Peptides bound by anti-PRL3 antibody 318 as shown by Western Blot.
Figure 13B:
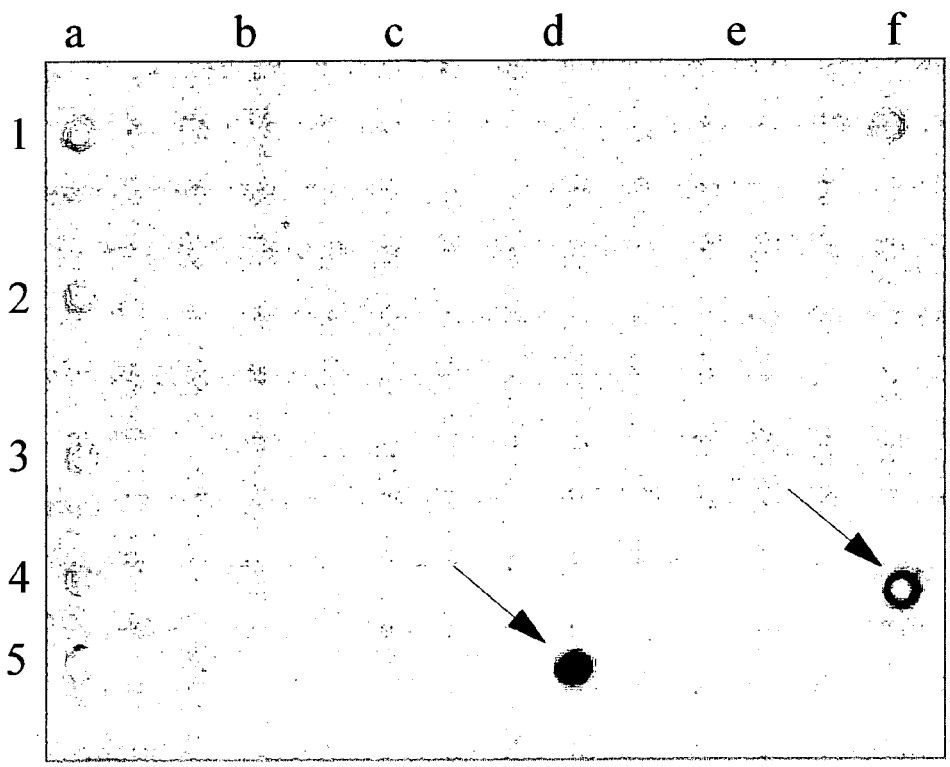

The Table shows a map representing an arrangement for each dot. The polypeptide sequences corresponding to the dots in FIG. 13A and FIG. 13B are shown.
Table E1 discloses the sequences in column A as SEQ ID NOS 13, 19, 25, 30, and 36, the sequences in column B as SEQ ID NOS 14, 20, 44-45, and 37, the sequences in column C as SEQ ID NOS 15, 42, 18, 32, and 47, the sequences in column D as SEQ ID NOS 17, 22, 27, 34, and 39, the sequences in column E as SEQ ID NOS 41, 24, 28, and 46, and the sequences in column F as SEQ ID NOS 18, 43, 29, and 35, all respectively, in order of appearance.

Protocol for PVDF Dot Blot Membrane

Blocking Membrane

1) Pre-wet membrane with 100% Methanol for a few seconds until it changes from opaque white to a uniform translucent gray when it is thoroughly wet. 2) Incubate the membrane in water for 45 minutes to elute the methanol. 3) Block in 3% BSA overnight at 4° C. with shaking.

Immunostaining

1) Incubate either with PRL-1 (#269 in FIG. 13A) or with PRL-3 (#318 in FIG. 13B) antibodies overnight at 4° C. with shaking. 2) Wash with PBS tween-20 four times, 10 minutes each. 3) Incubate with anti-mouse HRP 1:1000 2 hours at room temperature with shaking. 4) Wash with PBS Tween-20 four times, 10 minutes each.

ECL Developing

1) Incubate with detection agent 5 minutes at room temperature. 2) Drain excess buffer, place in plastic/saran wrap. 3) Develop in dark room.

Results

The results are shown in FIG. 13A and FIG. 13B.

FIG. 13A shows the results of a Western blot analysis to map epitopes for PRL-1 (clone #269) mAb. Two positive dots indicate that the PRL-1 mAb preferentially binds to two polypeptides (1a, TYKNMR (SEQ ID NO: 13); 1b, TLNKFI (SEQ ID NO: 14)).

FIG. 13B shows the results of Western blot analysis to map epitopes for PRL-3 (clone #318) mAb. The two dots indicate that the PRL-3 mAb preferentially binds to two polypeptide (4f, KAKFYN (SEQ ID NO: 35); 5d, HTHKTR (SEQ ID NO: 39)).

The results show that PRL-1 mAb (clone#269) and PRL-3 mAb (clone#318) may bind to epitopes that are formed by non-linearized sequences.

REFERENCES

1. Diamond R H, Cressman D E, Laz T M, et al. PRL-1, a unique nuclear protein tyrosine phosphatase, affects cell growth. Mol Cell Biol. 1994; 14:3752-62.
2. Wang J, Kirby C E, Herbst R. The tyrosine phosphatase PRL-1 localizes to the endoplasmic reticulum and the mitotic spindle and is required for normal mitosis. J Biol Chem. 2002; 277:46659-68.
3. Rouleau C, Roy A, Martin T S. et al. Protein tyrosine phosphatase PRL-3 in malignant cells and endothelial cells: expression and function. Mol Cancer Ther. 2006; 5:219-29.
4. Wang Q, Holms D I R, Powell S M, Lu Q L, Waxman J. Analysis of stromal-epithelial interactions in prostate cancer identifies PTPCAAX2 as a potential oncogene. Cancer Letters 2001; 175:63-9.
5. Guo K, Li J, Wang H H, et al. 2006. PRL-3 initiates tumour angiogenesis by recruiting endothelial cells in vitro and in vivo. Cancer Res. 2006; 66:9625-35.
6. Saha S, Bardelli A, Buckhaults P, et al. A phosphatase associated with metastasis of colorectal cancer. Science 2001; 294:1343-6.
7. Bardelli A, Saha S, Sager J A, et al. PRL-3 expression in metastatic cancer. Clin Cancer Res 2003; 9:5607-15.
8. Zeng Q, Dong J M, Guo K, et al. PRL-3 and PRL-1 promote cell migration, invasion, and metastasis. Cancer Res 2003; 63:2716-22.
9. Polato F, Codegoni A, Fruscio R, et al. PRL-3 phosphatases is implicated in ovarian cancer growth. Clin Cancer Res 2005; 11:6835-9.
10. Radke I, Gotte M, Kersting C, Mattsson B, Kiesel L, Wulfing, P. Expression and prognostic impact of the protein tyrosine phosphatases PRL-1, PRL-2, and PRL-3 in breast cancer. Br J Cancer 2006; 95:347-54.
11. Parker B S, Argani P, Cook B P, et al. Alterations in vascular gene expression in invasive breast carcinoma. Cancer Res 2004; 64:7857-66.
12. Miskad U A, Semba S, Kato H, Yokozaki H. Expression of PRL-3 phosphatase in human gastric carcinomas: close correlation with invasion and metastasis. Pathobiology 2004; 71:176-84.
13. Wang H H, Quah S Y, Dong J M, Manser E, Tang J P, Zeng Q. PRL-3 Down-regulates PTEN Expression and Signals through PI3K to Promote Epithelial-Mesenchymal Transition. Cancer Res 2007; 67:2922-6.
14. Imai K, Takaoka A. Comparing antibody and small-molecule therapies for cancer. Nat Rev Cancer 2006; 6:714-27.
15. Baker M. Upping the ante on antibodies. Nature Tech. 2005; 23:1065-72.
16. Si X, Zeng Q, Ng C H, Hong W, Pallen C J. Interaction of farnesylated PRL-2, a protein-tyrosine phosphatase, with the beta-subunit of geranylgeranyltransferase II. J Biol Chem. 2001; 276:32875-82.
17. Wang J, Kirby C E, Herbst R. The tyrosine phosphatase PRL-1 localizes to the endoplasmic reticulum and the mitotic spindle and is required for normal mitosis. J Biol Chem. 2002; 277:46659-68.
18. Zeng Q, Si X, Horstmann H, Xu Y, Hong W, Pallen C J. Prenylation-dependent association of protein-tyrosine phosphatases PRL-1, -2, -3 with the plasma membrane and the early endosome. J Biol Chem. 2000; 275:21444-52.
19. Li J, Guo K, Koh V W C. et al. Generation of PRL-3 and PRL-1 specific monoclonal antibodies as potential diagnostic markers for cancer metastases. Clin Cancer Res 2005; 11:2195-204
20. Britta W, Johannes L P, Laura J V. Breast cancer metastasis: markers and models. Nature Review Cancer 2005; 5:591-602.
21. Cooper S. Reappraisal of serum starvation, the restriction point, G0, and G1 phase arrest points. FASEB 2003; 17 333-40.
A1. Darrell C. Bessette & Dexin Qiu & Catherine J. Pallen PRL PTPs: mediators and markers of cancer progression Cancer Metastasis Rev DOI 10.1007/s10555-008-9121-3
A2. Rouleau C, Roy A, Martin T S. et al. Protein tyrosine phosphatase PRL-3 in malignant cells and endothelial cells: expression and function. Mol Cancer Ther. 2006; 5:219-29.
A3. Saha S, Bardelli A, Buckhaults P, et al. A phosphatase associated with metastasis of colorectal cancer. Science 2001; 294:1343-6.
A4. Polato F, Codegoni A, Fruscio R, et al. PRL-3 phosphatases is implicated in ovarian cancer growth. Clin Cancer Res 2005; 11:6835-9.
A5. Radke I, Gotte M, Kersting C, Mattsson B, Kiesel L, Wulfing, P. Expression and prognostic impact of the protein tyrosine phosphatases PRL-1, PRL-2, and PRL-3 in breast cancer. Br J Cancer 2006; 95:347-54.
6. Peng, L., Ning, J., Meng, L., & Shou, C. (2004). The association of the expression level of protein tyrosine phosphatase PRL-3 protein with liver metastasis and prognosis of patients with colorectal cancer. Journal of Cancer Research and Clinical Oncology, 130, 521-526.
A7. Miskad, U. A., Semba, S., Kato, H., Matsukawa, Y., Kodama, Y., Mizuuchi, E., et al. (2007). High PRL-3 expression in human gastric cancer is a marker of metastasis and grades of malignancies: An in situ hybridization study. Virchows Archiv, 450, 303-310.
A8. Sager J A, Benvenuti S, Bardelli A. PRL-3, A phosphatase for metastasis? Cancer Biology & Therapy 2004; 3:952-3.
A9. Zeng Q, Dong J M, Guo K, et al. PRL-3 and PRL-1 promote cell migration, invasion, and metastasis. Cancer Res 2003; 63:2716-22.
A10. Wu X P, Zeng H, Zhang X M, et al. Phosphatase of regenerating liver-3 promotes motility and metastasis of mouse melanoma cells. Am J of Pathol 2004; 164:2039-54.
A11. Wang H H, Quah S Y, Dong J M, Manser E, Tang J P, Zeng Q. PRL-3 Down-regulates PTEN Expression and Signals through PI3K to Promote Epithelial-Mesenchymal Transition. Cancer Res 2007; 67:2922-6.
A12. Guo K, Li J, Wang H H, et al. PRL-3 initiates tumour angiogenesis by recruiting endothelial cells in vitro and in vivo. Cancer Res 2006; 66:19: 9625-35.
A13. Imai K, Takaoka A. Comparing antibody and small-molecule therapies for cancer. Nat Rev Cancer 2006; 6:714-27.
A14. Baker M. Upping the ante on antibodies. Nature Tech. 2005; 23:1065-72.
A15. Zeng Q, Si X, Horstmann H, Xu Y, Hong W, Pallen C J. Prenylation-dependent association of protein-tyrosine phosphatases PRL-1, -2, -3 with the plasma membrane and the early endosome. J Biol Chem. 2000; 275:21444-52.

A16. Ke Guo*, Jie Li*, Jing Ping Tang*, Cheng Peow Bobby Tan, Haihe Wang and Qi Zeng1 Monoclonal antibodies target intracellular PRL phosphatases to inhibit cancer metastases in mice. CB&T in press
A17. Li J, Guo K, Koh V W C. et al. Generation of PRL-3 and PRL-1 specific monoclonal antibodies as potential diagnostic markers for cancer metastases. Clin Cancer Res 2005; 11:2195-204
A18. Brendon J H, Adrianus C M, Angeline P C, et al. Passive immunoprophylaxis and therapy with humanized monoclonal antibody specific for influenza A H5 hemagglutinin in mice. Respiratory Research 2006; 7:126-36.
A19. Britta W, Johannes L P, Laura J V. Breast cancer metastasis: markers and models. Nature Review Cancer 2005; 5:591-602.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method of treating a PRL-3 expressing cancer in an individual suffering or suspected to be suffering from said cancer, the method comprising administering a therapeutically effective amount of an antibody selected from the group consisting of:
   (a) an antibody which binds to PRL-3 and comprises a heavy chain variable region sequence comprising SEQ ID NO: 10 and a light chain variable region sequence comprising SEQ ID NO: 12;
   (b) an antibody which binds to PRL-3 and comprises a heavy chain variable region comprising SEQ ID NO: 6 and a light chain variable region sequence comprising SEQ ID NO: 8; and
   (c) an anti-PRL-3 antibody capable of binding to an epitope HTHKTR (SEQ ID NO: 39) and which is capable of binding to an intracellular PRL-3 polypeptide by being capable of crossing the plasma membrane;

or a pharmaceutical composition comprising such an antibody to the individual.

2. A method of treating a PRL-3 expressing cancer in an individual suffering or suspected to be suffering from said cancer, the method comprising diagnosing cancer in the individual and treating the individual by the method according to claim 1.

3. The method of claim 1, wherein the cancer is selected from the group consisting of: a PRL-3 expressing cancer; a metastatic cancer; colorectal cancer; ovarian cancer; breast cancer; liver cancer; pancreatic cancer; prostate cancer; gastric cancer; lung cancer; penis cancer; cervical cancer; brain cancer; esophageal cancer; bladder carcinoma; kidney renal cell carcinoma; ovary lymphoma and skin melanoma.

4. The method of claim 1, wherein said cancer is metastatic cancer.

5. The method of claim 2, wherein said cancer is metastatic cancer.

6. A method of treating a PRL-3 expressing cancer or inhibiting metastasis for a cancer expressing PRL-3, the method comprising administering to an individual in need of such treatment a pharmaceutical composition comprising an antibody that binds intracellular PRL-3, wherein said antibody is capable of binding to an epitope HTHKTR (SEQ ID NO: 39) and is capable of crossing the plasma membrane of an unpermeabilized cell, whereby said cancer is treated or metastasis of said cancer is inhibited.

7. The method of claim 1, wherein the antibody is a humanized antibody capable of binding to an epitope HTHKTR (SEQ ID NO: 39).

8. The method of claim 6, wherein the antibody is a humanized antibody.

* * * * *

```
                        SEQUENCE LISTING

<160> NUMBER OF SEQ ID NOS: 47

<210> SEQ ID NO 1
<211> LENGTH: 455
<212> TYPE: DNA
<213> ORGANISM: Mus musculus

<400> SEQUENCE: 1
gggaattcat gaaatgcagc tgggttattc tcttcctgtt ttcagtaact gcaggtgtcc      60
actcccaggt ccagtttcag cagtctgggg ctgaactggc aaaacctggg gcctcagtga     120
agatgtcctg caaggcttct ggctacactt ttactagtta tcggatgcac tgggtaaaac     180
agaggcctgg acagggtctg gaatggattg gatacattaa tcctagcact ggttatactg     240
agtacaatca gaagttcaag gacaaggcca cattgactgc agacaaatcc tccagcacag     300
cctacatgca actgagcagc ctgacatctg aggactctgc agtctattac tgttcaagct     360
atggtaactt cggctactgg ggccaaggca ccactctcac agtctcctca gagagtcagt     420
ccttcccaaa tgtcttcccc ctcgtaagct ggga                                 455

<210> SEQ ID NO 2
<211> LENGTH: 151
<212> TYPE: PRT
<213> ORGANISM: Mus musculus

<400> SEQUENCE: 2

Glu Phe Met Lys Cys Ser Trp Val Ile Leu Phe Leu Phe Ser Val Thr
1               5                   10                  15

Ala Gly Val His Ser Gln Val Gln Phe Gln Gln Ser Gly Ala Glu Leu
            20                  25                  30

Ala Lys Pro Gly Ala Ser Val Lys Met Ser Cys Lys Ala Ser Gly Tyr
        35                  40                  45

Thr Phe Thr Ser Tyr Arg Met His Trp Val Lys Gln Arg Pro Gly Gln
    50                  55                  60

Gly Leu Glu Trp Ile Gly Tyr Ile Asn Pro Ser Thr Gly Tyr Thr Glu
65                  70                  75                  80

Tyr Asn Gln Lys Phe Lys Asp Lys Ala Thr Leu Thr Ala Asp Lys Ser
                85                  90                  95

Ser Ser Thr Ala Tyr Met Gln Leu Ser Ser Leu Thr Ser Glu Asp Ser
```

```
                  100                 105                 110
Ala Val Tyr Tyr Cys Ser Ser Tyr Gly Asn Phe Gly Tyr Trp Gly Gln
            115                 120                 125

Gly Thr Thr Leu Thr Val Ser Ser Glu Ser Gln Ser Phe Pro Asn Val
        130                 135                 140

Phe Pro Leu Val Ser Leu Gly
145                 150

<210> SEQ ID NO 3
<211> LENGTH: 391
<212> TYPE: DNA
<213> ORGANISM: Mus musculus

<400> SEQUENCE: 3
ctgtctactg ctctctggtg agagtcagtc tcacttgtcg ggcaagtcag gacattggta      60
gtagcttaaa ctggcttcag cagaaagcag atggaaccat aaacgcctg atctatgcca     120 catccagttt agattctggt gtccccaaaa ggttcagtgg cagtaggtct gggtcagatt     180
attctctcac catcagcagc cttgagtctg aagattttgt agactattac tgtctacaat     240
atgctagttc tccgtggacg ttcggtggag gcaccaagct ggaaatcaaa cgggctgatg     300
ctgcacctca ctggagatcc tgcagatcac gcgaactgtg gctgcaccat ctgtcttcat     360
cttcccgcca tctgatgagc agttgaaatc t                                    391

<210> SEQ ID NO 4
<211> LENGTH: 127
<212> TYPE: PRT
<213> ORGANISM: Mus musculus

<400> SEQUENCE: 4

Val Tyr Cys Ser Leu Val Arg Val Ser Leu Thr Cys Arg Ala Ser Gln
1               5                   10                  15

Asp Ile Gly Ser Ser Leu Asn Trp Leu Gln Gln Lys Ala Asp Gly Thr
            20                  25                  30

Ile Lys Arg Leu Ile Tyr Ala Thr Ser Ser Leu Asp Ser Gly Val Pro
        35                  40                  45

Lys Arg Phe Ser Gly Ser Arg Ser Gly Ser Asp Tyr Ser Leu Thr Ile
    50                  55                  60

Ser Ser Leu Glu Ser Glu Asp Phe Val Asp Tyr Tyr Cys Leu Gln Tyr
65                  70                  75                  80

Ala Ser Ser Pro Trp Thr Phe Gly Gly Gly Thr Lys Leu Glu Ile Lys
                85                  90                  95

Arg Ala Asp Ala Ala Pro His Trp Arg Ser Cys Arg Ser Arg Glu Leu
            100                 105                 110

Trp Leu His His Leu Ser Ser Ser Arg His Leu Met Ser Ser
        115                 120                 125

<210> SEQ ID NO 5
<211> LENGTH: 473
<212> TYPE: DNA
<213> ORGANISM: Mus musculus

<400> SEQUENCE: 5
gggaattcat ggaatggagc tgggttattc tcttcctcct gtcaataatt gcaggtgtcc      60
attgccaggt ccagctgcag cagtctggac ctgagctggt gaagcctggg gcttcagtga     120
ggatatcctg caaggcttct ggctacacct tcacaagcta ctatatacac tgggtgaagc     180
agaggcctgg acaggacttg agtggattg atggattta tcctggaaat gttaatactg     240
```

```
agtacaatga aagttcagg ggcaaggcca cactgactgc agacaaatcc tccagcacag      300
cctacatgca gctcagcagc ctgacctctg aggactctgc ggtctatttc tgtgcaagtg      360
aggagaggaa ttaccctgg tttgcttact ggggccaagg gactctggtc actgtctctg      420
cagccaaaac gacacccca cccgtctatc ccttggtccc tggaagcttg gga              473
```

```
<210> SEQ ID NO 6
<211> LENGTH: 157
<212> TYPE: PRT
<213> ORGANISM: Mus musculus

<400> SEQUENCE: 6

Glu Phe Met Glu Trp Ser Trp Val Ile Leu Phe Leu Leu Ser Ile Ile
1               5                   10                  15

Ala Gly Val His Cys Gln Val Gln Leu Gln Gln Ser Gly Pro Glu Leu
                20                  25                  30

Val Lys Pro Gly Ala Ser Val Arg Ile Ser Cys Lys Ala Ser Gly Tyr
            35                  40                  45

Thr Phe Thr Ser Tyr Tyr Ile His Trp Val Lys Gln Arg Pro Gly Gln
        50                  55                  60

Gly Leu Glu Trp Ile Gly Trp Ile Tyr Pro Gly Asn Val Asn Thr Glu
65                  70                  75                  80

Tyr Asn Glu Lys Phe Arg Gly Lys Ala Thr Leu Thr Ala Asp Lys Ser
                85                  90                  95

Ser Ser Thr Ala Tyr Met Gln Leu Ser Ser Leu Thr Ser Glu Asp Ser
            100                 105                 110

Ala Val Tyr Phe Cys Ala Ser Glu Glu Arg Asn Tyr Pro Trp Phe Ala
        115                 120                 125

Tyr Trp Gly Gln Gly Thr Leu Val Thr Val Ser Ala Ala Lys Thr Thr
    130                 135                 140

Pro Pro Pro Val Tyr Pro Leu Val Pro Gly Ser Leu Gly
145                 150                 155
```

```
<210> SEQ ID NO 7
<211> LENGTH: 456
<212> TYPE: DNA
<213> ORGANISM: Mus musculus

<400> SEQUENCE: 7
tgggaattca tggagacaga cacactcctg ctatgggtgc tgctgctctg ggttccaggc      60
tccactggtg acattgtgct gacccaatct ccagcttctt ggctgtgtc tctagggcag      120 agggccacca tctcctgcaa ggccagccaa agtgttgaag atgatggtga aaattatatg      180
aactggtacc aacagaaacc aggacagtca cccaaactcc tcatctatgc tgcatccaat      240
ctagaatctg ggatcccagc caggttcagt ggcagtgggt ctgggacaga cttcaccctc      300
aacatccatc ctgtggagga ggaggatgct gcaacctatt actgtcagca aagtaatgag      360
gatccattca cgttcggctc ggggacaaag ttggaaataa aacgggctga tgctgcacca      420
actgtatcca tcttcccacc atccagtaag cttggg                                456
```

```
<210> SEQ ID NO 8
<211> LENGTH: 152
<212> TYPE: PRT
<213> ORGANISM: Mus musculus

<400> SEQUENCE: 8

Trp Glu Phe Met Glu Thr Asp Thr Leu Leu Leu Trp Val Leu Leu Leu
```

```
                1               5                   10                  15
Trp Val Pro Gly Ser Thr Gly Asp Ile Val Leu Thr Gln Ser Pro Ala
                    20                  25                  30

Ser Leu Ala Val Ser Leu Gly Gln Arg Ala Thr Ile Ser Cys Lys Ala
                35                  40                  45

Ser Gln Ser Val Glu Asp Asp Gly Glu Asn Tyr Met Asn Trp Tyr Gln
         50                  55                  60

Gln Lys Pro Gly Gln Ser Pro Lys Leu Leu Ile Tyr Ala Ala Ser Asn
 65                  70                  75                  80

Leu Glu Ser Gly Ile Pro Ala Arg Phe Ser Gly Ser Gly Ser Gly Thr
                    85                  90                  95

Asp Phe Thr Leu Asn Ile His Pro Val Glu Glu Asp Ala Ala Thr
                100                 105                 110

Tyr Tyr Cys Gln Gln Ser Asn Glu Asp Pro Phe Thr Phe Gly Ser Gly
            115                 120                 125

Thr Lys Leu Glu Ile Lys Arg Ala Asp Ala Ala Pro Thr Val Ser Ile
        130                 135                 140

Phe Pro Pro Ser Ser Lys Leu Gly
145                 150

<210> SEQ ID NO 9
<211> LENGTH: 471
<212> TYPE: DNA
<213> ORGANISM: Mus musculus

<400> SEQUENCE: 9
gggaattcat ggaatggagc tgggtttttcc tcttcctcct gtcaataatt gcaggtgtcc      60
attgccaggt ccagctgcag cagtctggac ctgagctggt gaagcctggg gcttcagtga     120
ggatatcctg caaggcttct ggctacacct tcacaaacta ctatatgcac tgggtgaagc     180
agaggcctgg acagggactt gagtggattg gatggattta ccctggaaat gttaatactt     240
attacaatga agttcagg gcaaggccac actgactgca gacaaatcct ccagcacagc      300
ctacatgcag ctcagcagcc tgacctctga ggactctgcg gtctatttct gtgcaagtga     360
ggagagaatt accctggtt tgcttactgg ggccaaggga ctctggtcac tgtctctgca     420
gccaaaacga caccccatc cgtctatccc ctggtccctg aagcttggg a               471

<210> SEQ ID NO 10
<211> LENGTH: 154
<212> TYPE: PRT
<213> ORGANISM: Mus musculus

<400> SEQUENCE: 10

Glu Phe Met Glu Trp Ser Trp Val Phe Leu Phe Leu Leu Ser Ile Ile
1               5                   10                  15

Ala Gly Val His Cys Gln Val Gln Leu Gln Gln Ser Gly Pro Glu Leu
                20                  25                  30

Val Lys Pro Gly Ala Ser Val Arg Ile Ser Cys Lys Ala Ser Gly Tyr
            35                  40                  45

Thr Phe Thr Asn Tyr Tyr Met His Trp Val Lys Gln Arg Pro Gly Gln
        50                  55                  60

Gly Leu Glu Trp Ile Gly Trp Ile Tyr Pro Gly Asn Val Asn Thr Tyr
 65                 70                  75                  80

Tyr Asn Glu Lys Phe Arg Ala Arg Pro His Leu Gln Thr Asn Pro Pro
                85                  90                  95

Ala Gln Pro Thr Cys Ser Ser Ala Ala Pro Leu Arg Thr Leu Arg Ser
```

Ile Ser Val Gln Val Arg Arg Glu Leu Pro Leu Val Cys Leu Leu Gly
            115                 120                 125

Pro Arg Asp Ser Gly His Cys Leu Cys Ser Gln Asn Asp Thr Pro Ile
130                 135                 140

Arg Leu Ser Pro Gly Pro Trp Lys Leu Gly
145                 150

<210> SEQ ID NO 11
<211> LENGTH: 453
<212> TYPE: DNA
<213> ORGANISM: Mus musculus

<400> SEQUENCE: 11
actagtcgac atggagtcag acacactgct gttatgggta ctgctgctct gggttccagg    60
ttccactggt gacattgtgc tgacacagtc tcctgcttcc ttagctgtat ctctggggca   120
gagggccacc atctcataca gggccagcaa aagtgtcagt acatctggct atagttatat   180
gcactggaac caacagaaac caggacagcc acccagactc ctcatctatc ttgtatccaa   240
cctagaatct ggggtccctg ccaggttcag tggcagtggg tctgggacag acttcaccct   300
caacatccat cctgtggagg aggaggatgc tgcaacctat tactgtcagc acattaggga   360
gcttacacgt tcggaggggg gaccaagctg gaaataaaac gggctgatgc tgcaccaact   420
gtatccatct tcccaccatc cataagcttg gga                                453

<210> SEQ ID NO 12
<211> LENGTH: 131
<212> TYPE: PRT
<213> ORGANISM: Mus musculus

<400> SEQUENCE: 12

Leu Val Asp Met Glu Ser Asp Thr Leu Leu Trp Val Leu Leu Leu
1               5                   10                  15

Trp Val Pro Gly Ser Thr Gly Asp Ile Val Leu Thr Gln Ser Pro Ala
                20                  25                  30

Ser Leu Ala Val Ser Leu Gly Gln Arg Ala Thr Ile Ser Tyr Arg Ala
            35                  40                  45

Ser Lys Ser Val Ser Thr Ser Gly Tyr Ser Tyr Met His Trp Asn Gln
        50                  55                  60

Gln Lys Pro Gly Gln Pro Pro Arg Leu Leu Ile Tyr Leu Val Ser Asn
65                  70                  75                  80

Leu Glu Ser Gly Val Pro Ala Arg Phe Ser Gly Ser Gly Ser Gly Thr
                85                  90                  95

Asp Phe Thr Leu Asn Ile His Pro Val Glu Glu Glu Asp Ala Ala Thr
            100                 105                 110

Tyr Tyr Cys Gln His Ile Arg Glu Leu Thr Arg Ser Glu Gly Gly Pro
        115                 120                 125

Ser Trp Lys
    130

<210> SEQ ID NO 13
<211> LENGTH: 6
<212> TYPE: PRT
<213> ORGANISM: Homo sapiens

<400> SEQUENCE: 13

Thr Tyr Lys Asn Met Arg
1               5

<210> SEQ ID NO 14
<211> LENGTH: 6
<212> TYPE: PRT
<213> ORGANISM: Homo sapiens

<400> SEQUENCE: 14

Thr Leu Asn Lys Phe Ile
1               5

<210> SEQ ID NO 15
<211> LENGTH: 6
<212> TYPE: PRT
<213> ORGANISM: Homo sapiens

<400> SEQUENCE: 15

Asn Lys Phe Ile Glu Glu
1               5

<210> SEQ ID NO 16
<211> LENGTH: 6
<212> TYPE: PRT
<213> ORGANISM: Homo sapiens

<400> SEQUENCE: 16

Asn Lys Phe Ile Glu Glu
1               5

<210> SEQ ID NO 17
<211> LENGTH: 6
<212> TYPE: PRT
<213> ORGANISM: Homo sapiens

<400> SEQUENCE: 17

Val Cys Glu Ala Thr Tyr
1               5

<210> SEQ ID NO 18
<211> LENGTH: 6
<212> TYPE: PRT
<213> ORGANISM: Homo sapiens

<400> SEQUENCE: 18

Lys Glu Gly Ile His Val
1               5

<210> SEQ ID NO 19
<211> LENGTH: 6
<212> TYPE: PRT
<213> ORGANISM: Homo sapiens

<400> SEQUENCE: 19

Pro Ser Asn Gln Ile Val
1               5

<210> SEQ ID NO 20
<211> LENGTH: 6
<212> TYPE: PRT
<213> ORGANISM: Homo sapiens

<400> SEQUENCE: 20

Lys Asp Ser Asn Gly His
1               5

<210> SEQ ID NO 21

```
<211> LENGTH: 6
<212> TYPE: PRT
<213> ORGANISM: Homo sapiens

<400> SEQUENCE: 21

Lys Asp Ser Asn Gly His
1               5

<210> SEQ ID NO 22
<211> LENGTH: 6
<212> TYPE: PRT
<213> ORGANISM: Homo sapiens

<400> SEQUENCE: 22

Ser Tyr Glu Asn Met Arg
1               5

<210> SEQ ID NO 23
<211> LENGTH: 6
<212> TYPE: PRT
<213> ORGANISM: Homo sapiens

<400> SEQUENCE: 23

Ser Tyr Glu Asn Met Arg
1               5

<210> SEQ ID NO 24
<211> LENGTH: 6
<212> TYPE: PRT
<213> ORGANISM: Homo sapiens

<400> SEQUENCE: 24

Thr Leu Asn Lys Phe Thr
1               5

<210> SEQ ID NO 25
<211> LENGTH: 6
<212> TYPE: PRT
<213> ORGANISM: Homo sapiens

<400> SEQUENCE: 25

Val Cys Asp Ala Thr Tyr
1               5

<210> SEQ ID NO 26
<211> LENGTH: 6
<212> TYPE: PRT
<213> ORGANISM: Homo sapiens

<400> SEQUENCE: 26

Val Cys Asp Ala Thr Tyr
1               5

<210> SEQ ID NO 27
<211> LENGTH: 6
<212> TYPE: PRT
<213> ORGANISM: Homo sapiens

<400> SEQUENCE: 27

Pro Pro Asn Gln Ile Val
1               5

<210> SEQ ID NO 28
<211> LENGTH: 6
<212> TYPE: PRT
<213> ORGANISM: Homo sapiens
```

```
<400> SEQUENCE: 28

Arg Asp Thr Asn Gly His
1               5

<210> SEQ ID NO 29
<211> LENGTH: 6
<212> TYPE: PRT
<213> ORGANISM: Homo sapiens

<400> SEQUENCE: 29

Ser Tyr Arg His Met Arg
1               5

<210> SEQ ID NO 30
<211> LENGTH: 6
<212> TYPE: PRT
<213> ORGANISM: Homo sapiens

<400> SEQUENCE: 30

Thr Leu Ser Thr Phe Ile
1               5

<210> SEQ ID NO 31
<211> LENGTH: 6
<212> TYPE: PRT
<213> ORGANISM: Homo sapiens

<400> SEQUENCE: 31

Thr Leu Ser Thr Phe Ile
1               5

<210> SEQ ID NO 32
<211> LENGTH: 6
<212> TYPE: PRT
<213> ORGANISM: Homo sapiens

<400> SEQUENCE: 32

Val Cys Glu Val Thr Tyr
1               5

<210> SEQ ID NO 33
<211> LENGTH: 6
<212> TYPE: PRT
<213> ORGANISM: Homo sapiens

<400> SEQUENCE: 33

Val Cys Glu Val Thr Tyr
1               5

<210> SEQ ID NO 34
<211> LENGTH: 6
<212> TYPE: PRT
<213> ORGANISM: Homo sapiens

<400> SEQUENCE: 34

Asp Lys Thr Pro Leu Glu
1               5

<210> SEQ ID NO 35
<211> LENGTH: 6
<212> TYPE: PRT
<213> ORGANISM: Homo sapiens

<400> SEQUENCE: 35
```

```
Lys Ala Lys Phe Tyr Asn
1               5

<210> SEQ ID NO 36
<211> LENGTH: 6
<212> TYPE: PRT
<213> ORGANISM: Homo sapiens

<400> SEQUENCE: 36

Pro Pro Gly Lys Val Val
1               5

<210> SEQ ID NO 37
<211> LENGTH: 6
<212> TYPE: PRT
<213> ORGANISM: Homo sapiens

<400> SEQUENCE: 37

Tyr Asn Asp Pro Gly Ser
1               5

<210> SEQ ID NO 38
<211> LENGTH: 6
<212> TYPE: PRT
<213> ORGANISM: Homo sapiens

<400> SEQUENCE: 38

Tyr Asn Asp Pro Gly Ser
1               5

<210> SEQ ID NO 39
<211> LENGTH: 6
<212> TYPE: PRT
<213> ORGANISM: Homo sapiens

<400> SEQUENCE: 39

His Thr His Lys Thr Arg
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 40

His His His His His His
1               5

<210> SEQ ID NO 41
<211> LENGTH: 6
<212> TYPE: PRT
<213> ORGANISM: Homo sapiens

<400> SEQUENCE: 41

Asp Thr Thr Leu Val Glu
1               5

<210> SEQ ID NO 42
<211> LENGTH: 6
<212> TYPE: PRT
<213> ORGANISM: Homo sapiens

<400> SEQUENCE: 42
```

```
Asn Gly His Arg Asn Asn
1               5

<210> SEQ ID NO 43
<211> LENGTH: 6
<212> TYPE: PRT
<213> ORGANISM: Homo sapiens

<400> SEQUENCE: 43

Asn Lys Phe Thr Glu Glu
1               5

<210> SEQ ID NO 44
<211> LENGTH: 6
<212> TYPE: PRT
<213> ORGANISM: Homo sapiens

<400> SEQUENCE: 44

Asp Lys Ala Pro Val Glu
1               5

<210> SEQ ID NO 45
<211> LENGTH: 6
<212> TYPE: PRT
<213> ORGANISM: Homo sapiens

<400> SEQUENCE: 45

Ser Thr Phe Ile Glu Asp
1               5

<210> SEQ ID NO 46
<211> LENGTH: 6
<212> TYPE: PRT
<213> ORGANISM: Homo sapiens

<400> SEQUENCE: 46

Lys Asp Gly Ile Thr Val
1               5

<210> SEQ ID NO 47
<211> LENGTH: 6
<212> TYPE: PRT
<213> ORGANISM: Homo sapiens

<400> SEQUENCE: 47

Lys Asp Pro His Thr His
1               5
```